(12) United States Patent
Marson et al.

(10) Patent No.: US 11,639,495 B2
(45) Date of Patent: May 2, 2023

(54) METHODS FOR SELECTION AND GENERATION OF GENOME EDITED T CELLS

(71) Applicants: The Regents of the University of California, Oakland, CA (US); Berkeley Lights, Inc., Emeryville, CA (US)

(72) Inventors: Alexander Marson, San Francisco, CA (US); Gregory G. Lavieu, Vitry sur Seine (FR); Annamaria Mocciaro, San Francisco, CA (US); Theodore L. Roth, San Francisco, CA (US); Magali Soumillon, Berkeley, CA (US); Hayley M. Bennett, Emeryville, CA (US)

(73) Assignees: The Regents of the University of California, Oakland, CA (US); Berkeley Lights, Inc., Emeryville, CA (US)

( * ) Notice: Subject to any disclaimer, the term of this patent is extended or adjusted under 35 U.S.C. 154(b) by 933 days.

(21) Appl. No.: 16/455,118

(22) Filed: Jun. 27, 2019

(65) Prior Publication Data

US 2020/0048606 A1  Feb. 13, 2020

Related U.S. Application Data

(63) Continuation of application No. PCT/US2017/069084, filed on Dec. 29, 2017, which is a continuation-in-part of application No. PCT/US2017/022518, filed on Mar. 15, 2017, and a continuation-in-part of application No. PCT/US2016/069468, filed on Dec. 30, 2016.

(Continued)

(51) Int. Cl.
*C12N 5/0783* (2010.01)
*B01L 3/00* (2006.01)
*C12N 15/10* (2006.01)

(52) U.S. Cl.
CPC ........ *C12N 5/0636* (2013.01); *B01L 3/50273* (2013.01); *B01L 3/502715* (2013.01);
(Continued)

(58) Field of Classification Search
CPC . C12N 5/0636; C12N 15/102; B01L 3/50273; B01L 3/502715; B01L 3/502761
(Continued)

(56) References Cited

U.S. PATENT DOCUMENTS 6,294,063 B1  9/2001 Becker et al.
6,767,535 B1  7/2004 Rollins et al.
(Continued)

FOREIGN PATENT DOCUMENTS

CN  101772580 A  7/2010
EP  0421380 B1  12/1995
(Continued)

OTHER PUBLICATIONS

Seung Woo Cho et al, "Targeted genome engineering in human cells with the Cas9 RNA-guided endonuclease", 2013, Nature Biotechnology, vol. 31, No. 3, pp. 230-232. (Year: 2013).*
(Continued)

*Primary Examiner* — Terrell H Matthews
(74) *Attorney, Agent, or Firm* — McNeill Baur PLLC

(57) ABSTRACT

Methods are described herein for isolating clonal populations of T cells having a defined genetic modification. The methods are performed, at least in part, in a microfluidic device comprising one or more sequestration pens. The methods include the steps of: maintaining individual T cells (or precursors thereof) that have undergone a genomic
(Continued)

editing process in corresponding sequestration pens of a microfluidic device; expanding the T cells into respective clonal populations of T cells; detecting, in one or more T cells of each clonal population, the absence of a cell surface marker that was present in the individual T cells (or precursors thereof); and detecting, in one or more T cells of each clonal population, the presence of a first nucleic acid sequence that is indicative of the presence of an on-target genome edit in the clonal population of T cells. Also described are compositions comprising one or more clonal populations of T cells isolated according to the methods disclosed herein.

26 Claims, 27 Drawing Sheets

Specification includes a Sequence Listing.

Related U.S. Application Data

(60) Provisional application No. 62/573,682, filed on Oct. 17, 2017, provisional application No. 62/560,184, filed on Sep. 18, 2017.

(52) U.S. Cl.
CPC ...... *B01L 3/502761* (2013.01); *C12N 15/102* (2013.01); *B01L 2400/0424* (2013.01); *C12N 2533/50* (2013.01); *C12N 2539/00* (2013.01)

(58) Field of Classification Search
USPC ...................................................... 435/372.3
See application file for complete search history.

(56) References Cited

U.S. PATENT DOCUMENTS

| | | |
|---|---|---|
| 6,942,776 B2 | 9/2005 | Medoro |
| 7,090,759 B1 | 8/2006 | Seul |
| 7,312,085 B2 | 12/2007 | Chou et al. |
| 7,442,339 B2 | 10/2008 | Sundararajan et al. |
| 8,921,041 B2 | 12/2014 | Wang et al. |
| 10,239,058 B2 | 3/2019 | Lavieu et al. |
| 2003/0008364 A1 | 1/2003 | Wang et al. |
| 2004/0072278 A1* | 4/2004 | Chou .................. G01N 15/1456 436/63 |
| 2004/0191789 A1 | 9/2004 | Manaresi et al. |
| 2004/0197905 A1 | 10/2004 | Hafeman |
| 2005/0112548 A1 | 5/2005 | Segawa et al. |
| 2005/0129581 A1 | 6/2005 | McBride et al. |
| 2005/0175981 A1 | 8/2005 | Voldman et al. |
| 2005/0221333 A1 | 10/2005 | Sundararajan et al. |
| 2006/0091015 A1 | 5/2006 | Lau |
| 2006/0154361 A1 | 7/2006 | Wikswo et al. |
| 2007/0095669 A1 | 5/2007 | Lau et al. |
| 2007/0183934 A1 | 8/2007 | Diercks et al. |
| 2007/0242105 A1 | 10/2007 | Srinivasan et al. |
| 2008/0302732 A1 | 12/2008 | Soh et al. |
| 2009/0023608 A1 | 1/2009 | Hung et al. |
| 2009/0170186 A1 | 7/2009 | Wu et al. |
| 2010/0003666 A1 | 1/2010 | Lee et al. |
| 2010/0101960 A1 | 4/2010 | Ohta et al. |
| 2010/0273681 A1 | 10/2010 | Cerrina et al. |
| 2010/0330056 A1 | 12/2010 | Yee et al. |
| 2011/0053151 A1 | 3/2011 | Hansen et al. |
| 2011/0117634 A1 | 5/2011 | Halamish et al. |
| 2011/0143964 A1 | 6/2011 | Zhou et al. |
| 2011/0217274 A1 | 9/2011 | Reid |
| 2011/0262906 A1 | 10/2011 | Dimov et al. |
| 2012/0009671 A1 | 1/2012 | Hansen et al. |
| 2012/0015347 A1 | 1/2012 | Singhal et al. |
| 2012/0015382 A1 | 1/2012 | Weitz et al. |
| 2012/0118740 A1 | 5/2012 | Garcia et al. |
| 2012/0156675 A1 | 6/2012 | Lueerssen et al. |
| 2012/0208266 A1 | 8/2012 | Bookbinder et al. |
| 2012/0325665 A1 | 12/2012 | Chiou et al. |
| 2013/0071403 A1 | 3/2013 | Rolland et al. |
| 2013/0118905 A1 | 5/2013 | Morimoto et al. |
| 2013/0171628 A1 | 7/2013 | Carlo et al. |
| 2013/0190212 A1 | 7/2013 | Handique et al. |
| 2013/0204076 A1 | 8/2013 | Han et al. |
| 2013/0261021 A1 | 10/2013 | Bocchi et al. |
| 2013/0288065 A1 | 10/2013 | Chen et al. |
| 2014/0017791 A1 | 1/2014 | Chapman et al. |
| 2014/0116881 A1 | 5/2014 | Chapman et al. |
| 2014/0124370 A1 | 5/2014 | Short et al. |
| 2014/0186295 A1 | 7/2014 | Kupper et al. |
| 2015/0018226 A1 | 1/2015 | Hansen et al. |
| 2015/0151298 A1* | 6/2015 | Hobbs .............. B01L 3/502761 435/7.1 |
| 2015/0151307 A1* | 6/2015 | Breinlinger ....... B01L 3/502761 204/547 |
| 2015/0165436 A1 | 6/2015 | Chapman et al. |
| 2015/0166326 A1 | 6/2015 | Chapman et al. |
| 2015/0306599 A1 | 10/2015 | Khandros et al. |
| 2016/0158757 A1 | 6/2016 | Breinlinger et al. |
| 2016/0171686 A1 | 6/2016 | Du et al. |
| 2016/0184821 A1 | 6/2016 | Hobbs et al. |
| 2016/0193604 A1 | 7/2016 | McFarland et al. |
| 2016/0199837 A1 | 7/2016 | Breinlinger et al. |
| 2016/0252495 A1 | 9/2016 | Ricicova et al. |
| 2016/0312165 A1 | 10/2016 | Lowe et al. |
| 2017/0224734 A1 | 8/2017 | Chapman et al. |
| 2018/0147576 A1* | 5/2018 | Lavieu .................. C12M 23/16 |
| 2018/0282806 A1* | 10/2018 | Esfandyarpour ........................... G01N 33/54313 |
| 2018/0298318 A1 | 10/2018 | Kurz et al. |
| 2019/0217297 A1 | 7/2019 | Lavieu et al. |
| 2019/0240665 A1 | 8/2019 | Lionberger et al. |
| 2020/0408751 A1* | 12/2020 | Lionberger ...... G01N 33/54366 |

FOREIGN PATENT DOCUMENTS

| | | |
|---|---|---|
| EP | 0981408 B1 | 4/2004 |
| KR | 20100008222 A | 1/2010 |
| WO | 2002088702 A2 | 11/2002 |
| WO | 2004040001 A2 | 5/2004 |
| WO | 2004089810 A2 | 10/2004 |
| WO | 2005100541 A2 | 10/2005 |
| WO | 2007008609 A2 | 1/2007 |
| WO | 2007024701 A2 | 3/2007 |
| WO | 2008119066 A1 | 10/2008 |
| WO | 2008150814 A2 | 12/2008 |
| WO | 2009130694 A2 | 10/2009 |
| WO | 2010040851 A2 | 4/2010 |
| WO | 2010115167 A2 | 10/2010 |
| WO | 2010147078 A1 | 12/2010 |
| WO | 2011160430 A1 | 12/2011 |
| WO | 2012024658 A2 | 2/2012 |
| WO | 2012037030 A2 | 3/2012 |
| WO | 2012072823 A1 | 6/2012 |
| WO | 2012162779 A1 | 12/2012 |
| WO | 2013019491 A1 | 2/2013 |
| WO | 2013130714 A1 | 9/2013 |
| WO | 2015039100 A1 | 3/2015 |
| WO | 2016100977 A1 | 6/2016 |
| WO | 2017123978 A1 | 7/2017 |
| WO | WO-2017160991 A1 * | 9/2017 ........ B01L 3/502761 |
| WO | 2014138315 | 7/2018 |
| WO | WO-2018126205 A1 * | 7/2018 ........ B01L 3/502715 |

OTHER PUBLICATIONS

Cho et al., "Targeted Genome Engineering in Human Cells with RNA-Guided Endonucleases," Nature Biotechnology, Supplemental Information, 2013, 1-11.

Zeng et al., "Synergy of IL-21 and IL-15 in Regulating CD8+ T Cell Expansion and Function," J Exp Med, 2005, 201(1):139-148.

Extended European Search Report received in EP17888107.4, dated Aug. 6, 2020, 9 pages.

(56) References Cited

OTHER PUBLICATIONS

Bacheleitner-Hoffmann et al., Stimulation of Autologous Antitumor T-Cell Responses Against Medullary Thyroid Carcinoma Using Tumor Lysate-Pulsed Dendritic Cells, J. Clin. Endo. & Metabl. 87(3): 1098-1104 (2002).
Chen et al., Microfluidic approaches for cancer cell detection, characterization, and separation, Lab on a Chip 12:1753 (2012).
Chiou et al., Massively parallel manipulation of single cells and microparticles using optical images, Nature 436:370-73 (2005).
Chiou, "Massively parallel optical manipulation of cells, micro- and nano-particles on optoelectronic devices," Dissertation, University of California at Berkeley, 2005 (147 pages).
Cho et al, Targeted genome engineering in human cells with the Cas9 RNA-guided endonuclease, Nautre Biotechnology, vol. 31, No. 3, Mar. 2013, pp. 230-232. (Year: 2013).
Chung et al., "DNA-Tethered Membranes Formed by Giant Vesicle Rupture," Journal of Structural Biology, 2009, 168:190-199.
Chung et al., Imaging single-cell signaling dynamics with a deterministic high-density single-cell trap array, Anal. Chem.83(18):7044-7052 (2011).
Collarini et al., Potent High-Affinity Antibodies for Treatment and Prophylaxis of Respiratory Synctial Virus Derived from B Cells of Infected Patients, J. Immunol., 183: 6338-6345 (2009).
Cong et al., "Multiplex Genome Engineering Using CRISPR/Cas Systems," Science, 2013, 339:819-23.
Curran KJ, et al. Chimeric antigen receptors for T cell immunotherapy: current understanding and future directions. J Gene Med. 14:405-415. 2012.
Di Carlo et al., "Dynamic Single Cell Analysis for Quantitative Biology," Analytical Chemistry, 2006, 7918-7925.
File History of U.S. Appl. No. 15/488,139, filed Apr. 14, 2017.
File History of U.S. Appl. No. 15/802,174, filed Nov. 2, 2017.
File History of U.S. Appl. No. 16/259,538, filed Jan. 28, 2019.
Gel et al., "Microorifice-Based High-Yield Cell Fusion on Microfluidic Chip: Electrofusion of Selected Pairs and Fusant Viability," IEEE Transactions on Nanobioscience, 2009, 8(4):300-305.
Germain et al., Tertiary lymphoid structure-associated B cells are key players in anti-tumor immunity, Frontiers in Immunology, 6: Article 67, 1-14 (2015).
Gilham et al, "CAR-T cells and solid tumors: tuning T cells to challenge an inveterate foe," Trends in Molecular Medicine, 2012, 18(7)377-384.
Goc J, et al. Characteristics of tertiary lymphoid structures in primary cancers. Oncolmmunology. 2(12):e26836. Dec. 2013.
Han et al., "CRISPR-Cas9 Delivery to Hard-to-Transfect Cells via Membrane Deformation," Sci. Adv., 2015, 1(7):1-8.
He et al., In vitro generation of cytotoxic T lymphocyte response using dendritic cell immunotherapy in osteosarcoma, Oncology Letters 12: 1101-1106 (2016).
He, et al., "Knock-in of Large Reporter Genes in Human Cells via CRISPR/Cas9-Induced Homology-Dependent and Independent DNA Repair," Nucleic Acids Research, 2016, 44(9):e85.
Hsu et al., "Sorting of Differentiated Neurons using Phototransistor-Based Optoelectronic Tweezers for Cell Replacement Therapy of Neurodegenerative Diseases," IEEE Conference on Transducers, 2009, 4 pages.
Hu et al., "A High-Throughput Dielectrophoresis-Based Cell Electrofusion Microfluidic Device," Electrophoresis, 2011, 32:2488-2495.
Hultquist et al., "A Cas9 Ribonucleoprotein Platform for Functional Genetic Studies of HIV-Host Interactions in Primary Human T Cells," Cell Reports, 2016, 17(5):1438-52.
Hung et al., "Continuous Perfusion Microfluidic Cell Culture Array for High-Throughput Cell-Based Assays," Biotech and Bioengineering, 2004, 89(1):1-8.
International Search Report and Written Opinion for PCT Application Serial No. PCT/US2016/069468 dated Mar. 17, 2017; 9 pages.
International Search Report and Written Opinion for PCT/US2017/069084, dated May 4, 2018, 72 pages.
International Search Report for PCT/US2017/022518, dated Aug. 7, 2017, 19 pages.
Jinek et al., "RNA-Programmed Genome Editing in Human Cells," eLife, 2013, 2:e00471.
Liang et al., "Rapid and Highly Efficient Mammalian Cell Engineering via Cas9 Protein Transfection," J. Biotechnol., 2015, 208:44-53.
Lin et al., "An Optically Induced Cell Lysis Device Using Dielectrophoresis," Applied Physics Letters, 2009, 94:033901.
Lowe, Jr. et al., "Deposition of Dense Siloxane Monolayers from Water and Trimethoxyorganosilane Vapor," Langmuir, 2011, 27:9928-9935.
Lowe, Jr., "Controlled Vapor Deposition of Azide-Terminated Siloxane Monolayers: A Platform for Tailoring Oxide Surfaces," Dissertation, Stanford University, Aug. 2011, 152 pages.
Maheswaran et al., Ex Vivo Culture of CTCs: An Emerging Resource to Guide Cancer Therapy, Cancer Research 75(12) (2015).
Mali et al., "RNA-Guided Human Genome Engineering via Cas9," Science, 2013, 339:823-26.
Martucci, "Nanoparticle-based strategy for personalized B-cell lymphoma therapy", International Journal of Nanomedicine, 2016:11, 14 pages.
Mocciaro, A. et al., Light-Activated Cell Identification and Sorting (LACIS): A New Method to Identify and Select Edited Clones on a Microfluidic Device. BioRxiv. Oct. 17, 2017; pp. 1-20.
Nevill et al., Integrated microfluidic cell culture and lysis on a chip, Lab on A Chip 7:1689-95 (2007).
Nishio N, et al. Armed Oncolytic Virus Enhances Immune Functions of Chimeric Antigen Receptor-Modified T Cells in Solid Tumors. Cancer Res. 74(18):5195-205. Sep. 15, 2014.
Parker LL, et al., gentleMACS™ Dissociation of melanoma tumors for the generation of tumor-infiltrating lymphocyte cultures foradoptive cell therapy MACS: Milteyi Biotec. Copyright 2011.
Peterson et al., "Long-Term Multilineage Engraftment of Autologous Genome-Edited Hematopoietic Stem Cells in Nonhuman Primates," Blood, 2016, 127(20):2416-26.
Poirot et al., "Multiplex Genome Edited T-Cell Manufacturing Platform for "off-the-shelf" Adoptive T-Cell Immunotherapies," Cancer Research, 2015, 75(18):3853-64.
Pule, et al. A Chimeric T Cell Antigen Receptor That Augments Cytokine Release and Supports Clonal Expansion of Primary Human T Cells. Molecular Therapeutics. 12(5):933-941. Nov. 2005, available online on Jun. 23, 2005.
Schena et al., Dependence of Immunoglobin Class Switch Recombination in B Cells on Vesicular Release of ATP and CD73 Ectonucleotidase Activity, Cell Reports, 3:1824-1831 (2013).
Schumacher et al., Neoantigens in cancer immunotherapy, Science 348:69-74 (2015).
Schumann et al., "Generation of Knock-In Primary Human T Cells using Cas9 Ribonucleoproteins," PNAS, 2015, 112(33):10437-42.
Smith et al., Sorting Out Cell Sorting: Flow Cytometry, Magnetic Beads or Microchips?, downloaded from http://www.biocompare.com/Editorial- Articles/126327- Cell-Sorting, 2013.
Somaweera et al., "Generation of a Chemical Gradient Across an Array of 256 Cell Cultures in a Single Chip," Analyst, 2013, 138(19):5566-5571.
Topfer et al., DAP12-Based Activating Chimeric Antigen Receptor for NK Cell Tumor Immunotherapy, J. Immunology 194:3201-3212 (2015).
Valley et al., Optoelectronic Tweezers as a Tool for Parallel Single-Cell Manipulation and Stimulation, IEEE Transactions on Biomedical Circuits and Systems 3(6):424-30 (2009).
Mocciaro et al., "Light-activated cell identification and sorting (LACIS) for selection of edited clones on a nanofluidic device," Commun Biol, 2018, 1(1):1-8.
Chiou, P.-Y, "Massively Parallel Optical Manipulation of Single Cells, Micro- and Nano-particles on Optoelectronic Devices," PhD Dissertation, University of California at Berkeley, Berkeley, CA, 2005 (pp. 1-137, submitted in two parts).
Feldman et al., "Adoptive Cell Therapy—Tumor-Infiltrating Lymphocytes, T-Cell Receptors, and Chimeric Antigen Receptors," Semin. Oncol., 2015, 42(4):626-639.

(56) References Cited

OTHER PUBLICATIONS

File History of U.S. Appl. No. 15/488,139, filed Apr. 14, 2017 by Kevin T. Chapman, Xiaohua Wang, Xiao Guan Radstrom, Yelena Bronevetsky, Guido K. Stadler, Gregory G. Levieu and Annamaria Mocciaro.
File History of U.S. Appl. No. 15/802,174, filed Nov. 2, 2017, by Gregory G. Lavieu, Annamaria Mocciaro, Xiao Guan Radstrom, Jason M. McEwen, Magali Soumillon, J, Tanner Nevill, Volker L.S. Kurz, Patricia A. Dyck,and Ravi K. Ramenani.
File History of U.S. Appl. No. 16/259,538, filed Jan. 28, 2019, by Gregory G. Lavieu, Annamaria Mocciaro, Xiao Guan Radstrom, Jason M. McEwen, Magali Soumillon, J, Tanner Nevill, Volker L.S. Kurz, Patricia A. Dyck,and Ravi K. Ramenani.
Lecault et al., "Microfluidic single cell analysis: from promise to practice" Current Opinion in Chemical Biology, vol. 16, No. 3-4, Aug. 1, 2012, pp. 381-390.
Lee et al., "Microchip-based one step DNA extraction and real-time PCR in one chamber for rapid pathogen identification" Lab on Chip 2006.
Levi et al., "Characterization of tumor infiltrating Natural Killer cell subset," Oncotarget, 2015, 6(15):13835-13843.
Li et al., "Impact of chemokine receptor CXCR3 on tumor-infiltrating lymphocyte recruitment associated with favorable prognosis in advanced gastric cancer," Int J Clin Exp Pathol, 2015, 8(11):14725-14732.
Iliescu et al., Continuous Field-Flow Separation of Particle Populations in a Dielectrophoretic Chip with Three Dimensional Electrodes, Applied Physics Letters 90:234104 (2007).
Ramadan, Q. et al., Simultaneous cell lysis and bead trapping in a continuous flow microfluidic device. Sensors and Actuators B, Jun. 6, 2005, vol. 113, No. 2, pp. 944-955.
Rathore et al., "CD3+, CD4+ & CD8+ tumour infiltrating lymphocytes (TILs) are predictors of favourable survival outcome in infiltrating ductal carcinoma of breast," Indian J Med Res, 2014, 140:361-369.
Santegoets et al., "IL-21 promotes the expansion of CD27+CD28+ tumor infiltrating lymphocytes with high cytotoxic potential and low collateral expansion of regulatory T cells," J Transl Med, 2013, 11:37-47.
Takeha et al., "Stromal Expression of MMP-9 and Urokinase Receptor is Inversely Associated with Liver Metastasis and with Infiltrating Growth in Human Colorectal Cancer: A Novel Approach from Immune/Inflammatory Aspect," Jpn. J. Cancer Res., 1997, 88:72-81.
WO2010147078, University of Tokyo, Machine Translation, Dec. 23, 2010, 12 pages.
Xu, Guoling et al.,. Recent Trends in Dielectrophoresis, Informacije MIDEM, 2010, vol. 40, Issue No. 4, pp. 253-262.
KR20100008222 machine translation dated Jan. 25, 2010, 10 pages.
Van Dongen, "EuroFlow antibody panels for standardized n-dimensional flow cytometric immunophenenotyping of normal, reactive and malignant leukocytes", Leukemia 2010; 24; 18 pages (also distributed as Handout at 14th EHA Congress, Berlin, DE, Jun. 4, 2009).
Vera J, et al., T lymphocytes redirected against the light chain of human immunoglobulin efficiently kill mature B lymphocyte-derived malignant cells. Blood. 108:3890-3897. 2006.
Watkins SK, et al. Video Article: Isolation of Immune Cells from Primary Tumors. Journal of Visualized Experiments. vol. 64:e3952. Jun. 2012. The video component of this article can be found at http://www.jove.com/video/3952/.
Wickham et al., "Targeted Adenovirus-Mediated Gene Delivery to T Cells via CD3," J Virology, 1997, 71(10):7663-69.
X Wang et al. "Manufacture of tumor- and virus-specific T lymphocytes for adoptive cell therapies" Cancer Gene Ther.; Jun. 25, 2015; 22 pages.
Yi et al., "Microfluidics Technology for Manipulation and Analysis of Biological Cells," Analytica Chimica Acta, 2006, 560:1-23.

* cited by examiner

METHODS FOR SELECTION AND GENERATION OF GENOME EDITED T CELLS

This application is a continuation of International Patent Application No. PCT/US2017/069084, filed Dec. 29, 2017, which: is a continuation-in-part of International Application No. PCT/US2016/069468, filed on Dec. 30, 2016, and a continuation-in-part of International Application No. PCT/US2017/022518, filed on Mar. 15, 2017; and claims the benefit of U.S. Provisional Application No. 62/560,184, filed on Sep. 18, 2017, and U.S. Provisional Application No. 62/573,682, filed on Oct. 17, 2017. Each of the foregoing disclosures is herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jun. 26, 2019, is named 2019-06-27_01149-0017-00US_SeqListing.txt and is 8.0 kilobytes in size.

FIELD

The present invention generally relates to methods for identifying T cells that having a desired genotype following genome editing.

BACKGROUND

Immunotherapy is a rapidly advancing approach to fighting disease that attempts to supplement and/or modulate a patient's immune response through the administration of antibodies, immune cells, or other immunological agents. For example, T cells have been developed as a therapeutic agent for many years (see, e.g., Sharpe et al., Disease Models & Mechanisms 8, 337-350 (2015); Maus et al., Annul. Rev. Immunol. 32, 289-225 (2014), Wu et al., Cancer J. 18, 160-175 (2012)). In recent years, there has been a push to improve the antigen specificity of T cells by genetically manipulating the T cells to be redirected against target antigens expressed by tumors. T cells have been engineered to express modified TCRs (so-called TCR therapies) or protein-fusion-derived chimeric antigen receptors (CARs) that have enhanced specificity for a target antigen. As another example, check point inhibitor antibodies have been developed to block inhibitory signals produced by proteins such as PD-1 and CTLA-4 that negatively regulate the function of T cells.

Despite the promising results obtained from immunotherapies to date, there are potentially significant side effects. Moreover, the modification of immune cells, such as T cells, can be unpredictable and/or unstable. To address these problems, researchers have sought to use better, more precise methods for modifying T cells. The present application discloses novel approaches for modifying T cells that address these needs.

SUMMARY

In a first aspect, a method is disclosed for generating a clonal population of genetically modified T cells in a microfluidic device having a at least one sequestration pen. The microfluidic device can include a plurality of sequestration pens, and the method can be applied to a corresponding plurality of T cells, either sequentially or in parallel. The method can include: maintaining in a sequestration pen of the microfluidic device a first T cell, wherein the first T cell or a precursor thereof has undergone a genomic editing process; expanding the first T cell into a clonal population of T cells; and detecting, in one or more T cells of the clonal population, (i) the absence of a cell surface marker that was present in the first T cell or the precursor thereof, and/or (ii) the presence of a first nucleic acid sequence, wherein the first nucleic acid sequence indicates the presence of an on-target genome edit in the clonal population of T cells. In some embodiments, the first T cell may be a mammalian T cell, such as a T cell derived from a human, ape, monkey, rat, mouse, hamster, guinea pig, cow, pig, sheep, horse, dog, cat, or the like. In some embodiments, the first T cell can express CD3, optionally in combination with at least one marker selected from CD4, CD8, T-bet, GATA-3, CD25, Foxp3, ROR-gammaT, CD38, and CD40. In some embodiments, the precursor of the first T cell is a progenitor cell, such as a thymic progenitor cell.

Additional aspects and embodiments are disclosed or otherwise made evident in the detailed description, associated drawings, and claims that follow.

DETAILED DESCRIPTION

Figure 1A:
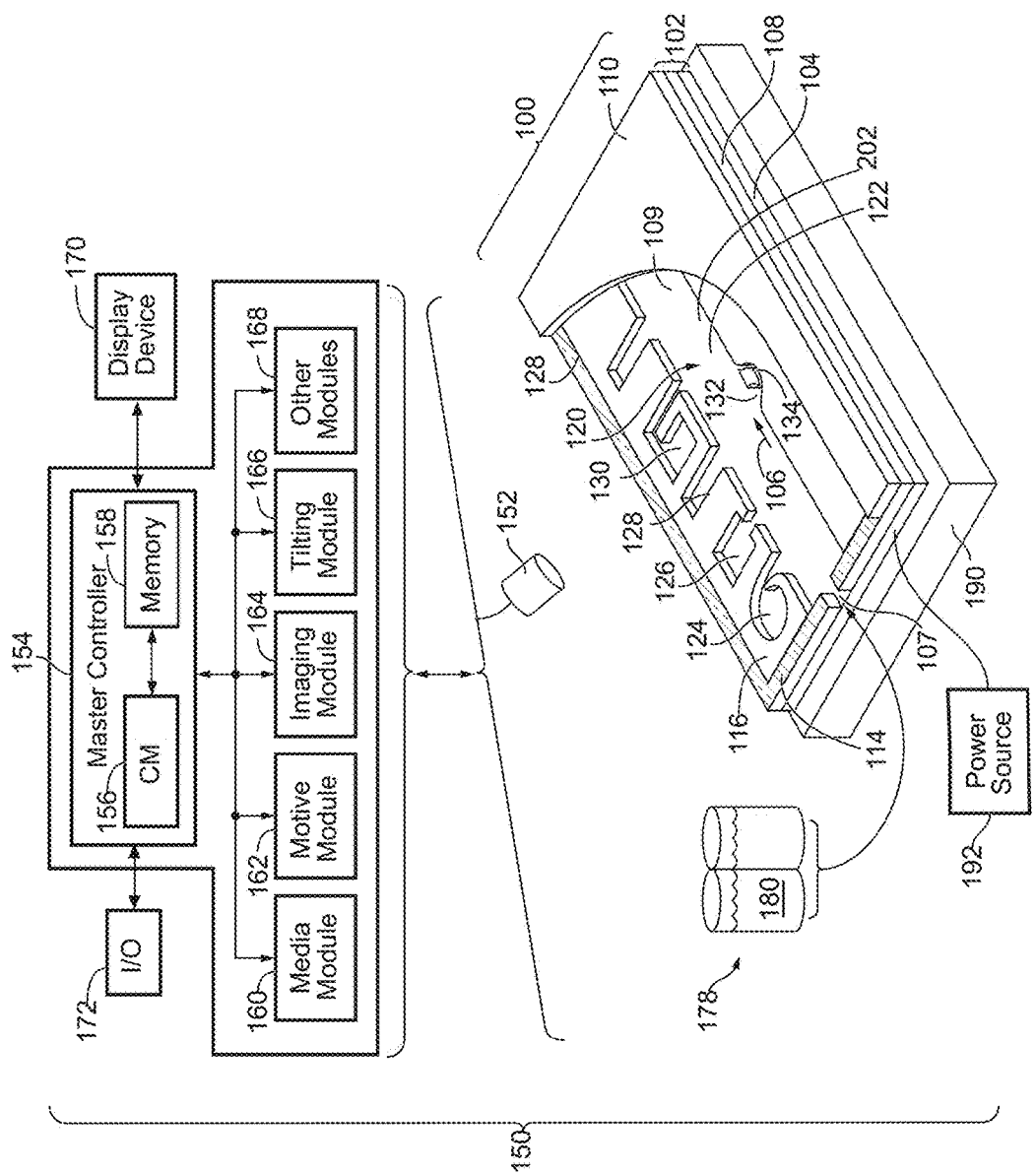
FIG. 1A illustrates an example of a system for use with a microfluidic device and associated control equipment according to some embodiments of the disclosure.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Where dimensions of microfluidic features are described as having a width or an area, the dimension typically is described relative to an x-axial and/or y-axial dimension, both of which lie within a plane that is parallel to the substrate and/or cover of the microfluidic device. The height of a microfluidic feature may be described relative to a z-axial direction, which is perpendicular to a plane that is parallel to the substrate and/or cover of the microfluidic device. In some instances, a cross sectional area of a microfluidic feature, such as a channel or a passageway, may be in reference to a x-axial/z-axial, a y-axial/z-axial, or an x-axial/y-axial area.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least one port configured to allow the fluid (and, optionally, micro-objects suspended in the fluid) to flow into and/or out of the microfluidic device. Typically, a microfluidic circuit of a microfluidic device will include a flow region, which may include a microfluidic channel, and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 µL. The microfluidic circuit may be configured to have a first end fluidically connected with a first port (e.g., an inlet) in the microfluidic device and a second end fluidically connected with a second port (e.g., an outlet) in the microfluidic device.

As used herein, a "nanofluidic device" or "nanofluidic apparatus" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 nL or less. A nanofluidic device may comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 µL to 20 nL, 1 to 10 nL, 1 to 15 nL, 1 to 20 nL, 1 to 25 nL, or 1 to 50 nL. In other embodiments, one or more (e.g., all) of the at least one circuit elements are configured to hold a volume of fluid of about 20 nL to 200 nL, 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 100,000 microns to about 500,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein. The flow channel may include valves, and the valves may be of any type known in the art of microfluidics. Examples of microfluidic channels that include valves are disclosed in U.S. Pat. Nos. 6,408,878 and 9,227,200, each of which is herein incorporated by reference in its entirety.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, the connection region and the isolation region of a microfluidic sequestration pen.

As used herein, the term "constriction" refers generally to a narrowing of a width of a circuit element (or an interface between two circuit elements) in a microfluidic device. The constriction can be located, for example, at the interface between the isolation region and the connection region of a microfluidic sequestration pen of the instant disclosure.

As used herein, the term "transparent" refers to a material which allows visible light to pass through without substantially altering the light as is passes through.

As used herein, the term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells; biological organelles; vesicles, or complexes; synthetic vesicles; liposomes (e.g., synthetic or derived from membrane preparations); lipid nanorafts, and the like; or a combination of inanimate micro-objects and biological micro-objects (e.g., microbeads attached to cells, liposome-coated microbeads, liposome-coated magnetic beads, or the like). Beads may include moieties/molecules covalently or non-covalently attached, such as fluorescent labels, proteins, carbohydrates, antigens, small molecule signaling moieties, or other chemical/biological species capable of use in an assay. Lipid nanorafts have been described, for example, in Ritchie et al. (2009) "Reconstitution of Membrane Proteins in Phospholipid Bilayer Nanodiscs," Methods Enzymol., 464:211-231.

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

As used herein, a "colony" of biological cells refers to 2 or more cells (e.g. about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than 1000 cells).

As used herein, the term "genome" refers to all the genetic material in a cell that can be passed from a parent cell to a daughter cell. In certain embodiments, the genetic material is chromosomal DNA and, optionally, any epigenetic modifications thereto. In certain embodiments, the genetic material includes both chromosomal DNA and mitochondrial DNA and, optionally, any epigenetic modifications to the chromosomal DNA and/or the mitochondrial DNA.

As used herein, the term "maintaining (a) cell(s)" refers to providing an environment comprising both fluidic and gaseous components and, optionally a surface, that provides the conditions necessary to keep the cells viable and/or expanding.

As used herein, the term "expanding" when referring to cells, refers to increasing in cell number.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein, "capture moiety" is a chemical or biological species, functionality, or motif that provides a recognition site for a micro-object. A selected class of micro-objects may recognize the in situ-generated capture moiety and may bind or have an affinity for the in situ-generated capture moiety. Non-limiting examples include antigens, antibodies, and cell surface binding motifs.

As used herein, "flowable polymer" is a polymer monomer or macromer that is soluble or dispersible within a fluidic medium (e.g., a pre-polymer solution). The flowable polymer may be input into a microfluidic flow region and flow with other components of a fluidic medium therein.

As used herein, "photoinitiated polymer" refers to a polymer (or a monomeric molecule that can be used to generate the polymer) that upon exposure to light, is capable of crosslinking covalently, forming specific covalent bonds, changing regiochemistry around a rigidified chemical motif, or forming ion pairs which cause a change in physical state, and thereby forming a polymer network. In some instances, a photoinitiated polymer may include a polymer segment bound to one or more chemical moieties capable of crosslinking covalently, forming specific covalent bonds, changing regiochemistry around a rigidified chemical motif, or forming ion pairs which cause a change in physical state. In some instances, a photoinitiated polymer may require a photoactivatable radical initiator to initiate formation of the polymer network (e.g., via polymerization of the polymer).

As used herein, "antibody" refers to an immunoglobulin (Ig) and includes both polyclonal and monoclonal antibodies; primatized (e.g., humanized); murine; mouse-human; mouse-primate; and chimeric; and may be an intact molecule, a fragment thereof (such as scFv, Fv, Fd, Fab, Fab' and F(ab)'2 fragments), or multimers or aggregates of intact molecules and/or fragments; and may occur in nature or be produced, e.g., by immunization, synthesis or genetic engineering. An "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'2, scFv, light chain variable region (VL), heavy chain variable region (VH), and combinations thereof.

As used herein, the binding of a first molecule to a second molecule is specific if the first molecule binds to a particular surface or epitope on the second molecule, in a particular orientation, with a binding affinity that is greater than the affinity between the first molecule and other surfaces or epitopes on the second molecule to which the first molecule binds non-specifically. A specific binding interaction can be characterized by a KD of about $1\times10^{-6}M^{-1}$, about $5\times10^{-7}M^{-1}$, about $2.5\times10^{-7}M^{-1}$, about $1\times10^{-7}M^{-1}$, about $5\times10^{8}M^{-1}$, about $2.5\times10^{-8}M^{-1}$, about $1\times10^{8}M^{-1}$, about $5\times10^{-9}M^{-1}$, about $2.5\times10^{-9}M^{-1}$, about $1\times10^{-9}M^{-1}$, or less. An example of a specific binding interaction is the binding of an epitope by the variable region of an antibody.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the microfluidic device.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein, "isolating a micro-object" confines a micro-object to a defined area within the microfluidic device. The micro-object may still be capable of motion within an in situ-generated capture structure.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Microfluidic Devices and Systems for Operating and Observing Such Devices.

FIG. 1A illustrates an example of a microfluidic device 100 and a system 150 which can be used generate clonal populations of genetically modified cells. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1A, suitable microfluidic devices can include a plurality (e.g., 2 or 3) of such microfluidic circuits. Regardless, the microfluidic device 100 can be configured to be a nanofluidic device. As illustrated in FIG. 1A, the microfluidic circuit 120 may include a plurality of microfluidic sequestration pens 124, 126, 128, and 130, where each sequestration pens may have one or more openings in fluidic communication with flow path 106. In some embodiments of the device of FIG. 1A, the sequestration pens may have only a single opening in fluidic communication with the flow path 106. As discussed further below, the microfluidic sequestration pens comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1A but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow regions (which may include or be one or more flow channels), chambers, pens, traps, and the like. In the microfluidic circuit 120 illustrated in FIG. 1A, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials- and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1A. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1A or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1A also shows a system 150 for operating and controlling microfluidic devices, such as microfluidic device 100. System 150 includes an electrical power source 192, an imaging device (incorporated within imaging module 164), and a tilting device 190 (incorporated within tilting module 166).

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device (part of imaging module 164, discussed below) can comprise a device, such as a digital camera, for capturing images inside microfluidic circuit 120. In some instances, the imaging device further comprises a detector having a fast frame rate and/or high sensitivity (e.g. for low light applications). The imaging device can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3B, the imaging device may further include a microscope (or an optical train), which may or may not include an eyepiece.

System 150 further comprises a tilting device 190 (part of tilting module 166, discussed below) configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 00 relative to x- and y-axes), a vertical orientation (i.e. at 900 relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 1B and 1C, the enclosure 102 can comprise a dielectrophoresis (DEP), optoelectronic tweezers (OET) and/or opto-electrowetting (OEW) configuration (not shown in FIG. 1A), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device. For example, the imaging module 164 can receive and process image data from the imaging device. Image data from the imaging device can comprise any type of information captured by the imaging device (e.g., the presence or absence of micro-objects, droplets of medium, accumulation of label, such as fluorescent label, etc.). Using the information captured by the imaging device, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1A, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. The walls of the sequestration pen extend from the inner surface 109 of the base to the inside surface of the cover 110 to provide enclosure. The opening of the pen to the microfluidic channel 122 is oriented at an angle to the flow 106 of fluidic medium 180 such that flow 106 is not directed into the pens. The flow may be tangential or orthogonal to the plane of the opening of the pen. In some instances, pens 124, 126, 128, 130 are configured to physically corral one or more micro-objects within the microfluidic circuit 120. Sequestration pens in accordance with the present disclosure can comprise various shapes, surfaces and features that are optimized for use with DEP, OET, OEW, fluid flow, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful in producing clonal cell populations, such as isolating a one genetically modified cell from other genetically modified cells. Growth, analysis, and optionally generation of a genetically modified cell (e.g., by contacting a cell with a genome editing biomolecule under conditions conducive to the formation of a genetically modified cell) may all be performed on an individual basis and, in some embodiments, may be performed on an individual time scale. In some embodiments, the microfluidic circuit 120 comprises a plurality of identical microfluidic sequestration pens.

In some embodiments, the microfluidic circuit 120 comprises a plurality of microfluidic sequestration pens, wherein two or more of the sequestration pens comprise differing structures and/or features which provide differing benefits for generating and analyzing clonal populations of genetically modified cells. One non-limiting example may include expanding a single cell into a clonal colony of cells in one type of pen, while extracting nucleic acid from one or more cells of the clonal colony in another type of pen. In another embodiment, at least one of the sequestration pens can be configured to have electrical contacts suitable for electroporation of cells. Microfluidic devices useful for producing clonal populations of genetically modified cells may include any of the sequestration pens 124, 126, 128, and 130 or variations thereof, and/or may include pens configured like those shown in FIGS. 2B, 2C, 2D, 2E and 2F, as discussed below.

In the embodiment illustrated in FIG. 1A, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens is configured (e.g., relative to a channel 122) such that the sequestration pens can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the microfluidic channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the embodiments of the current disclosure. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the embodiments of the current disclosure.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 1B:
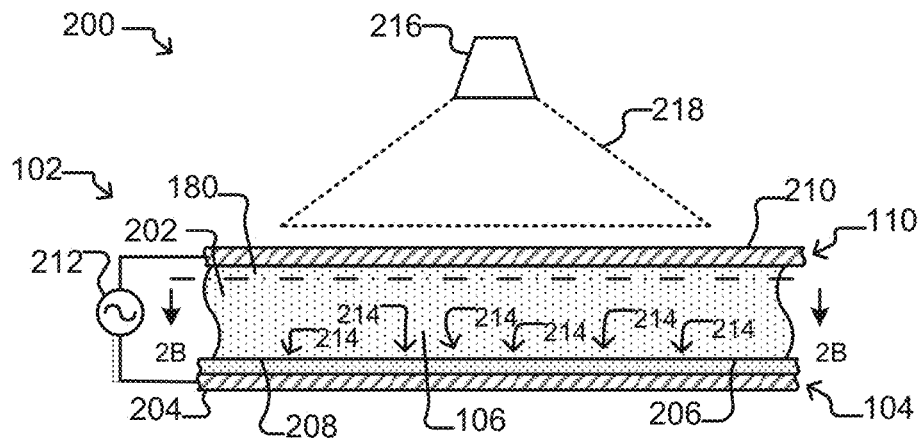
FIGS. 1B and 1C illustrate a microfluidic device according to some embodiments of the disclosure.

FIGS. 1B, 1C, and 2A-2H illustrates various embodiments of microfluidic devices that can be used in the practice of the embodiments of the present disclosure. FIG. 1B depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an optoelectrowetting (OEW) configuration. Examples of suitable OET configurations are illustrated in the following U.S. patent documents, each of which is incorporated herein by reference in its entirety: U.S. Pat. No. RE 44,711 (Wu et al.)

(originally issued as U.S. Pat. No. 7,612,355); U.S. Pat. No. 7,956,339 (Ohta et al.), and U.S. Patent Application Publication No. 2016/0184821 (Hobbs et al.). Examples of OEW configurations are illustrated in U.S. Pat. No. 6,958,132 (Chiou et al.) and U.S. Pat. No. 9,533,306 (Chiou et al.), and in International Application Publication No. WO 2017/075295 (Lowe, Jr. et al.), each of which is incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.), their corresponding International Publications WO2015/164846 and WO2015/164847, and in International Application Publication No. WO 2017/075295 (Lowe, Jr. et al.), all of which are incorporated herein by reference in their entirety.

Examples of microfluidic devices having pens in which biological micro-objects (e.g., cells, such as mammalian cells, including T cells), can be placed, cultured, and/or monitored have been described, for example, in U.S. Patent Application Publication Nos. 2014/0116881 (application no. Ser. No. 14/060,117, filed Oct. 22, 2013), 2015/0151298 (application Ser. No. 14/520,568, filed Oct. 22, 2014), and 2015/0165436 (application Ser. No. 14/521,447, filed Oct. 22, 2014), each of which is incorporated herein by reference in its entirety. U.S. patent application Ser. Nos. 14/520,568 and 14/521,447 also describe exemplary methods of analyzing secretions of cells cultured in a microfluidic device. Each of the foregoing applications further describes microfluidic devices configured to produce dielectrophoretic (DEP) forces, such as optoelectronic tweezers (OET) or configured to provide opto-electro wetting (OEW). For example, the optoelectronic tweezers device illustrated in FIG. 2 of US 2014/0116881 is an example of a device that can be utilized in embodiments of the present disclosure to select and move an individual biological micro-object or a group of biological micro-objects.

Microfluidic Device Motive Configurations.

As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 1C:
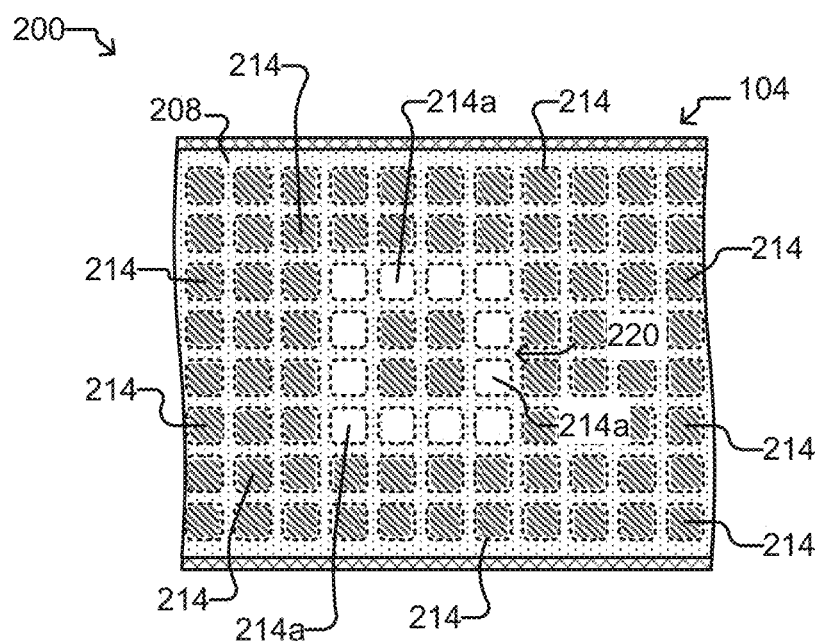

One example of a microfluidic device 200 comprising a DEP configuration is illustrated in FIGS. 1B and 1C. While for purposes of simplicity FIGS. 1B and 1C show a side cross-sectional view and a top cross-sectional view, respectively, of a portion of an enclosure 102 of the microfluidic device 200 having a region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 1B, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 1B and 1C can have an optically-actuated DEP configuration. Accordingly, changing patterns of light 218 from the light source 216, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 1C, a light pattern 218 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 218 projected from a light source 216 into the microfluidic device 200. Whether the DEP forces attract or repel nearby micro-objects can depend on such parameters as the frequency of the power source 212 and the dielectric properties of the medium 180 and/or micro-objects (not shown).

The square pattern 220 of illuminated DEP electrode regions 214a illustrated in FIG. 1C is an example only. Any pattern of the DEP electrode regions 214 can be illuminated (and thereby activated) by the pattern of light 218 projected into the microfluidic device 200, and the pattern of illuminated/activated DEP electrode regions 214 can be repeatedly changed by changing or moving the light pattern 218.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 μm. In such embodiments, the DEP electrode regions 214 can be created anywhere and in any pattern on the inner surface 208 of the electrode activation substrate 206, in accordance with the light pattern 218. The number and pattern of the DEP electrode regions 214 thus need not be fixed, but can correspond to the light pattern 218. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 218. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 218, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 218.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), and U.S. Patent Publication No. 2016/0184821 (Hobbs et al.) (see, e.g., devices 200, 502, 504, 600, and 700 illustrated throughout the drawings, and descriptions thereof), the entire contents of each of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 216 can alternatively be used to illuminate the enclosure 102 from below.

With the microfluidic device 200 of FIGS. 1B-1C having a DEP configuration, the motive module 162 can select a micro-object (not shown) in the medium 180 in the region/chamber 202 by projecting a light pattern 218 into the microfluidic device 200 to activate a first set of one or more DEP electrodes at DEP electrode regions 214a of the inner surface 208 of the electrode activation substrate 206 in a pattern (e.g., square pattern 220) that surrounds and captures the micro-object. The motive module 162 can then move the in situ-generated captured micro-object by moving the light pattern 218 relative to the microfluidic device 200 to activate a second set of one or more DEP electrodes at DEP electrode regions 214. Alternatively, the microfluidic device 200 can be moved relative to the light pattern 218.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 220), one or more micro-objects in region/chamber 202 can be trapped and moved within the region/chamber 202. The motive module 162 in FIG. 1A can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material, as described below. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.) and International Patent Application Publication No. WO 2017/075295 discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 218 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 218 (or moving microfluidic device 200 relative to the light source 216) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1A can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and U.S. Patent Application Publication Nos. 2014/0124370 (Short et al.), 2015/0306598 (Khandros et al.), 2015/0306599 (Khandros et al.), and 2016/0184821 (Hobbs et al.).

Sequestration Pens.

Figure 2A:
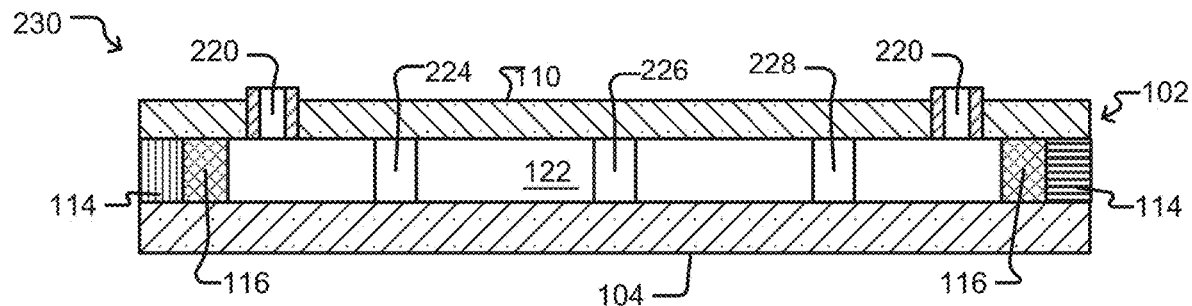
FIGS. 2A and 2B illustrate isolation pens according to some embodiments of the disclosure.
Figure 2B:
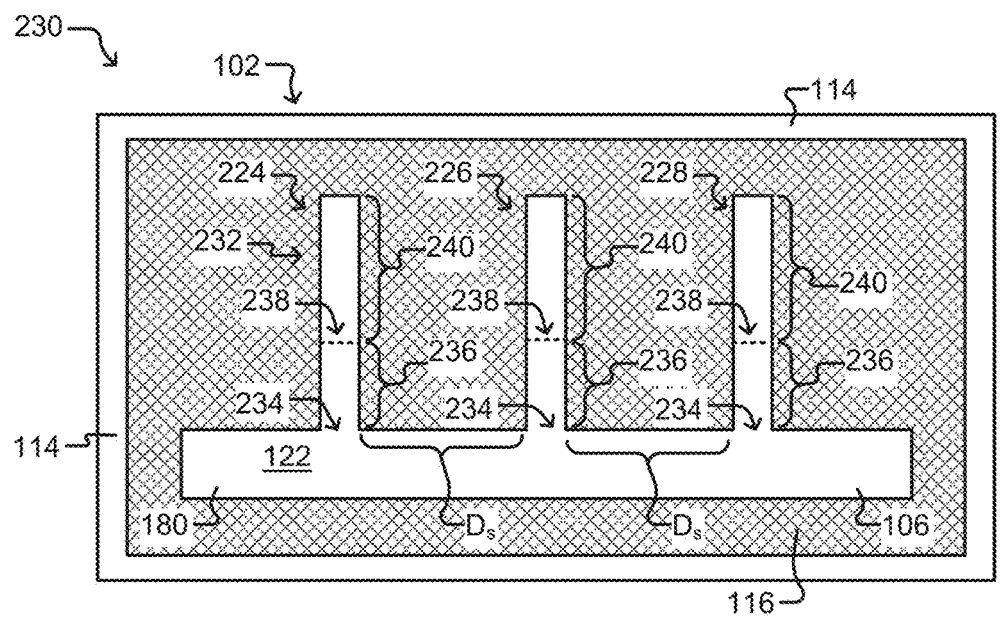
Figure 2C:
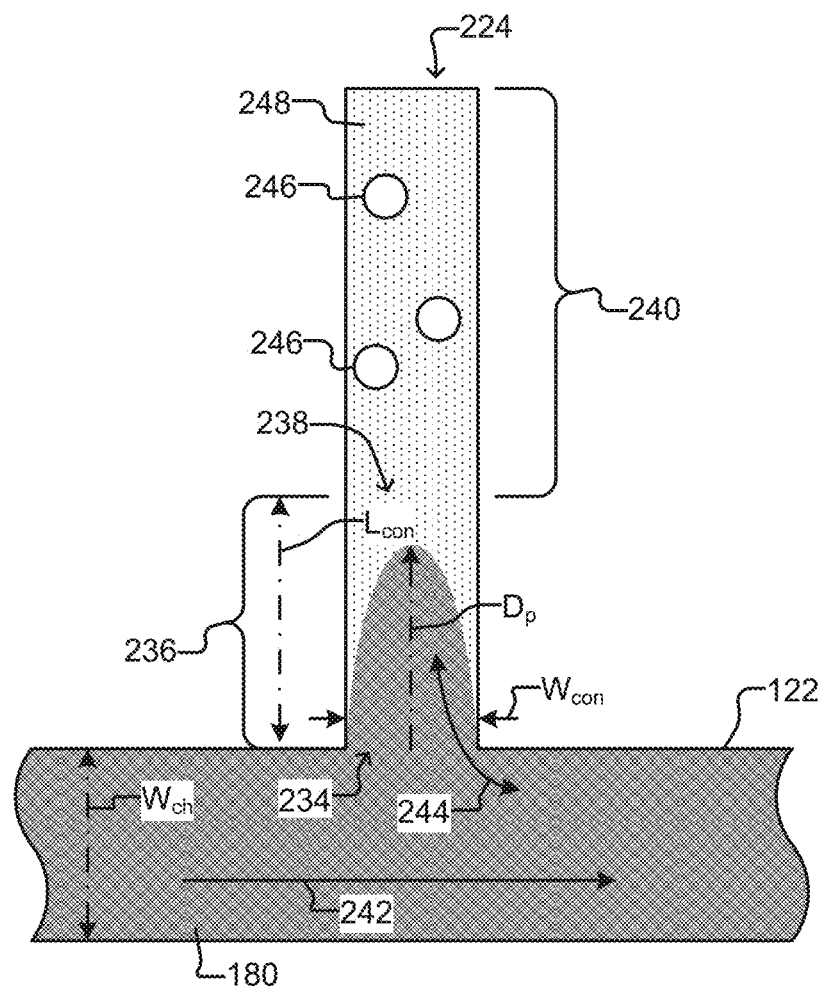
FIG. 2C illustrates a detailed sequestration pen according to some embodiments of the disclosure.

Non-limiting examples of generic sequestration pens 224, 226, and 228 are shown within the microfluidic device 230 depicted in FIGS. 2A-2C. Each sequestration pen 224, 226, and 228 can comprise an isolation structure 232 defining an isolation region 240 and a connection region 236 fluidically connecting the isolation region 240 to a channel 122. The connection region 236 can comprise a proximal opening 234 to the microfluidic channel 122 and a distal opening 238 to the isolation region 240. The connection region 236 can be configured so that the maximum penetration depth of a flow of a fluidic medium (not shown) flowing from the microfluidic channel 122 into the sequestration pen 224, 226, 228 does not extend into the isolation region 240. Thus, due to the connection region 236, a micro-object (not shown) or other material (not shown) disposed in an isolation region 240 of a sequestration pen 224, 226, 228 can thus be isolated from, and not substantially affected by, a flow of medium 180 in the microfluidic channel 122.

The sequestration pens 224, 226, and 228 of FIGS. 2A-2C each have a single opening which opens directly to the microfluidic channel 122. The opening of the sequestration pen opens laterally from the microfluidic channel 122. The electrode activation substrate 206 underlays both the microfluidic channel 122 and the sequestration pens 224, 226, and 228. The upper surface of the electrode activation substrate 206 within the enclosure of a sequestration pen, forming the floor of the sequestration pen, is disposed at the same level or substantially the same level of the upper surface the of electrode activation substrate 206 within the microfluidic channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 microns, 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the microfluidic channel 122 (or flow region) and sequestration pens may be less than about 3%, 2%, 1%. 0.9%, 0.8%, 0.5%, 0.3% or 0.1% of the height of the walls of the sequestration pen or walls of the microfluidic device. While described in detail for the microfluidic device 200, this also applies to any of the microfluidic devices 100, 230, 250, 280, 290, 320, 400, 450, 500, 700 described herein.

The microfluidic channel 122 can thus be an example of a swept region, and the isolation regions 240 of the sequestration pens 224, 226, 228 can be examples of unswept regions. As noted, the microfluidic channel 122 and sequestration pens 224, 226, 228 can be configured to contain one or more fluidic media 180. In the example shown in FIGS. 2A-2B, the ports 222 are connected to the microfluidic channel 122 and allow a fluidic medium 180 to be introduced into or removed from the microfluidic device 230. Prior to introduction of the fluidic medium 180, the microfluidic device may be primed with a gas such as carbon dioxide gas. Once the microfluidic device 230 contains the fluidic medium 180, the flow 242 of fluidic medium 180 in the microfluidic channel 122 can be selectively generated and stopped. For example, as shown, the ports 222 can be disposed at different locations (e.g., opposite ends) of the microfluidic channel 122, and a flow 242 of medium can be created from one port 222 functioning as an inlet to another port 222 functioning as an outlet.

FIG. 2C illustrates a detailed view of an example of a sequestration pen 224 according to the present disclosure. Examples of micro-objects 246 are also shown.

As is known, a flow 242 of fluidic medium 180 in a microfluidic channel 122 past a proximal opening 234 of sequestration pen 224 can cause a secondary flow 244 of the medium 180 into and/or out of the sequestration pen 224. To isolate micro-objects 246 in the isolation region 240 of a sequestration pen 224 from the secondary flow 244, the length $L_{con}$ of the connection region 236 of the sequestration pen 224 (i.e., from the proximal opening 234 to the distal opening 238) should be greater than the penetration depth $D_p$ of the secondary flow 244 into the connection region 236. The penetration depth $D_p$ of the secondary flow 244 depends upon the velocity of the fluidic medium 180 flowing in the microfluidic channel 122 and various parameters relating to the configuration of the microfluidic channel 122 and the proximal opening 234 of the connection region 236 to the microfluidic channel 122. For a given microfluidic device, the configurations of the microfluidic channel 122 and the opening 234 will be fixed, whereas the rate of flow 242 of fluidic medium 180 in the microfluidic channel 122 will be variable. Accordingly, for each sequestration pen 224, a maximal velocity $V_{max}$ for the flow 242 of fluidic medium 180 in channel 122 can be identified that ensures that the penetration depth $D_p$ of the secondary flow 244 does not exceed the length $L_{con}$ of the connection region 236. As long as the rate of the flow 242 of fluidic medium 180 in the microfluidic channel 122 does not exceed the maximum velocity $V_{max}$, the resulting secondary flow 244 can be limited to the microfluidic channel 122 and the connection region 236 and kept out of the isolation region 240. The flow 242 of medium 180 in the microfluidic channel 122 will thus not draw micro-objects 246 out of the isolation region 240. Rather, micro-objects 246 located in the isolation region 240 will stay in the isolation region 240 regardless of the flow 242 of fluidic medium 180 in the microfluidic channel 122.

Moreover, as long as the rate of flow 242 of medium 180 in the microfluidic channel 122 does not exceed $V_{max}$, the flow 242 of fluidic medium 180 in the microfluidic channel 122 will not move miscellaneous particles (e.g., microparticles and/or nanoparticles) from the microfluidic channel 122 into the isolation region 240 of a sequestration pen 224. Having the length $L_{con}$ of the connection region 236 be greater than the maximum penetration depth $D_p$ of the secondary flow 244 can thus prevent contamination of one sequestration pen 224 with miscellaneous particles from the microfluidic channel 122 or another sequestration pen (e.g., sequestration pens 226, 228 in FIG. 2D).

Because the microfluidic channel 122 and the connection regions 236 of the sequestration pens 224, 226, 228 can be affected by the flow 242 of medium 180 in the microfluidic channel 122, the microfluidic channel 122 and connection regions 236 can be deemed swept (or flow) regions of the microfluidic device 230. The isolation regions 240 of the sequestration pens 224, 226, 228, on the other hand, can be deemed unswept (or non-flow) regions. For example, components (not shown) in a first fluidic medium 180 in the microfluidic channel 122 can mix with a second fluidic medium 248 in the isolation region 240 substantially only by diffusion of components of the first medium 180 from the microfluidic channel 122 through the connection region 236 and into the second fluidic medium 248 in the isolation region 240. Similarly, components (not shown) of the second medium 248 in the isolation region 240 can mix with the first medium 180 in the microfluidic channel 122 substantially only by diffusion of components of the second medium 248 from the isolation region 240 through the connection region 236 and into the first medium 180 in the microfluidic channel 122. In some embodiments, the extent of fluidic medium exchange between the isolation region of a sequestration pen and the flow region by diffusion is greater than about 90%, 91%, 92%, 93%, 94% 95%, 96%, 97%, 98%, or greater than about 99% of fluidic exchange. The first medium 180 can be the same medium or a different medium than the second medium 248. Moreover, the first medium 180 and the second medium 248 can start out being the same, then become different (e.g., through conditioning of the second medium 248 by one or more cells in the isolation region 240, or by changing the medium 180 flowing through the microfluidic channel 122).

The maximum penetration depth $D_p$ of the secondary flow 244 caused by the flow 242 of fluidic medium 180 in the microfluidic channel 122 can depend on a number of parameters, as mentioned above. Examples of such parameters include: the shape of the microfluidic channel 122 (e.g., the microfluidic channel can direct medium into the connection region 236, divert medium away from the connection region 236, or direct medium in a direction substantially perpendicular to the proximal opening 234 of the connection region 236 to the microfluidic channel 122); a width $W_{ch}$ (or cross-sectional area) of the microfluidic channel 122 at the proximal opening 234; and a width $W_{con}$ (or cross-sectional area) of the connection region 236 at the proximal opening 234; the velocity V of the flow 242 of fluidic medium 180 in the microfluidic channel 122; the viscosity of the first medium 180 and/or the second medium 248, or the like.

In some embodiments, the dimensions of the microfluidic channel 122 and sequestration pens 224, 226, 228 can be oriented as follows with respect to the vector of the flow 242 of fluidic medium 180 in the microfluidic channel 122: the microfluidic channel width $W_{ch}$ (or cross-sectional area of the microfluidic channel 122) can be substantially perpendicular to the flow 242 of medium 180; the width $W_{con}$ (or cross-sectional area) of the connection region 236 at opening 234 can be substantially parallel to the flow 242 of medium 180 in the microfluidic channel 122; and/or the length $L_{con}$ of the connection region can be substantially perpendicular to the flow 242 of medium 180 in the microfluidic channel 122. The foregoing are examples only, and the relative position of the microfluidic channel 122 and sequestration pens 224, 226, 228 can be in other orientations with respect to each other.

As illustrated in FIG. 2C, the width $W_{con}$ of the connection region 236 can be uniform from the proximal opening 234 to the distal opening 238. The width $W_{con}$ of the connection region 236 at the distal opening 238 can thus be in any of the ranges identified herein for the width $W_{con}$ of the connection region 236 at the proximal opening 234. Alternatively, the width $W_{con}$ of the connection region 236 at the distal opening 238 can be larger than the width $W_{con}$ of the connection region 236 at the proximal opening 234.

As illustrated in FIG. 2C, the width of the isolation region 240 at the distal opening 238 can be substantially the same as the width $W_{con}$ of the connection region 236 at the proximal opening 234. The width of the isolation region 240 at the distal opening 238 can thus be in any of the ranges identified herein for the width $W_{con}$ of the connection region 236 at the proximal opening 234. Alternatively, the width of the isolation region 240 at the distal opening 238 can be larger or smaller than the width $W_{con}$ of the connection region 236 at the proximal opening 234. Moreover, the distal opening 238 may be smaller than the proximal opening 234 and the width $W_{con}$ of the connection region 236 may be narrowed between the proximal opening 234 and distal opening 238. For example, the connection region 236 may be narrowed between the proximal opening and the distal opening, using a variety of different geometries (e.g. chamfering the connection region, beveling the connection region). Further, any part or subpart of the connection region 236 may be narrowed (e.g. a portion of the connection region adjacent to the proximal opening 234).

Figure 2D:
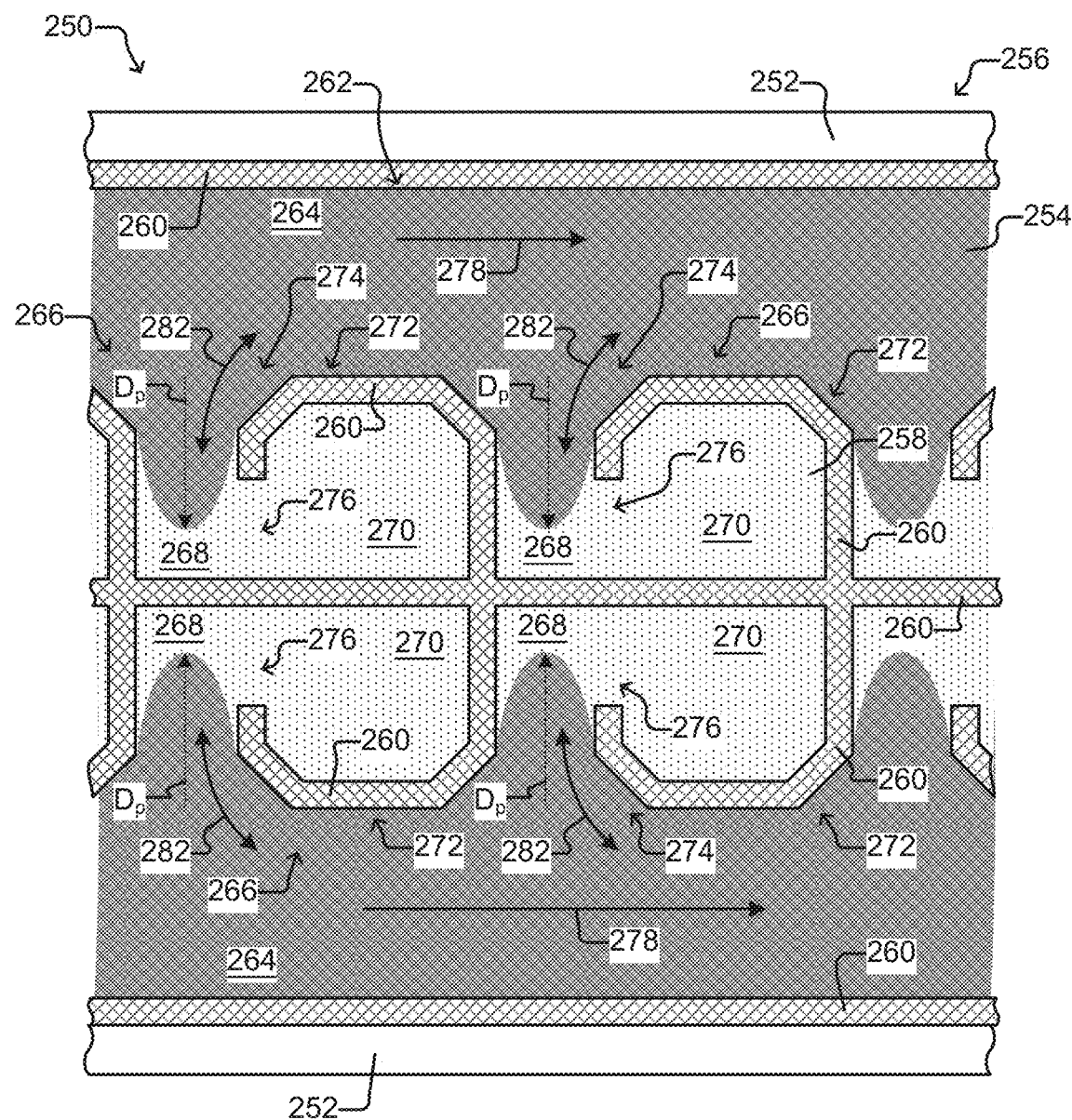
FIGS. 2D-F illustrate sequestration pens according to some other embodiments of the disclosure.
Figure 2E:
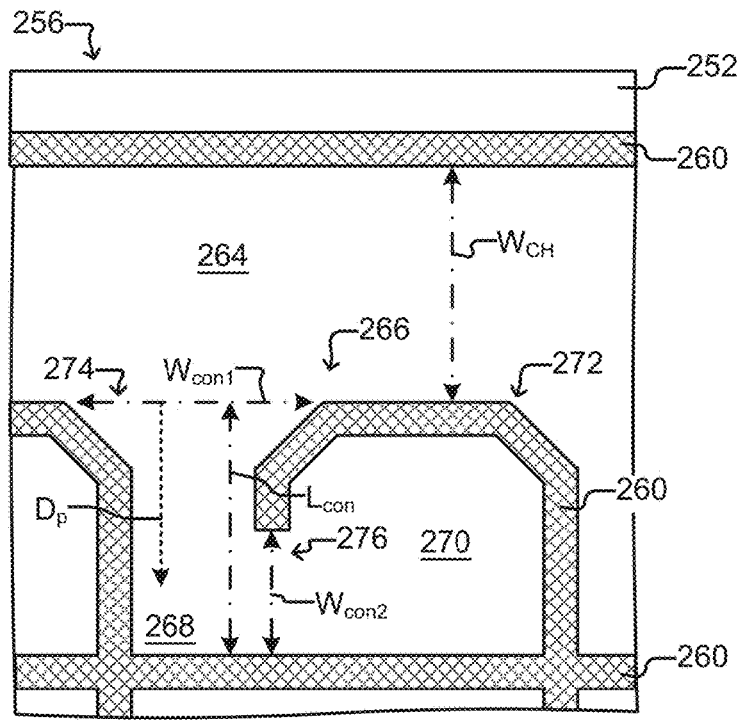
Figure 2F:
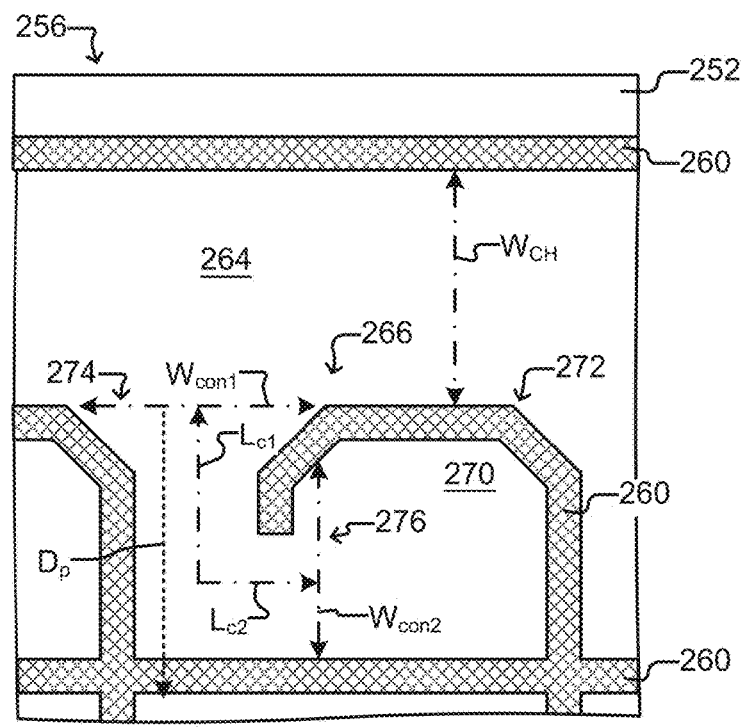

FIGS. 2D-2F depict another exemplary embodiment of a microfluidic device 250 containing a microfluidic circuit 262 and flow channels 264, which are variations of the respective microfluidic device 100, circuit 132 and channel 134 of FIG. 1A. The microfluidic device 250 also has a plurality of sequestration pens 266 that are additional variations of the above-described sequestration pens 124, 126, 128, 130, 224, 226 or 228. In particular, it should be appreciated that the sequestration pens 266 of device 250 shown in FIGS. 2D-2F can replace any of the above-described sequestration pens 124, 126, 128, 130, 224, 226 or 228 in devices 100, 200, 230, 280, 290, 320, 400, 450, 500, 700. Likewise, the microfluidic device 250 is another variant of the microfluidic device 100, and may also have the same or a different DEP configuration as the above-described microfluidic device 100, 200, 230, 280, 290, 320, 400, 450, 500, 700 as well as any of the other microfluidic system components described herein.

The microfluidic device 250 of FIGS. 2D-2F comprises a support structure (not visible in FIGS. 2D-2F, but can be the same or generally similar to the support structure 104 of device 100 depicted in FIG. 1A), a microfluidic circuit structure 256, and a cover (not visible in FIGS. 2D-2F, but can be the same or generally similar to the cover 122 of device 100 depicted in FIG. 1A). The microfluidic circuit structure 256 includes a frame 252 and microfluidic circuit material 260, which can be the same as or generally similar to the frame 114 and microfluidic circuit material 116 of device 100 shown in FIG. 1A. As shown in FIG. 2D, the microfluidic circuit 262 defined by the microfluidic circuit material 260 can comprise multiple channels 264 (two are shown but there can be more) to which multiple sequestration pens 266 are fluidically connected.

Each sequestration pen 266 can comprise an isolation structure 272, an isolation region 270 within the isolation structure 272, and a connection region 268. From a proximal opening 274 at the microfluidic channel 264 to a distal opening 276 at the isolation structure 272, the connection region 268 fluidically connects the microfluidic channel 264 to the isolation region 270. Generally, in accordance with the above discussion of FIGS. 2B and 2C, a flow 278 of a first fluidic medium 254 in a channel 264 can create secondary flows 282 of the first medium 254 from the microfluidic channel 264 into and/or out of the respective connection regions 268 of the sequestration pens 266.

As illustrated in FIG. 2E, the connection region 268 of each sequestration pen 266 generally includes the area extending between the proximal opening 274 to a channel 264 and the distal opening 276 to an isolation structure 272. The length $L_{con}$ of the connection region 268 can be greater than the maximum penetration depth $D_p$ of secondary flow 282, in which case the secondary flow 282 will extend into the connection region 268 without being redirected toward the isolation region 270 (as shown in FIG. 2D). Alternatively, at illustrated in FIG. 2F, the connection region 268 can have a length $L_{con}$ that is less than the maximum penetration depth $D_p$, in which case the secondary flow 282 will extend through the connection region 268 and be redirected toward the isolation region 270. In this latter situation, the sum of lengths $L_{c1}$ and $L_{c2}$ of connection region 268 is greater than the maximum penetration depth $D_p$, so that secondary flow 282 will not extend into isolation region 270. Whether length $L_{con}$ of connection region 268 is greater than the penetration depth $D_p$, or the sum of lengths $L_{c1}$ and $L_{c2}$ of connection region 268 is greater than the penetration depth $D_p$, a flow 278 of a first medium 254 in channel 264 that does not exceed a maximum velocity $V_{max}$ will produce a secondary flow having a penetration depth $D_p$, and micro-objects (not shown but can be the same or generally similar to the micro-objects 246 shown in FIG. 2C) in the isolation region 270 of a sequestration pen 266 will not be drawn out of the isolation region 270 by a flow 278 of first medium 254 in channel 264. Nor will the flow 278 in channel 264 draw miscellaneous materials (not shown) from channel 264 into the isolation region 270 of a sequestration pen 266. As such, diffusion is the only mechanism by which components in a first medium 254 in the microfluidic channel 264 can move from the microfluidic channel 264 into a second medium 258 in an isolation region 270 of a sequestration pen 266. Likewise, diffusion is the only mechanism by which components in a second medium 258 in an isolation region 270 of a sequestration pen 266 can move from the isolation region 270 to a first medium 254 in the microfluidic channel 264. The first medium 254 can be the same medium as the second medium 258, or the first medium 254 can be a different medium than the second medium 258. Alternatively, the first medium 254 and the second medium 258 can start out being the same, then become different, e.g., through conditioning of the second medium by one or more cells in the isolation region 270, or by changing the medium flowing through the microfluidic channel 264.

As illustrated in FIG. 2E, the width $W_{ch}$ of the microfluidic channels 264 (i.e., taken transverse to the direction of a fluid medium flow through the microfluidic channel indicated by arrows 278 in FIG. 2D) in the microfluidic channel 264 can be substantially perpendicular to a width $W_{con1}$ of the proximal opening 274 and thus substantially parallel to a width $W_{con2}$ of the distal opening 276. The width $W_{con1}$ of the proximal opening 274 and the width $W_{con2}$ of the distal opening 276, however, need not be substantially perpendicular to each other. For example, an angle between an axis (not shown) on which the width $W_{con1}$ of the proximal opening 274 is oriented and another axis on which the width $W_{con2}$ of the distal opening 276 is oriented can be other than perpendicular and thus other than 90°. Examples of alternatively oriented angles include angles in any of the following ranges: from about 30° to about 90°, from about 45° to about 90°, from about 60° to about 90°, or the like.

In various embodiments of sequestration pens (e.g. 124, 126, 128, 130, 224, 226, 228, or 266), the isolation region (e.g. 240 or 270) is configured to contain a plurality of micro-objects. In other embodiments, the isolation region can be configured to contain only one, two, three, four, five, or a similar relatively small number of micro-objects. Accordingly, the volume of an isolation region can be, for example, at least $1 \times 10^6$, $2 \times 10^6$, $4 \times 10^6$, $6 \times 10^6$ cubic microns, or more.

In various embodiments of sequestration pens, the width $W_{ch}$ of the microfluidic channel (e.g., 122) at a proximal opening (e.g. 234) can be within any of the following ranges: about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. In some other embodiments, the width $W_{ch}$ of the microfluidic channel (e.g., 122) at a proximal opening (e.g. 234) can be in a range of about 200-800 microns, 200-700 microns, or 200-600 microns. The foregoing are examples only, and the width $W_{ch}$ of the microfluidic channel 122 can be in other ranges (e.g., a range defined by any of the endpoints listed above). Moreover, the $W_{ch}$ of the microfluidic channel 122 can be selected to be in any of these ranges in regions of the microfluidic channel other than at a proximal opening of a sequestration pen.

In some embodiments, a sequestration pen has a height of about 30 to about 200 microns, or about 50 to about 150 microns. In some embodiments, the sequestration pen has a cross-sectional area of about $1 \times 10^4$-$3 \times 10^6$ square microns, $2 \times 10^4$-$2 \times 10^6$ square microns, $4 \times 10^4$-$1 \times 10^6$ square microns, $2 \times 10^4$-$5 \times 10^5$ square microns, $2 \times 10^4$-$1 \times 10^5$ square microns or about $2 \times 10^5$-$2 \times 10^6$ square microns.

In various embodiments of sequestration pens, the height $H_{ch}$ of the microfluidic channel (e.g., 122) at a proximal opening (e.g., 234) can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the microfluidic channel (e.g., 122) can be in other ranges (e.g., a range defined by any of the endpoints listed above). The height $H_{ch}$ of the microfluidic channel 122 can be selected to be in any of these ranges in regions of the microfluidic channel other than at a proximal opening of an sequestration pen.

In various embodiments of sequestration pens a cross-sectional area of the microfluidic channel (e.g., 122) at a proximal opening (e.g., 234) can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel (e.g., 122) at a proximal opening (e.g., 234) can be in other ranges (e.g., a range defined by any of the endpoints listed above).

In various embodiments of sequestration pens, the length $L_{con}$ of the connection region (e.g., 236) can be in any of the following ranges: about 1-600 microns, 5-550 microns, 10-500 microns, 15-400 microns, 20-300 microns, 20-500 microns, 40-400 microns, 60-300 microns, 80-200 microns, or about 100-150 microns. The foregoing are examples only, and length $L_{con}$ of a connection region (e.g., 236) can be in a different range than the foregoing examples (e.g., a range defined by any of the endpoints listed above).

In various embodiments of sequestration pens the width $W_{con}$ of a connection region (e.g., 236) at a proximal opening (e.g., 234) can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region (e.g., 236) at a proximal opening (e.g., 234) can be different than the foregoing examples (e.g., a range defined by any of the endpoints listed above).

In various embodiments of sequestration pens, the width $W_{con}$ of a connection region (e.g., 236) at a proximal opening (e.g., 234) can be at least as large as the largest dimension of a micro-object (e.g., a biological cell, such as a mammalian cell, an immunological cell, a stem cell, or the like) that the sequestration pen is intended for. For example, the width $W_{con}$ of a connection region 236 at a proximal opening 234 of a sequestration pen that a mammalian cell will be placed into can be in any of the following ranges: about 20 to about 100 microns, about 30 to about 90 microns, about 40 to about 80 microns, about 50 to about 70 microns, or about 60 microns. The foregoing are examples only, and the width $W_{con}$ of a connection region (e.g., 236) at a proximal opening (e.g., 234) can be different than the foregoing examples (e.g., within a range defined by any of the endpoints listed above).

In various embodiments of sequestration pens, a ratio of the length $L_{con}$ of a connection region (e.g., 236) to a width $W_{con}$ of the connection region (e.g., 236) at the proximal opening 234 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 236 to a width $W_{con}$ of the connection region 236 at the proximal opening 234 can be different than the foregoing examples.

In various embodiments of microfluidic devices 100, 200, 23, 250, 280, 290, 320, 400, 450, 500, 700, $V_{max}$ can be set around 0.2, 0.3, 0.4, 0.5, 0.6, 0.7, 0.8, 0.9, 1.0, 1.1, 1.2, 1.3, 1.4, or 1.5.

In various embodiments of microfluidic devices having sequestration pens, the volume of an isolation region (e.g., 240) of a sequestration pen can be, for example, at least $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1.0 \times 10^6$, $1.1 \times 10^6$, $1.2 \times 10^6$, $1.3 \times 10^6$, $1.4 \times 10^6$, $1.5 \times 10^7$, $1.6 \times 10^7$, $1.7 \times 10^7$, $1.8 \times 10^7$, $1.9 \times 10^7$, $2.0 \times 10^7$ cubic microns, or more. In some embodiments, the volume of an isolation region of a sequestration pen can be within a range defined by any two of the foregoing endpoints (e.g., between about $3 \times 10^5$ and about $1 \times 10^6$ cubic microns, between about $8 \times 10^5$ and about $1.5 \times 10^6$ cubic microns, or between about $1.3 \times 10^6$ and $2.0 \times 10^6$ cubic microns). In various embodiments, the volume of a sequestration pen may be about $3 \times 10^5$, $4 \times 10^5$, $5 \times 10^5$, $6 \times 10^5$, $7 \times 10^5$, $8 \times 10^5$, $9 \times 10^5$, $1 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, $2.0 \times 10^6$, $2.5 \times 10^6$, $3.0 \times 10^6$, $3.5 \times 10^7$, $4.0 \times 10^7$, $4.5 \times 10^7$, or about $5.0 \times 10^7$ cubic microns, or more. In some embodiments, the volume of a sequestration pen can be within a range defined by any two of the foregoing endpoints (e.g., between about $5 \times 10^5$ and about $1 \times 10^6$ cubic microns, between about $1 \times 10^6$ and about $1.5 \times 10^6$ cubic microns, or between about $1.5 \times 10^6$ and $2.0 \times 10^6$ cubic microns). In some embodiments, the volume of a sequestration pen may be about 250 picoliters to about 5 nanoliters, about 500 picoliters to about 1 nanoliter, about 1 nanoliter to about 1.5 nanoliters, about 1.5 nanoliters to about 2.0 nanoliters, about 2.0 nanoliters to about 2.5 nanoliters, about 2.5 nanoliters to about 3.0 nanoliters, about 3.0 nanoliters to about 3.5 nanoliters, or any range defined by two of the foregoing endpoints.

In various embodiment, the microfluidic device has sequestration pens configured as in any of the embodiments discussed herein where the microfluidic device has about 5 to about 10 sequestration pens, about 10 to about 50 sequestration pens, about 100 to about 500 sequestration pens; about 200 to about 1000 sequestration pens, about 500 to about 1500 sequestration pens, about 1000 to about 2000 sequestration pens, or about 1000 to about 3500 sequestration pens. The sequestration pens need not all be the same size and may include a variety of configurations (e.g., different widths, different features within the sequestration pen.

Figure 2G:
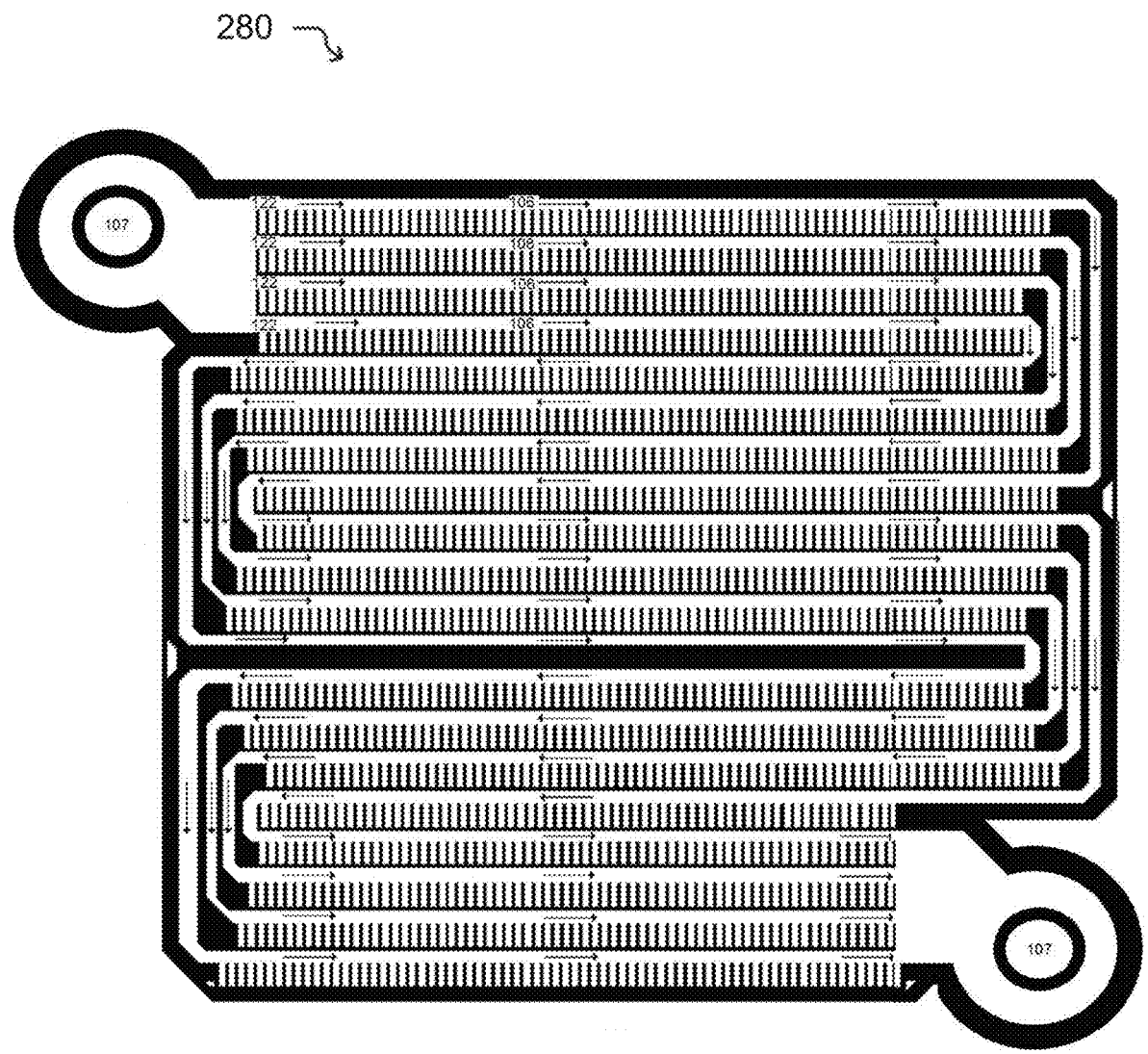
FIG. 2G illustrates a microfluidic device according to an embodiment of the disclosure.

FIG. 2G illustrates a microfluidic device 280 according to one embodiment. The microfluidic device 280 is illustrated in FIG. 2G is a stylized diagram of a microfluidic device 100. In practice the microfluidic device 280 and its constituent circuit elements (e.g. channels 122 and sequestration pens 128) would have the dimensions discussed herein. The microfluidic circuit 120 illustrated in FIG. 2G has two ports 107, four distinct channels 122 and four distinct flow paths 106. The microfluidic device 280 further comprises a plurality of sequestration pens opening off of each channel 122. In the microfluidic device illustrated in FIG. 2G, the sequestration pens have a geometry similar to the pens illustrated in FIG. 2C and thus, have both connection regions and isolation regions. Accordingly, the microfluidic circuit 120 includes both swept regions (e.g. channels 122 and portions of the connection regions 236 within the maximum penetration depth $D_p$ of the secondary flow 244) and non-swept regions (e.g. isolation regions 240 and portions of the connection regions 236 not within the maximum penetration depth $D_p$ of the secondary flow 244).

Figure 3A:
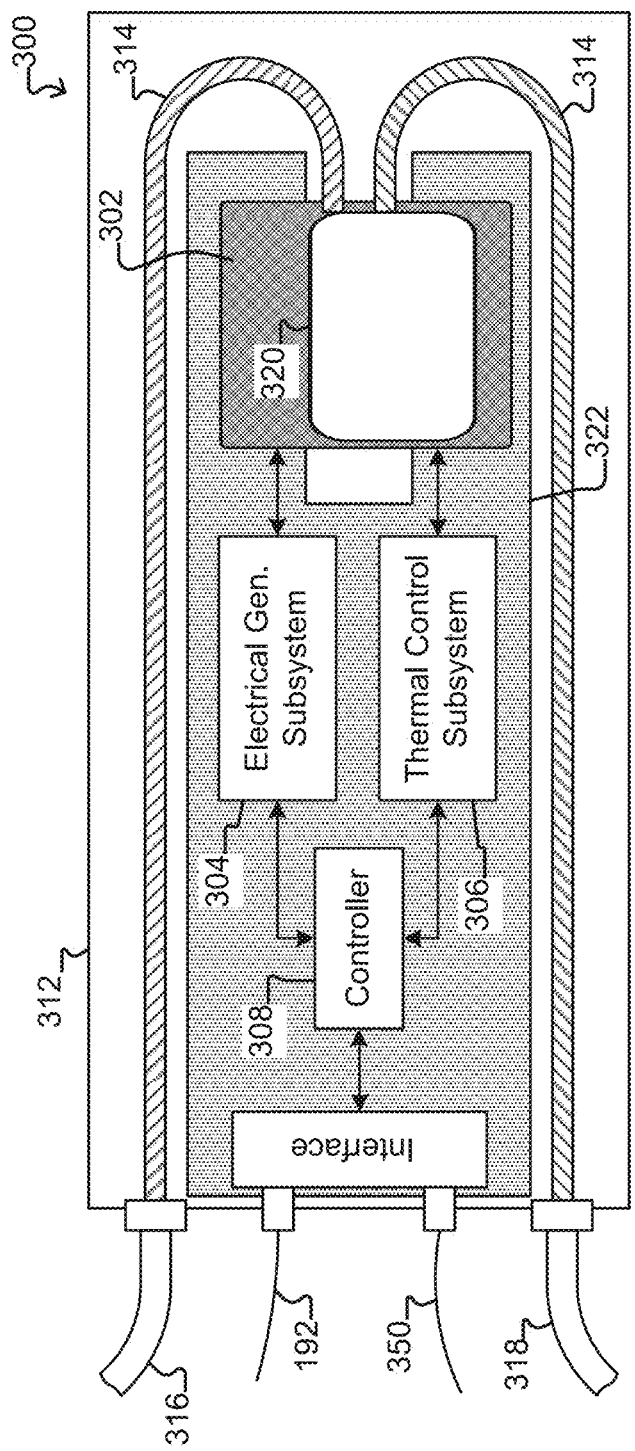
FIG. 3A illustrates a specific example of a system for use with a microfluidic device and associated control equipment according to some embodiments of the disclosure.
Figure 3B:
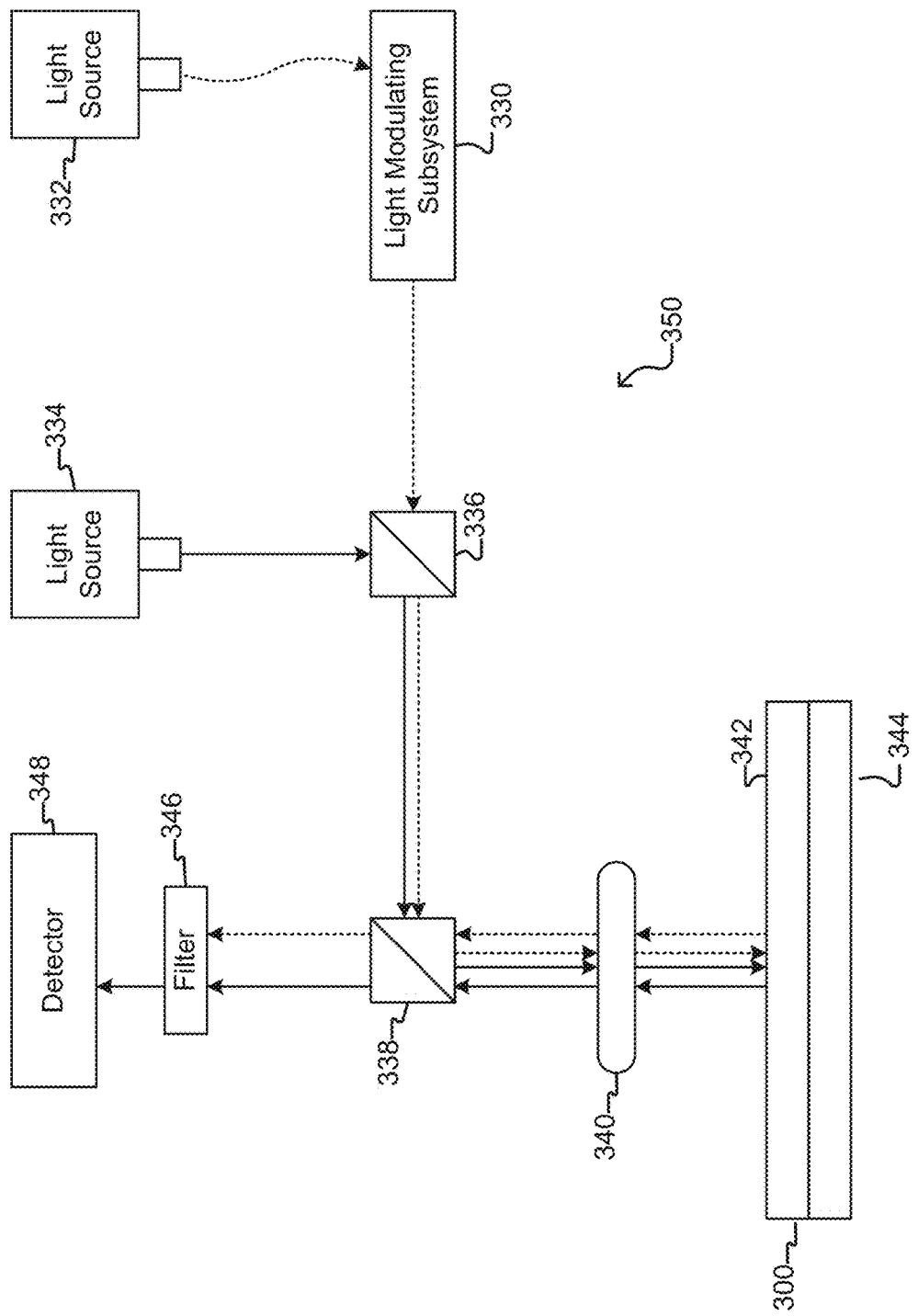
FIG. 3B illustrates an imaging device according to some embodiments of the disclosure.

FIGS. 3A through 3B shows various embodiments of system 150 which can be used to operate and observe microfluidic devices (e.g. 100, 200, 230, 250, 280, 290, 320, 400, 450, 500, 700) according to the present disclosure. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 320 (e.g., an optically-actuated electrokinetic device 100) and providing electrical connections from power source 192 to microfluidic device 320. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 320 when it is being held by socket 302. Thus, the electrical signal generation subsystem 304 can be part of power source 192. The ability to apply a biasing voltage to microfluidic device 320 does not mean that a biasing voltage will be applied at all times when the microfluidic device 320 is held by the socket 302. Rather, in most cases, the biasing voltage will be applied intermittently, e.g., only as needed to facilitate the generation of electrokinetic forces, such as dielectrophoresis or electro-wetting, in the microfluidic device 320.

As illustrated in FIG. 3A, the nest 300 can include a printed circuit board assembly (PCBA) 322. The electrical signal generation subsystem 304 can be mounted on and electrically integrated into the PCBA 322. The exemplary support includes socket 302 mounted on PCBA 322, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 320 held by the socket 302. In certain embodiments, the oscilloscope measures the waveform at a location proximal to the microfluidic device 320 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1A) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 320 and then adjust its own output voltage as needed such that the measured voltage at the microfluidic device 320 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 100.

As illustrated in FIG. 3A, the support structure 300 (e.g., nest) can further include a thermal control subsystem 306. The thermal control subsystem 306 can be configured to regulate the temperature of microfluidic device 320 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 320. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 314 configured to circulate cooled fluid through the cooling block. In the embodiment illustrated in FIG. 3A, the support structure 300 comprises an inlet 316 and an outlet 318 to receive cooled fluid from an external reservoir (not shown), introduce the cooled fluid into the fluidic path 314 and through the cooling block, and then return the cooled fluid to the external reservoir. In some embodiments, the Peltier thermoelectric device, the cooling unit, and/or the fluidic path 314 can be mounted on a casing 312 of the support structure 300. In some embodiments, the thermal control subsystem 306 is configured to regulate the temperature of the Peltier thermoelectric device so as to achieve a target temperature for the microfluidic device 320. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient+/−0.02 ppm/CO) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 324 which allows the microprocessor of the controller 308 to communicate with an external master controller 154 via the interface 310 (not shown). In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 324, the electrical signal generation subsystem 304 and the thermal control subsystem 306 can communicate with the external master controller 154. In this manner, the master controller 154 can, among other things, assist the electrical signal generation subsystem 304 by performing scaling calculations for output voltage adjustments. A Graphical User Interface (GUI) (not shown) provided via a display device 170 coupled to the external master controller 154, can be configured to plot temperature and waveform data obtained from the thermal control subsystem 306 and the electrical signal generation subsystem 304, respectively. Alternatively, or in addition, the GUI can allow for updates to the controller 308, the thermal control subsystem 306, and the electrical signal generation subsystem 304.

As discussed above, system 150 can include an imaging device. In some embodiments, the imaging device comprises a light modulating subsystem 330 (See FIG. 3B). The light modulating subsystem 330 can include a digital mirror device (DMD) or a microshutter array system (MSA), either of which can be configured to receive light from a light source 332 and transmits a subset of the received light into an optical train of microscope 350. Alternatively, the light modulating subsystem 330 can include a device that produces its own light (and thus dispenses with the need for a light source 332), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 330 can be, for example, a projector. Thus, the light modulating subsystem 330 can be capable of emitting both structured and unstructured light. In certain embodiments, imaging module 164 and/or motive module 162 of system 150 can control the light modulating subsystem 330.

In certain embodiments, the imaging device further comprises a microscope 350. In such embodiments, the nest 300 and light modulating subsystem 330 can be individually configured to be mounted on the microscope 350. The microscope 350 can be, for example, a standard research-grade light microscope or fluorescence microscope. Thus, the nest 300 can be configured to be mounted on the stage 344 of the microscope 350 and/or the light modulating subsystem 330 can be configured to mount on a port of microscope 350. In other embodiments, the nest 300 and the light modulating subsystem 330 described herein can be integral components of microscope 350.

In certain embodiments, the microscope 350 can further include one or more detectors 348. In some embodiments, the detector 348 is controlled by the imaging module 164. The detector 348 can include an eye piece, a charge-coupled device (CCD), a camera (e.g., a digital camera), or any combination thereof. If at least two detectors 348 are present, one detector can be, for example, a fast-frame-rate camera while the other detector can be a high sensitivity camera. Furthermore, the microscope 350 can include an optical train configured to receive reflected and/or emitted light from the microfluidic device 320 and focus at least a portion of the reflected and/or emitted light on the one or more detectors 348. The optical train of the microscope can also include different tube lenses (not shown) for the different detectors, such that the final magnification on each detector can be different.

In certain embodiments, the imaging device is configured to use at least two light sources. For example, a first light source 332 can be used to produce structured light (e.g., via the light modulating subsystem 330) and a second light source 334 can be used to provide unstructured light. The first light source 332 can produce structured light for optically-actuated electrokinesis and/or fluorescent excitation, and the second light source 334 can be used to provide bright field illumination. In these embodiments, the motive module 164 can be used to control the first light source 332 and the imaging module 164 can be used to control the second light source 334. The optical train of the microscope 350 can be configured to (1) receive structured light from the light modulating subsystem 330 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 348. The optical train can be further configured to receive unstructured light from a second light source and focus the unstructured light on at least a second region of the microfluidic device, when the device is held by the nest 300. In certain embodiments, the first and second regions of the microfluidic device can be overlapping regions.

In FIG. 3B, the first light source 332 is shown supplying light to a light modulating subsystem 330, which provides structured light to the optical train of the microscope 350 of system 355 (not shown). The second light source 334 is shown providing unstructured light to the optical train via a beam splitter 336. Structured light from the light modulating subsystem 330 and unstructured light from the second light source 334 travel from the beam splitter 336 through the optical train together to reach a second beam splitter (or dichroic filter 338, depending on the light provided by the light modulating subsystem 330), where the light gets reflected down through the objective 336 to the sample plane 342. Reflected and/or emitted light from the sample plane 342 then travels back up through the objective 340, through the beam splitter and/or dichroic filter 338, and to a dichroic filter 346. Only a fraction of the light reaching dichroic filter 346 passes through and reaches the detector 348.

In some embodiments, the second light source 334 emits blue light. With an appropriate dichroic filter 346, blue light reflected from the sample plane 342 is able to pass through dichroic filter 346 and reach the detector 348. In contrast, structured light coming from the light modulating subsystem 330 gets reflected from the sample plane 342, but does not pass through the dichroic filter 346. In this example, the dichroic filter 346 is filtering out visible light having a wavelength longer than 495 nm. Such filtering out of the light from the light modulating subsystem 330 would only be complete (as shown) if the light emitted from the light modulating subsystem did not include any wavelengths shorter than 495 nm. In practice, if the light coming from the light modulating subsystem 330 includes wavelengths shorter than 495 nm (e.g., blue wavelengths), then some of the light from the light modulating subsystem would pass through filter 346 to reach the detector 348. In such an embodiment, the filter 346 acts to change the balance between the amount of light that reaches the detector 348 from the first light source 332 and the second light source 334. This can be beneficial if the first light source 332 is significantly stronger than the second light source 334. In other embodiments, the second light source 334 can emit red light, and the dichroic filter 346 can filter out visible light other than red light (e.g., visible light having a wavelength shorter than 650 nm).

Coating solutions and coating agents.

Without intending to be limited by theory, maintenance of a biological micro-object (e.g., a biological cell) within a microfluidic device (e.g., a DEP-configured and/or EW-configured microfluidic device) may be facilitated (i.e., the biological micro-object exhibits increased viability, greater expansion and/or greater portability within the microfluidic device) when at least one or more inner surfaces of the microfluidic device have been conditioned or coated so as to present a layer of organic and/or hydrophilic molecules that provides the primary interface between the microfluidic device and biological micro-object(s) maintained therein. In some embodiments, one or more of the inner surfaces of the microfluidic device (e.g. the inner surface of the electrode activation substrate of a DEP-configured microfluidic device, the cover of the microfluidic device, and/or the surfaces of the circuit material) may be treated with or modified by a coating solution and/or coating agent to generate the desired layer of organic and/or hydrophilic molecules.

The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a DEP-configured microfluidic device) are treated or "primed" with a coating solution comprising a coating agent prior to introduction of the biological micro-object(s) into the microfluidic device.

In some embodiments, at least one surface of the microfluidic device includes a coating material that provides a layer of organic and/or hydrophilic molecules suitable for maintenance and/or expansion of biological micro-object(s) (e.g. provides a conditioned surface as described below). In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

Coating Agent/Solution.

Any convenient coating agent/coating solution can be used, including but not limited to: serum or serum factors, bovine serum albumin (BSA), polymers, detergents, enzymes, and any combination thereof.

Polymer-Based Coating Materials.

The at least one inner surface may include a coating material that comprises a polymer. The polymer may be covalently or non-covalently bound (or may be non-specifically adhered) to the at least one surface. The polymer may have a variety of structural motifs, such as found in block polymers (and copolymers), star polymers (star copolymers), and graft or comb polymers (graft copolymers), any of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers may range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the coating material may include a polymer containing carboxylic acid moieties. The carboxylic acid subunit may be an alkyl, alkenyl or aromatic moiety containing subunit. One non-limiting example is polylactic acid (PLA). In other embodiments, the coating material may include a polymer containing phosphate moieties, either at a terminus of the polymer backbone or pendant from the backbone of the polymer. In yet other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. In further embodiments, the coating material may include a polymer including amine moieties. The polyamino polymer may include a natural polyamine polymer or a synthetic polyamine polymer. Examples of natural polyamines include spermine, spermidine, and putrescine.

In other embodiments, the coating material may include a polymer containing saccharide moieties. In a non-limiting example, polysaccharides such as xanthan gum or dextran may be suitable to form a material which may reduce or prevent cell sticking in the microfluidic device. For example, a dextran polymer having a size about 3 kDa may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties, providing a polyelectrolyte surface. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA) and/or serum (or a combination of multiple different sera) comprising albumin and/or one or more other similar proteins as coating agents. The serum can be from any convenient source, including but not limited to fetal calf serum, sheep serum, goat serum, horse serum, and the like. In certain embodiments, BSA in a coating solution is present in a range of form about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more, or anywhere in between. In certain embodiments, serum in a coating solution may be present in a range of from about 20% (v/v) to about 50% v/v, including 25%, 30%, 35%, 40%, 45%, or more or anywhere in between. In some embodiments, BSA may be present as a coating agent in a coating solution at: 5 mg/mL, whereas in other embodiments, BSA may be present as a coating agent in a coating solution at 70 mg/mL. In certain embodiments, serum is present as a coating agent in a coating solution at 30%. In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer-coated surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently Linked Coating Materials.

In some embodiments, the at least one inner surface includes covalently linked molecules that provide a layer of organic and/or hydrophilic molecules suitable for maintenance/expansion of biological micro-object(s) within the microfluidic device, providing a conditioned surface for such cells.

The covalently linked molecules include a linking group, wherein the linking group is covalently linked to one or more surfaces of the microfluidic device, as described below. The linking group is also covalently linked to a moiety configured to provide a layer of organic and/or hydrophilic molecules suitable for maintenance/expansion of biological micro-object(s).

In some embodiments, the covalently linked moiety configured to provide a layer of organic and/or hydrophilic molecules suitable for maintenance/expansion of biological micro-object(s) may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments, the covalently linked moiety configured to provide a layer of organic and/or hydrophilic molecules suitable for maintenance/expansion of biological micro-object(s) in the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety. Alternatively, the covalently linked moiety may include polymeric moieties, which may be any of the moieties described above.

In some embodiments, the covalently linked alkyl moiety may comprises carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

In other embodiments, the covalently linked moiety may include at least one alkylene oxide moiety, and may include any alkylene oxide polymer as described above. One useful class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the sequestration pens and/or flow regions (e.g., channels).

The coating material providing a conditioned surface may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having charged moieties covalently attached to an alkyl or fluoroalkyl chain having a greater number of methylene or fluoromethylene units, which may provide capacity to present bulkier moieties at the coated surface. In this instance, the first set of molecules having different, less sterically demanding termini and fewer backbone atoms can help to functionalize the entire substrate surface and thereby prevent undesired adhesion or contact with the silicon/silicon oxide, hafnium oxide or alumina making up the substrate itself. In another example, the covalently linked moieties may provide a zwitterionic surface presenting alternating charges in a random fashion on the surface.

Conditioned surface properties.

Aside from the composition of the conditioned surface, other factors such as physical thickness of the coating material can impact DEP force. Various factors can alter the physical thickness of the coating material, such as the manner in which the coating material is deposited or reacted with the substrate (e.g. vapor deposition, liquid phase deposition, spin coating, flooding, and electrostatic coating). In some embodiments, the conditioned surface has a thickness of less than 10 nm (e.g., in the range of about 1 nm to about 10 nm, about 1 nm to about 7 nm, about 1 nm to about 5 nm, or any individual value therebetween). In other embodiments, the conditioned surface formed by the covalently linked moieties may have a thickness of about 10 nm to about 50 nm. In some embodiments, the covalently linked moieties of the conditioned surface may form a monolayer when covalently linked to the surface of the microfluidic device (e.g., a DEP configured substrate surface) and may have a thickness of less than 10 nm (e.g., less than 5 nm, or about 1.5 to 3.0 nm). Typically, the conditioned surface does not require a perfectly formed monolayer to be suitably functional for operation within a DEP-configured microfluidic device.

The conditioned surface may also have properties that are beneficial in use with biological molecules. For example, a conditioned surface that contains fluorinated (or perfluorinated) carbon chains may reduce the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Unitary or Multi-Part Conditioned Surface.

The covalently linked coating material may be formed by reaction of a molecule which already contains the moiety configured to provide a layer of organic and/or hydrophilic molecules suitable for maintenance/expansion of biological micro-object(s) in the microfluidic device, as is described below. Alternatively, the covalently linked coating material may be formed in a two-part sequence by coupling the moiety configured to provide a layer of organic and/or hydrophilic molecules suitable for maintenance/expansion of biological micro-object(s) to a surface modifying ligand that itself has been covalently linked to the surface.

Methods of Preparing a Covalently Linked Coating Material.

In some embodiments, a coating material that is covalently linked to the surface of a microfluidic device (e.g., including at least one surface of the sequestration pens and/or flow regions) has a structure of Formula 1 or Formula 2. When the coating material is introduced to the surface in one step, it has a structure of Formula 1, while when the coating material is introduced in a multiple step process, it has a structure of Formula 2.

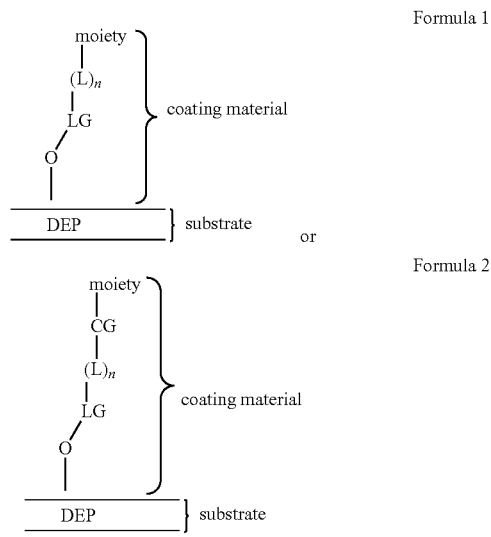

The coating material may be linked covalently to oxides of the surface of a DEP-configured or EW-configured substrate. The DEP- or EW-configured substrate may comprise silicon, silicon oxide, alumina, or hafnium oxide. Oxides may be present as part of the native chemical structure of the substrate or may be introduced as discussed below.

The coating material may be attached to the oxides via a linking group ("LG"), which may be a siloxy or phosphonate ester group formed from the reaction of a siloxane or phosphonic acid group with the oxides. The moiety configured to provide a layer of organic and/or hydrophilic molecules suitable for maintenance/expansion of biological micro-object(s) in the microfluidic device can be any of the moieties described herein. The linking group LG may be directly or indirectly connected to the moiety configured to provide a layer of organic and/or hydrophilic molecules suitable for maintenance/expansion of biological micro-object(s) in the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and phosphorus atoms, subject to chemical bonding limitations as is known in the art. It may be interrupted with any combination of one or more moieties chose from ether, amino, carbonyl, amido, or phosphonate groups, arylene, heteroarylene, and heterocyclic groups. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms.

In some embodiments, the moiety configured to provide a layer of organic and/or hydrophilic molecules suitable for maintenance/expansion of biological micro-object(s) may be added to the surface of the substrate in a multi-step process, and has a structure of Formula 2, as shown above. The moiety may be any of the moieties described above.

In some embodiments, the coupling group CG represents the resultant group from reaction of a reactive moiety $R_x$ and a reactive pairing moiety $R_{px}$ (i.e., a moiety configured to react with the reactive moiety $R_x$). For example, one typical coupling group CG may include a carboxamidyl group, which is the result of the reaction of an amino group with a derivative of a carboxylic acid, such as an activated ester, an acid chloride or the like. Other CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end (i.e., the end proximal to the moiety configured to provide a layer of organic and/or hydrophilic molecules suitable for maintenance/expansion of biological micro-object(s) in the microfluidic device) of linker L, which may include any combination of elements as described above. In some other embodiments, the coupling group CG may interrupt the backbone of the linker L. When the coupling group CG is triazolylene, it may be the product resulting from a Click coupling reaction and may be further substituted (e.g., a dibenzocylcooctenyl fused triazolylene group).

In some embodiments, the coating material (or surface modifying ligand) is deposited on the inner surfaces of the microfluidic device using chemical vapor deposition. The vapor deposition process can be optionally improved, for example, by pre-cleaning the cover 110, the microfluidic circuit material 116, and/or the substrate (e.g., the inner surface 208 of the electrode activation substrate 206 of a DEP-configured substrate, or a dielectric layer of the support structure 104 of an EW-configured substrate), by exposure to a solvent bath, sonication or a combination thereof. Alternatively, or in addition, such pre-cleaning can include treating the cover 110, the microfluidic circuit material 116, and/or the substrate in an oxygen plasma cleaner, which can remove various impurities, while at the same time introducing an oxidized surface (e.g. oxides at the surface, which may be covalently modified as described herein). Alternatively, liquid-phase treatments, such as a mixture of hydrochloric acid and hydrogen peroxide or a mixture of sulfuric acid and hydrogen peroxide (e.g., piranha solution, which may have a ratio of sulfuric acid to hydrogen peroxide in a range from about 3:1 to about 7:1) may be used in place of an oxygen plasma cleaner.

In some embodiments, vapor deposition is used to coat the inner surfaces of the microfluidic device 200 after the microfluidic device 200 has been assembled to form an enclosure 102 defining a microfluidic circuit 120. Without intending to be limited by theory, depositing such a coating material on a fully-assembled microfluidic circuit 120 may be beneficial in preventing delamination caused by a weakened bond between the microfluidic circuit material 116 and the electrode activation substrate 206 dielectric layer and/or the cover 110. In embodiments where a two-step process is employed the surface modifying ligand may be introduced via vapor deposition as described above, with subsequent introduction of the moiety configured provide a layer of organic and/or hydrophilic molecules suitable for maintenance/expansion of biological micro-object(s). The subsequent reaction may be performed by exposing the surface modified microfluidic device to a suitable coupling reagent in solution.

Figure 2H:
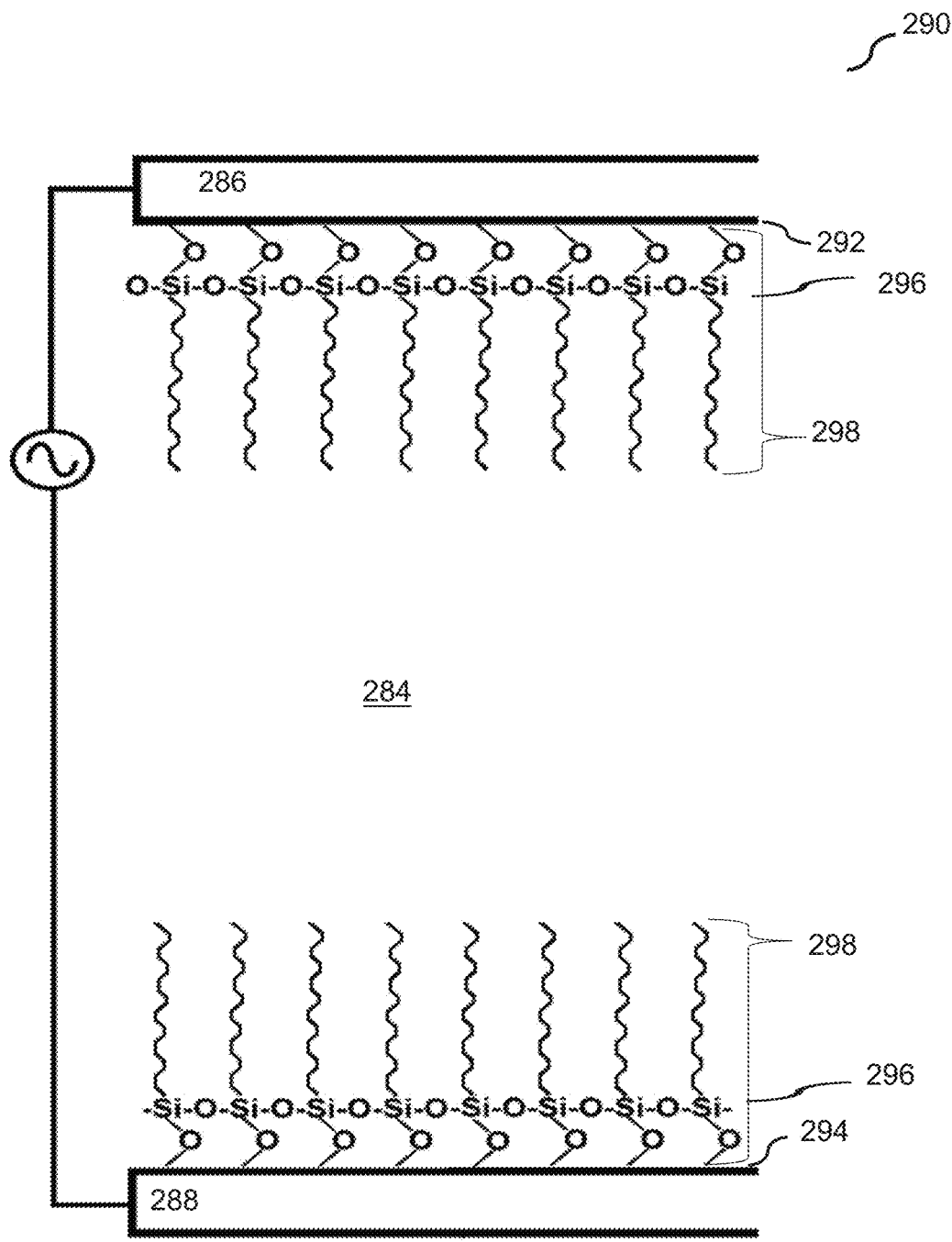
FIG. 2H illustrates a conditioned surface of a microfluidic device according to an embodiment of the disclosure.

FIG. 2H depicts a cross-sectional view of a microfluidic device 290 having an exemplary covalently linked coating material providing a conditioned surface. As illustrated, the coating materials 298 (shown schematically) can comprise a monolayer of densely-packed molecules covalently bound to both the inner surface 294 of a base 286, which may be a DEP substrate, and the inner surface 292 of a cover 288 of the microfluidic device 290. The coating material 298 can be disposed on substantially all inner surfaces 294, 292 proximal to, and facing inwards towards, the enclosure 284 of the microfluidic device 290, including, in some embodiments and as discussed above, the surfaces of microfluidic circuit material (not shown) used to define circuit elements and/or structures within the microfluidic device 290. In alternate embodiments, the coating material 298 can be disposed on only one or some of the inner surfaces of the microfluidic device 290.

In the embodiment shown in FIG. 2H, the coating material 298 can include a monolayer of organosiloxane molecules, each molecule covalently bonded to the inner surfaces 292, 294 of the microfluidic device 290 via a siloxy linker 296. Any of the above-discussed coating materials 298 can be used (e.g. an alkyl-terminated, a fluoroalkyl terminated moiety, a PEG-terminated moiety, a dextran terminated moiety, or a terminal moiety containing positive or negative charges for the organosiloxy moieties), where the terminal moiety is disposed at its enclosure-facing terminus (i.e. the portion of the monolayer of the coating material 298 that is not bound to the inner surfaces 292, 294 and is proximal to the enclosure 284).

In other embodiments, the coating material 298 used to coat the inner surface(s) 292, 294 of the microfluidic device 290 can include anionic, cationic, or zwitterionic moieties, or any combination thereof. Without intending to be limited by theory, by presenting cationic moieties, anionic moieties, and/or zwitterionic moieties at the inner surfaces of the enclosure 284 of the microfluidic circuit 120, the coating material 298 can form strong hydrogen bonds with water molecules such that the resulting water of hydration acts as a layer (or "shield") that separates the biological micro-objects from interactions with non-biological molecules (e.g., the silicon and/or silicon oxide of the substrate). In addition, in embodiments in which the coating material 298 is used in conjunction with coating agents, the anions, cations, and/or zwitterions of the coating material 298 can form ionic bonds with the charged portions of non-covalent coating agents (e.g. proteins in solution) that are present in a medium 180 (e.g. a coating solution) in the enclosure 284.

In still other embodiments, the coating material may comprise or be chemically modified to present a hydrophilic coating agent at its enclosure-facing terminus. In some embodiments, the coating material may include an alkylene ether containing polymer, such as PEG. In some embodiments, the coating material may include a polysaccharide, such as dextran. Like the charged moieties discussed above (e.g., anionic, cationic, and zwitterionic moieties), the hydrophilic coating agent can form strong hydrogen bonds with water molecules such that the resulting water of hydration acts as a layer (or "shield") that separates the biological micro-objects from interactions with non-biological molecules (e.g., the silicon and/or silicon oxide of the substrate).

Further details of appropriate coating treatments and modifications may be found at U.S. Patent Publication No. US2016/0312165, which is incorporated by reference in its entirety.

Additional System Components for Maintenance of Viability of Cells within the Sequestration Pens of the Microfluidic Device.

In order to promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells. These types of additional components have been described, for example, in U.S. Patent Publication No. US2016/0312165.

Methods, Systems, and Devices for Selecting and/or Generating Genome-Edited T Cells.

The disclosed methods, systems and devices are suitable for selecting and expanding genome-edited T cells to create clonal T cell populations which can be screened for a desired genotype (e.g., a targeted genome edit, optionally in combination with no off-target modifications to the genome). The disclosed methods, systems and devices are also suitable for performing targeted genome editing or non-targeted genome editing, either of which may include transfection, in T cells while they are located within a microfluidic device.

Figure 4:
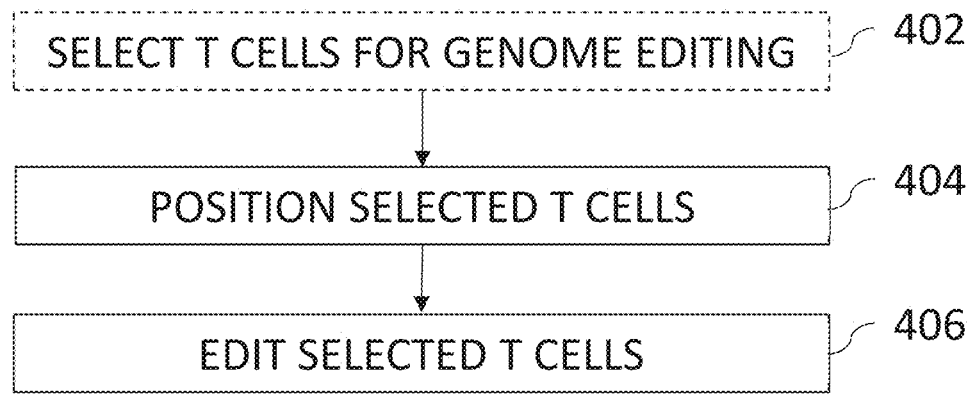
FIG. 4 illustrates steps in a method for genome editing of T cells according to some embodiments of the disclosure.

FIG. 4 illustrates steps in an exemplary method of editing the genome of a T cell (or cells) within a microfluidic device. The microfluidic device can include a substrate having a dielectrophoresis (DEP) configuration and/or an electrowetting (EW) configuration. For example, the substrate can have a DEP configuration and, optionally, an EW configuration. The DEP configuration and/or the EW configuration can be optically actuated, at least in part. Thus, for example, the DEP-configured substrate of the microfluidic device, or a portion thereof, can include an optoelectronic tweezer (OET) configuration. Likewise, the EW-configured substrate of the microfluidic device, or a portion thereof, can include an opto-electrowetting (OEW) configuration. Steps that require the positioning of one or more micro-objects (e.g., cells, beads, etc.) can be performed using dielectrophoretic force (e.g. OET force), and/or steps that require the movement of droplets (e.g., which may contain micro-objects) can be performed using electro-wetting force (e.g. OEW force), depending on the embodiment and the configuration of the microfluidic device used. As discussed below, some of the steps in the method may be performed outside of the microfluidic device.

The method of FIG. 4 optionally starts with step 402, the selection of T cells for genome editing. T cells can be selected based on a number of different criteria and/or characteristics, including but not limited to: morphology, size, motility (e.g. chemotaxis), production of a protein of interest, reaction to a specific antibody, presence of one or more cell surface markers, rate of proliferation, activation by an antigen of interest, or any combination thereof. For example, T cells can be selected based on their cell surface expression of CD3, CD4, CD8, or any combination thereof. Alternatively, T cells can be selected based on their expression of CD3 in combination with at least one of CD4, CD8, CD25, CD38, and CD40. As another example, the T cell(s) may be selected based on their activation by an antigen of interest, particularly an antigen of interest presented by an MHC molecule (e.g., an MHC tetramer complex). As yet another example, the selection of T cells can be a negative selection that removes non-T cells from a mixture of different cells types (e.g., PBMCs). T cells selected for genome editing may be homogeneous (i.e., having essentially the same or similar cellular characteristics). Alternatively, the T cells selected for transfection may be heterogeneous (i.e., exhibiting different cellular characteristics).

Assays to identify various cellular criteria and/or characteristics of T cells may be performed within the microfluidic device. Production of a protein of interest may be assayed, for example, as described in U.S. Pat. No. 8,921,055, U.S. Patent Application Publication No. 2015/0151298, or U.S. Patent Application Publication No. 2016/0160259, the entirety of each of which is incorporated herein by reference. Cell size, morphology, and/or proliferation may be quantified using cell detection algorithms, such as described in U.S. Patent Application Publication No. 2016/0171686, the entirety of which is incorporated herein by reference. In some embodiments, where the T cell(s) are selected for transfection based on one or more time-dependent characteristics, such as rate of proliferation, rate of production of an analyte of interest (e.g., a protein) which may or may not be responsive to a stimulus, or motility rate, it may be necessary to maintain the T cell(s) within the microfluidic device (e.g., within one or more sequestration pens) for a period of time and/or contact the T cell(s) with one or more reagents. In some embodiments, one or more of the cellular criteria and/or characteristics that provide the basis for selection may be monitored in an automated manner.

In some embodiments, it may be necessary to expand the T cell(s) within the microfluidic device in order to assay for a cellular criteria and/or characteristic of interest. Likewise, for some assays, such as measurement of an analyte of interest, it may be helpful to expand a T cell into a clonal population of T cells in order to increase assay signal (e.g., increase the amount of secreted protein to an amount sufficient to quantify). Whether the T cell(s) is/are expanded or not, the assay signal can be measured relative to an absolute value or an on-chip control. As used herein, "expanding a cell" refers to the maintenance of a cell in a suitable culture medium for a period of time sufficient for the cell to mitotically divide and produce at least two daughter cells, each of which is viable. A T cell culture medium suitable for expansion can include, for example, a base medium high in phosphate, mammalian serum (e.g., human and/or bovine or calf), and IL-2. One particular example of a T cell culture medium comprises RPMI, 10% FBS, 2% Human AB serum, and 50 U/ml IL-2. T cell culture media, for example, in of In some embodiments, the T cell(s) may be selected based on one or more characteristics related to previously-performed treatments, such as a previous transfection and/or genome edit, including the successful integration of exogenous DNA into a specific site within the genome of the T cell(s) (referred to herein as a "target site") and/or successful deletion of endogenous DNA from a target site within the genome of the T cell(s). For example, the T cell(s) may be selected for the presence of a T cell receptor having a known sequence and activity or an artificial T cell receptor, such as a CAR-T protein. Alternatively (or in addition, the T cell(s) may be selected for the absence of a protein or other molecule, such as an immune checkpoint inhibitor (e.g., PD-1, CTLA4, TIM-3, LAG-3, or the like) or other cell surface receptor (e.g., a viral receptor, such as CCR4 or CCR5).

Depending on the embodiment, the cell(s) may be selected for genome editing based on more than one cellular criteria and/or characteristic. Thus, in some embodiments, two or more selection steps can be performed, each of which may be performed independent of the other(s), within the microfluidic device or prior to loading the cells into the microfluidic device. For example, cells may undergo a first selection using flow-cytometry (or another technique that can be performed outside of the micro-fluidic device, such as positive or negative sorting using magnetic beads), after which the cells can be introduced into the microfluidic device and undergo a second selection based on size, morphology, cell surface marker(s), T cell activation, or the like. The second selection can include using a force, such as a DEP or OET force, to move selected cells away from unselected cells, or vice versa.

In some embodiments, it may be necessary to expand selected T cells in order to have a population of T cells suitable for genome editing, which can include transfection and various subsequent steps. As discussed below, some methods of transfection, such as electroporation, increase the porosity of cells and thus may damage T cells or otherwise impact their viability. In embodiments that use such methods of transfection, it may be necessary to transfect a large number of selected T cells in order to obtain a sufficient number of viable transfected T cells.

In step 404 of the method of FIG. 4, T cells (which may be unselected if step 402 is skipped) are positioned for transfection. As used herein, the term "transfection" refers to the movement of a nucleic acid construct, which may be part of a genome editing biomolecule, a donor template, or the like, into the interior of a cell. Thus, step 404 can include moving selected T cells to a region of the microfluidic device configured for transfection (i.e., a "transfection region" or an "editing region"). In some embodiments, in which the T cells are selected for transfection within the microfluidic device (either partially or completely), the selected T cells can be moved from a region in which the T cells are selected (i.e., a "selection region") of the microfluidic device to the editing region of the microfluidic device. The selection region, for example, could be a microfluidic channel, and the editing region could be a chamber configured for cellular transfection. Alternatively, the selection region can be a chamber in the microfluidic device and the editing region can be a separate chamber in the microfluidic device. In other embodiments, step 404 can include loading already selected T cells into the microfluidic device and then moving the T cells into the editing region. For example, if the T cells are selected for transfection outside of the microfluidic device, the selected T cells can be loaded into the microfluidic device and transported directly to the editing region (e.g., via a flow path, such as a microfluidic channel). In still other embodiments, step 404 can include loading the T cells (whether selected or not) directly into an editing region of the microfluidic device. Depending on the embodiment and the configuration of the microfluidic device, the T cells may be moved using fluid flow, gravity, centrifugal force, DEP force (e.g., OET force), EW force (e.g., OEW force), or any combination thereof, as discussed elsewhere herein.

The editing region can vary according to the embodiment and the type of microfluidic device used. In some embodiments, the editing region comprises a series of chambers, each of which may be configured for genetic modification of a limited number of cells. For example, the editing region may comprise a plurality of sequestration pens, with each sequestration pen configured to promote cellular transfection (as discussed further below). The plurality of sequestration pens may open off of any one of one or more microfluidic channels in the microfluidic device, such as a common microfluidic channel. In other embodiments, the editing region is a large chamber or similar holding region within the microfluidic device, wherein the chamber/holding region is configured to promote cellular transfection (as discussed further below). In still other embodiments, the editing region is located in a first microfluidic device which is specialized for cellular transfection, and the first microfluidic device is connected (e.g., by tubing or some other type of conduit) to a second microfluidic device which is suitable for maintaining, culturing, and/or expanding transfected T cells and/or assaying transfected T cells for the presence of a desired genetic alteration. As discussed below, depending on the type of transfection performed, the editing region may contain physical features or structures that facilitate transfection of the cells with a genome editing biomolecule.

In some embodiments, particularly embodiments in which the T cells are selected either partially or completely within the microfluidic device, step 404 can include separating cells that are not selected for genome editing ("unselected cells") from the selected T cells. For example, selected T cells may be moved from a selection region to the editing region, while unselected cells are left behind in the selection region. Alternatively, both selected and unselected cells can be moved into the editing region, and then the unselected cells can be moved out of the editing region. Regardless, the unselected cells may be discarded. For example, the unselected cells can be moved to a region of the microfluidic device designated for excess or unwanted cells. Alternatively, the unselected cells can be flushed from the microfluidic device and, optionally, discarded. For example, the microfluidic device can include a selection region that comprises a microfluidic channel and, following movement of selected T cells to the editing region, unselected cells can be flushed out of the channel (and the microfluidic device) with a flow of medium.

In step 406 of the method of FIG. 4, selected T cells are edited. Editing may be accomplished in a variety of ways. In various embodiments, editing comprises contacting one or more T cells with a genome editing biomolecule, optionally in combination with a donor template. The term "genome editing biomolecule", as used herein, refers to a molecule, complex, or macromolecular assembly which, upon entry into a cell, is capable of facilitating a stable alteration to the genome of the cell. As used herein, a "stable" alteration is one that is retained by daughter cells produced via division of the edited cell (i.e., the cell altered as a result of being contacted by the genome editing biomolecule). A stable alteration can be maintained for at least one, two, three, four, five, six, seven, eight, nine, ten, eleven, twelve, fifteen, twenty, twenty-five, or more cell divisions. In some embodiments, a stable alteration to the genome of a cell includes an insertion and/or deletion of nucleic acid in the nuclear or mitochondrial DNA of the cell. In some embodiments, a stable alteration to the genome of a cell includes an epigenetic change that alters the expression or activity of the nuclear or mitochondrial DNA of the cell in a stable manner. The genome editing biomolecule can be non-covalently associated with, or otherwise mixed with, one or more biological or organic molecules and/or one or more inorganic molecules or ions.

A genome editing biomolecule can comprise, consist of, or consist essentially of a nucleic acid molecule. The nucleic acid molecule can be single-stranded (e.g., single-stranded RNA, DNA, or a combination thereof) or double-stranded (e.g., double-stranded RNA, DNA, or a hybrid thereof). The genome editing biomolecule can comprise one or more expression cassettes, any one of which may comprise the nucleic acid molecule. Alternatively, the genome editing biomolecule can comprise a viral vector which may comprise the nucleic acid molecule. The viral vector can be a vector derived from a lentivirus (e.g., an integrase-deficient lentiviral vector), such as HIV or the like.

The genome editing biomolecule can comprise a nuclease, such as an endonuclease, that facilitates alteration of the genome of a T cell. For example, the nuclease can cleave DNA, creating a double-strand break which, when repaired by the cell, becomes modified to include an insertion of an exogenous nucleic acid sequence and/or a deletion of an endogenous nucleic acid sequence. The nuclease can function in a site-specific manner, thereby enabling targeted genome editing. As used herein, "targeted genome editing" refers to the introduction of exogenous nucleic acid at a pre-selected target site in the genome of a cell and/or the deletion of endogenous nucleic acid at the pre-selected target site in the genome of the cell. In some embodiments, the nuclease is encoded by the genome editing biomolecule. For example, the nuclease can be encoded by a nucleic acid molecule (or expression cassette) comprised by the genome editing biomolecule. Alternatively, the nuclease can be a protein. For example, the nuclease can be complexed with a nucleic acid molecule, and the complex can be comprised by the genome editing biomolecule. In some embodiments, the nuclease can be a nucleic acid-guided endonuclease, and the nucleic acid molecule can be a guide nucleic acid. The nucleic acid-guided endonuclease can be an RNA-guided endonuclease or a DNA-guided endonuclease. Cas9 (e.g., spCas9, stCas9, nmCas9, eSpCas9) and Cpf1 are non-limiting examples of RNA-guided endonucleases that may be used in the disclosed methods. *Natronobacterium gregori* Argonaute (NgAgo) is a non-limiting example of a DNA-guided endonuclease that may be used in the disclosed methods. In other embodiments, the nuclease can be a Zinc Finger Nuclease (ZFN) or a Transcription Activator-like Effector Nuclease (TALEN), either of which may be associated with Fok1. Other nucleases and associated DNA-binding molecules suitable for use in the disclosed methods are known to those skilled in the art. See, for example, Richardson et al., Enhancing homology-directed genome editing by catalytically active and inactive CRISPR-Cas9 using asymmetric donor DNA, Nature Biotechnology 34:339-344 (2016); and Slaymaker et al., Rationally engineered Cas9 nucleases with improved specificity, Science, 351(6268):84-8.

In other embodiments, the genome editing biomolecule can comprise elements that facilitate the random integration of exogenous DNA into the genomes of cells (referred to herein as "non-targeted genome editing"). For example, the genome editing biomolecule can comprise a nucleic acid molecule that includes repeat elements (e.g., inverted repeats) and, optionally, a transposase. The transposase can be encoded by the nucleic acid molecule, encoded by a separate nucleic acid molecule, or may be a protein, which may be complexed with the nucleic acid molecule.

In some embodiments, a genome editing biomolecule can be complexed or otherwise associated with one or more proteins, lipids, organic ions, inorganic ions, or any combination thereof. The complex/association can facilitate the entry of the genome editing biomolecule into a cell. For example, the proteins and/or lipids can be part of a viral capsid or a liposome. Alternatively, a protein comprised by the genome editing biomolecule can be fused to a cell-penetrating peptide. For example, the protein can be an endonuclease or transposase that is fused to a cell-penetrating peptide.

In addition to the foregoing, various genome editing biomolecules suitable for targeted and non-targeted genome editing are known in the art. See, for example, Nayerossadat et al., Viral and nonviral delivery systems for gene delivery, Adv. Biomed Res. 1:27 (2012); and Zuris et al., Cationic lipid-mediated delivery of proteins enables efficient protein-based genome editing in vitro and in vivo, Nature Biotech 33:73-80 (2015).

The genome editing biomolecule can comprise a donor template nucleic acid, such as a donor template DNA molecule. Alternatively, the genome editing biomolecule and the donor template can be distinct molecular or macromolecular entities. As used herein, a "donor template" or "targeting nucleic acid construct" is a nucleic acid molecule comprising a delivery sequence; a "delivery sequence" is a nucleic acid sequence which has been selected for introduction into the genome of a cell. For embodiments in which the genome editing biomolecule and the donor template are distinct entities, methods of editing the genome of a selected T cell (or cells) further comprise the step of contacting the one or more T cells with the donor template. The donor template can be provided, for example, in combination with the genome editing biomolecule, such as in a mixture. Alternatively, the one or more T cells can be contacted with the genome editing biomolecule and the donor template at different times (e.g., sequentially).

The delivery sequence of the donor template can be a nucleic acid sequence which comprises or encodes a functional biomolecule that complements a mutation or functional deficiency in the genome of the cell being modified ("selected cell" or "target cell"). For example, the delivery sequence can include at least a portion of a gene or associate regulatory sequence; the gene, portion thereof, or regulatory sequence can be a wild-type sequence or a functional variant thereof. The functional variant can be an allelic variant (e.g., a known or novel allelic variant), which may include one or more point mutations (e.g., alteration, insertion, or deletion of a single base) that do not substantially diminish the function of the variant relative to a wild-type sequence.

Alternatively, the delivery sequence of the donor template can be a nucleic acid sequence which is configured to generate a mutation or functional deficiency in the genome of the target cell. For example, the delivery sequence can include at least a portion of a gene or associate regulatory sequence that includes a non-wild type sequence having reduced function. The reduced-function, non-wild type sequence can include one or more deletions, one or more point mutations (e.g., alteration, insertion, or deletion of a single base), or any combination thereof; the reduction in function (assessed relative to a corresponding wild-type sequence) can be partial or complete.

As yet another alternative, the delivery sequence of the donor template can include a nucleic acid sequence that comprises or encodes a functional biomolecule that confers an atypical functional activity upon a modified cell. For example, the delivery sequence can: include a hyper-functional allele of a gene, or a portion thereof, capable of increasing the overall level of activity of the gene in the cell; include a regulatory sequence configured for introduction at an atypical site in the genome of the target cell (e.g., the regulatory sequence can be flanked by sequences from a target site in the genome of the target cell); encode a fusion protein (e.g., a T cell receptor fusion protein, such as a CAR-T protein or the like); include a sequence that is found in the genome of a species which is different than the species of the target cell (e.g., the delivery sequence can be from a first mammal, such as a human, and the cell being genetically modified can be from a second mammal, such as a mouse, rat, sheep, goat, cow, or the like); include a sequence that encodes a reporter molecule; and/or include a synthetic sequence that is foreign to the target cell. The reporter molecule can be a molecule which is detectable in cells which have been genetically modified. For example, the reporter molecule can be a fluorescent protein (e.g., GFP or the like) or an RNA sequence that mimics a fluorescent protein (e.g. a "spinach" RNA aptamer). Alternatively, the reporter molecule can be a cell surface marker (which may or may not have an additional activity beyond serving as a marker), a protein that provides resistance to a selective agent, such as an antibiotic, or an enzyme that produces a quantifiable signal, such as horseradish peroxidase.

The delivery sequence of the donor template can include a barcode sequence. The barcode sequence (or "tag sequence") can be a random sequence of nucleotides (e.g., 6, 7, 8, 9, 10, 11, 12, 13, 14, 15, or more nucleotides) that differs between different genome editing biomolecules (or donor templates). The barcode sequence, in some embodiments, can comprise a sequence not typically found in the genome of the target cell or at least not proximal to (e.g., within 1, 2, 3, 4, 5, 10, or more kb) the location of the target site in the genome of the target cell.

The donor template can further comprise one or more targeting nucleic acid sequences that flank the delivery sequence on one or both sides. As used herein, a "targeting nucleic acid sequence" is a sequence that is sufficiently homologous to a nucleic acid sequence that flanks a target site in the genome of a target cell so as to increase the likelihood and fidelity of homologous recombination between the donor template nucleic acid and the nucleic acid sequence of the target site.

In some embodiments, genomic editing of T cells placed within an editing region of a microfluidic chip comprises subjecting the T cells to one or more forces that increase cell permeability and/or cell porosity, thereby increasing transfection efficiency. Depending on the type of force used, the editing region of the microfluidic device may contain corresponding structures or elements that facilitate generation of the force and/or the formation of pores in the cell membranes of the cells.

In some embodiments, genomic editing of T cells placed within an editing region of a microfluidic chip comprises electroporating the T cells. Electroporation of T cells can be accomplished, for example, by applying a DEP force to the T cells. The use of DEP force to electroporate cells has been described in the art, including, for example, in Valley et al., Parallel single-cell light-induced electroporation and dielectrophorectic manipulation, Lab on a Chip 9:1714-17102 (2009). Accordingly, the editing region of the microfluidic device can have a DEP configuration, which can be as disclosed elsewhere herein, including an OET configuration. The editing region of the microfluidic device can comprise a substrate that is different from the substrate in other regions of the microfluidic device. The substrate, in combination with a cover and/or microfluidic circuit material, can define the editing region.

The substrate of the editing region can include at least one electrode. The at least one electrode of the substrate can form a select portion of a substrate surface that faces inward toward the editing region. Alternatively, the at least one electrode of the substrate can form all (or substantially all) of the inward facing surface of the substrate within the editing region. Regardless, at least one electrode can be a single discrete electrode. Alternatively, the at least one electrode can be a plurality of discrete electrodes. When a plurality of discrete electrodes is present, the electrodes can form an orderly array, such as an n×m array wherein n and m are each an integer having a value of 1 or greater, or any portion of such an n×m array). The electrodes of an orderly array can be individually addressable. One or more (e.g., each) of the at least one electrodes of the substrate can be made from a metal. The metal can be, for example, any metal used in semiconductor processing, including a non-oxidizing metal (e.g., Au, Pt, or the like), an alloy thereof, and/or a stack of metal layers. Activation of the metal electrodes can be controlled via transistor switches, including phototransistor switches.

The substrate of the editing region can include at least one electrode and a photoconductive layer. The photoconductive layer of the substrate can form a select portion of a substrate surface that faces inward toward the editing region, or the photoconductive layer can form all (or substantially all) of the substrate surface that faces inward toward the editing region. The at least one electrode of the substrate can be electrically coupled to the photoconductive layer while remaining insulated from fluid present in the editing region. The photoconductive layer can comprise one or more phototransistors. Alternatively, the photoconductive layer can comprise, consist of, or consist essentially of a layer of hydrogenated amorphous silicon (a-Si:H).

Genomic editing of T cells can include placing the cells in a buffer that is optimized for electroporation, such as a low-conductivity buffer. The low conductivity buffer can be present in the editing region, for example, and moving the cells into the editing region can constitute placing the cells in the buffer. The low-conductivity buffer can minimize damage to the T cells caused by electroporation.

Genomic editing of T cells placed within an editing region of a microfluidic chip can include constricting or deforming the cell membranes of the T cells in order to increase cell permeability and/or porosity, thereby increasing transfection efficiency. To achieve such constriction or deformation, the editing region of the microfluidic device can include physical structures configured to constrict or deform target cells. For example, the editing region can have a microfluidic channel that includes one or more constrictions. As used herein, a "constriction" in a microfluidic channel is a portion of the channel having a width that is smaller than the average diameter of a target cell (which, in the case of T cells, can change depending on whether the T cells are activated or not). The entire channel may narrow to form the constriction, or the channel may include barriers (e.g., posts) that are separated by a distance smaller than the average diameter of the target cell. The constriction in the walls of the channel or the barriers can be formed, for example, through the patterning of microfluidic circuit material. Alternatively, hydrogel structures formed in situ can be used to create one or more constrictions within a microfluidic channel, either by effectively reducing the width of the channel or by providing barriers. The hydrogel structures can be generated in situ by directing structured light onto a photo-activatable polymer, as described elsewhere herein. For example, structured UV light directed through a light modulating subsystem can activate the polymerization of a photo-activatable polymer in specific locations within the editing region of the microfluidic device. As another example, a hydrogel structure may be "drawn" around a target cell located within the editing region, causing constriction of the target cell. In some embodiments, hydrogel structures within the editing region can also be used to limit diffusion of media containing the genome editing biomolecule, thereby retaining the genome editing biomolecule in close proximity to the target cell to facilitate successful transfection; and/or to contain (or seal) target cells within the editing region of the microfluidic device.

In some embodiments, genomic editing of T cells placed within an editing region of a microfluidic chip comprises impaling the T cells on microstructures. This process is generally known in the art as "impalefection." In these embodiments, one or more inner surfaces of the editing region of the microfluidic device may be patterned with microstructures, such as nanotubes. In some embodiments, the microstructures may be infused with media comprising the genome editing biomolecule, or the microstructures may be used to capture micro-objects such as beads comprising the genome editing biomolecule. In certain embodiments, DEP force may be used to push the T cells onto the microstructures such that the microstructures impale the cells. In other embodiments, a flow of medium can be used to push the T cells onto the microstructures such that the microstructures impale the cells. The flow of medium can be generated in any manner described herein or otherwise known in the art, including the pumping of medium through the microfluidic device and localized flow. The generation of localized flow within a microfluidic device has been described, for example, in U.S. Patent Application Publication No. 2016/0158757, the entire contents of which are incorporated herein by reference.

In some embodiments, genomic editing of T cells placed within an editing region of a microfluidic chip comprises subjecting the T cells to a high-intensity ultrasound frequency. The ultrasound frequency can be selected so as to induce pore formation (sonoporation), and can optionally be applied when the cells are in the presence of an agent that facilitates pore formation. Micro-bubbles that are subject to acoustic cavitation when exposed to ultrasound may be used as an agent that facilitates pore formation.

In some embodiments, genomic editing of T cells placed within an editing region of a microfluidic chip comprises contacting the T cells with magnetic nanoparticles that comprise the genome editing biomolecule (and, optionally, donor template). In such embodiments, the transfection area of the microfluidic device may include a magnet, which may be integrated into the support structure or into the substrate of the microfluidic device. Regardless, the magnet can be controllably applied so as to force contact between the T cells and magnetic nanoparticles once the cells are properly positioned in the editing region.

Depending on the embodiment, the application of force to facilitate cell permeability and/or porosity, including pore formation, can be performed after, or at substantially the same time as, contacting the target cell(s) with the genome editing biomolecule (and, optionally, donor template). The genome editing biomolecule (and donor template, if necessary) may be introduced directly into the editing region by means of a flow of fluidic medium through the editing region, which may occur concurrent with the introduction of target cells into the editing region (e.g., the target cells and genome editing biomolecules can be part of a mixture that is flowed into the editing region). Alternatively, the genome editing biomolecule (and donor template, if necessary) may be introduced indirectly, such as by diffusion from a fluidic medium flowing past an opening to the editing region. In still other alternatives, the genome editing biomolecule can be associated with a surface of a transfection structure, such as a wall or barrier within the editing region, a microstructure, or a nanoparticle. Microstructure and nanoparticle transfection structures can be localized to the editing region either prior to moving the target cells into the editing region, at the same time as moving the target cells into the editing region (e.g., if the structure is present in the same medium as the cells), or after the cells are moved into the editing region (e.g., if the structure can be moved into the editing region by means of a selective force, such as DEP). The fluidic medium within the editing region of the microfluidic device can comprise different molecules or compounds which facilitate cell permeability and/or cell porosity and the transfection of the cells.

A variety of the above methods for introducing genome editing biomolecules into cells may be used, but certain methods can provide advantages for minimizing cellular toxicity and/or editing T cells. For example, electroporation of mRNA encoding an endonuclease, optionally in combination with guide RNAs (gRNAs), can facilitate ex vivo gene editing of primary T cells. Alternatively, direct delivery of purified endonuclease protein or an endonuclease-nucleic acid complex (e.g., Cas9 protein-gRNA complex) can achieve high levels of gene editing, which such delivery affected by electroporation or by fusion to cell-penetrating peptides (which obviates electroporation-mediated toxicity). Viral vectors offer additional means of delivering genome editing biomolecules with high efficiency while minimizing cytotoxicity. For example, a lentiviral vector, such as an HIV-based vector, may be used for efficient transduction of T cells; and an integrase-deficient lentiviral (or HIV-based) vector may be beneficially employed for transient introduction of genome editing biomolecules into a target cell. Under select conditions, adenoviral vectors can also achieve high levels of transduction ex vivo in T cells (see, e.g., Wickham et al. (1997), J. Virology 71(10):7663-69), while expressing functional components of the genome editing biomolecule (e.g., endonuclease) only transiently. Both lentiviral and adenoviral vectors provide cargo capacity sufficient to carry multiple nucleases and/or gRNA expression cassettes, and thus can allow for multiplex editing of several target sites within a genome.

Figure 5:
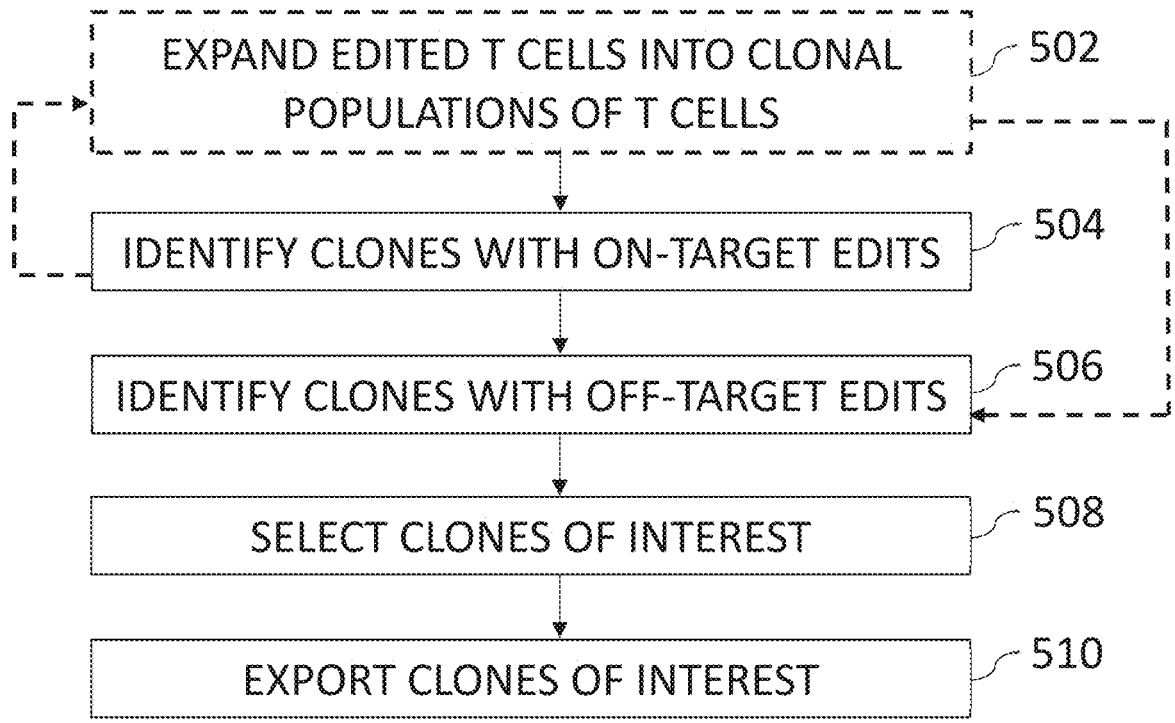
FIG. 5 illustrates steps in a method for identifying T cells that have been successfully genome-edited according to some embodiments of the disclosure.

Once one or more T cells (e.g., a population of T cells) have been subjected to a genome editing process, it is typically necessary to ascertain whether any of the cells have been successfully edited. The identification of successfully edited cells can be facilitated using a microfluidic device as described herein, particularly microfluidic devices having sequestration pens configured for single cell isolation and expansion. FIG. 5 illustrates steps in an exemplary method 500 for selecting, analyzing, and identifying cells that have undergone a successful targeted (or non-targeted) genome editing event. At step 502 of method 500, T cells that have been subjected to a genome editing process are expanded into clonal populations. The expansion into clonal populations can include isolating single T cells from the population of genome edited cells and expanding the single T cells into distinct clonal populations. For example, individual T cells can be isolated in corresponding sequestration pens in the microfluidic device and cultured under conditions conducive to the expansion of single T cells into clonal colonies. The production of clonal T cell populations derived from single T cells facilitates genomic analysis, as discussed further below. Method 500 can be performed with genome edited T cells that have been edited by any method known in the art or described herein, whether the editing process was performed within the microfluidic device or outside of the microfluidic device (i.e., prior to loading the population of genome edited cells into the microfluidic device).

In some embodiments, the method 500 includes a step (not shown in FIG. 5) of performing an initial selection on the population of genome edited T cells to produce a subpopulation of cells enriched for T cells that include a successful genome edit (e.g., a successful targeted edit). The first selection can be performed before, during, or after step 502.

The initial selection can be based upon a detectable marker that is eliminated (or detectably reduced) as a result of a successful genome edit. For example, the genome edit can be targeted, and a coding region that encodes at least part of the detectable marker and/or a non-coding regulatory sequence that is required for expression of the detectable marker can be removed by a successful genome editing event. The detectable marker can be an epitope of a biomolecule that is expressed in pre-edited T cells and T cells that go through the editing process without being successfully edited. The biomolecule can be, for example, a protein or carbohydrate molecule that localizes to the cell surface (e.g., PD-1, CTLA4, TIM-3, LAG-3, CCR4, CCR5, and the like). Alternatively, the detectable marker can be a light-generating biomolecule, which may have an intracellular localization. Examples of light-generating biomolecules include, but are not limited to, green fluorescent protein (GFP) and derivatives thereof; bioluminescent proteins and derivatives thereof; enzymes the cleave a substrate that emits light upon cleavage; and the like. Thus, for example, the population of T cells that have been subjected to the genome editing process can, prior to the genome editing process, include a previous genome edit that introduced a coding region encoding the light-generating biomolecule. A "detectably reduced" level of a detectable marker can be reduced by 10%, 20%, 30%, 40%, 50%, 60%, 70%, 80%, 90%, or more relative to the level of the detectable marker in a starting T cell population (i.e., the population prior to the genome editing process) or T cells that have gone through the genome editing process without being successfully modified.

The initial selection can be, alternatively or in addition to the initial selection step described above, based upon a detectable marker that is introduced (or detectably increased in level) as a result of a successful genome edit. For example, the successful genome edit can introduced an exogenous nucleic acid sequence which encodes the detectable marker or a biomolecule, such as a protein, the generates the detectable marker. Alternatively, the successful genome edit can introduce an exogenous nucleic acid sequence which includes a non-coding, regulatory sequence that increases the expression of an endogenous nucleic acid sequence which encodes either the detectable marker or a biomolecule, such as a protein, the generates the detectable marker. The exogenous nucleic acid sequence can be part of a donor template, which may be part of a genome editing biomolecule, as discussed above. The detectable marker can be an epitope of a biomolecule that is either not expressed or expressed at low levels in pre-edited T cells and T cells that go through the editing process without being successfully edited. The biomolecule can be, for example, a protein or carbohydrate molecule that localizes to the cell surface (e.g., a specific TCR allele or CAR-T molecule). Alternatively, the detectable marker can be a light-generating biomolecule, which may have an intracellular localization. Examples of light-generating biomolecules are discussed above and otherwise known in the art. A "detectably increased" level of a detectable marker can be increased by 10%, 20%, 30%, 40%, 50%, 60%, 70%, 80%, 90%, or more relative to the level of the detectable marker in a starting T cell population (i.e., the population prior to the genome editing process) or T cells that have gone through the genome editing process without being successfully modified.

The initial selection of a subpopulation of genome edited T cells can be performed prior to loading the genome edited T cells into the microfluidic device. For example, genome edited T cells that express a particular cell-surface epitope can be selected from a population of genome edited T cells by means of fluorescent activated cell sorting (FACS), magnetic bead-based binding, or any other sorting technology known in the art. The subpopulation of cells obtained from such selection (i.e., "off-chip" selection) can then be loaded into the microfluidic device for further processing, such as according to method 500 of FIG. 5 or the like. Alternatively, the detectable marker-based selection of a subpopulation of genome edited cells can be performed after loading the population of genome edited T cells into the microfluidic device. For example, imaging can be used to detect cells that express a particular cell surface epitope, which may be labeled with an antibody or other specific binding agent having a fluorescent label. As another example, imaging can be used to detect cells that express a light-generating biomolecule. Regardless of the exact nature of the detectable marker (whether protein, carbohydrate, or light generating, and whether eliminated or introduced) cells identified as having the detectable marker can be selected and moved into corresponding sequestration pens. Thus, for example, the detection and selection of T cells can be performed while cells of the genome edited T cell population are located within a flow region (e.g., a microfluidic channel) in the microfluidic device.

The amount of detectable marker (or "reporter molecule") can be quantified, and T cells having less than a threshold amount of the detectable marker can be selected for further processing (e.g., according to method 500). Alternatively, or in addition (for instances in which both positive and negative selection are employed), the amount of detectable marker can be quantified, and T cells having more than a threshold amount of the detectable marker can be selected for further processing (e.g., according to method 500). In some embodiments, it may be beneficial to expand one or more individual T cells into clonal populations of T cells, to determine whether the cells of the clonal population(s) exhibit a reduction/increase in the detectable marker that is stable over time and/or after one or more cell divisions. For example, as discussed below, it may be beneficial to determine whether a single T cell that has a putative disruption of the CXCR4 gene continues to exhibit loss of CXCR4 surface expression as the single cell is expanded into a clonal population of cells. Similarly, in instances in which a genome edit results in a functional capability, as could be provided by a new receptor, such as a CAR-T receptor, it may be desirable to expand the T cells into a population of cells before detecting the receptor or assaying the functional capability.

In addition, for embodiments in which the T cells are subjected to force during transfection with a genome editing biomolecule (and/or donor template), it may be useful to expand the transfected T cells into clonal populations in order to determine whether transfection had any impact on cell viability. Similarly, in some embodiments, it may be beneficial to monitor T cell expansion to determine whether the T cells are proliferating at an expected rate. For example, because off-target genome editing could activate oncogenes or otherwise disrupt cell-cycle regulation, aberrant cell proliferation may be indicative of off-target genome editing.

As discussed above, genome-edited T cells can contain targeted genome edits, which may be on-target or off-target, or non-targeted (i.e., random) genome edits. As used herein, an "on-target genome edit" (or "on-target genomic modification") refers to the successful integration of a nucleic acid sequence from a donor template into a target site in the genome of the cell and/or a deletion of endogenous DNA from the target site; an "off-target genome edit" (or "off-target genomic modification") refers to the integration of a nucleic acid sequence from a genome editing biomolecule or donor template at a site in the genome of the cell other than the target site, and/or the deletion of endogenous DNA at a site in the genome of the cell other than the target site. Whether on-target, off-target, or non-targeted, T cells containing genome edits can be identified by characterization of their genomic sequence, or portions thereof. Thus, for example, at step 504 of method 500, cells that have been successfully modified to have on-target or non-targeted genome edits can be identified through characterization of their genomic sequence. Such characterization can include cell lysis, nucleic acid extraction, and further processing steps (e.g., fragmentation, tagging, amplification, and the like). For example, amplification of extracted, and optionally fragmented and/or tagged, nucleic acid using primers specific to the first nucleic acid sequence and/or the second nucleic acid sequence can allow detection of on target genome edits. Alternatively, or in addition, the characterization can include nucleic acid sequencing (e.g., DNA sequencing of select genomic regions, whole genome sequencing, RNA sequencing of select mRNA transcripts, whole transcriptome sequencing, and the like). Analysis of the results of such sequencing can be used to identify the first nucleic acid sequence and/or the second nucleic acid sequence, and thereby allow detection of on target genomic edits.

In order to use techniques that require nucleic acid extraction, it is typically necessary to expand a genome edited T cell into a clonal population of cells, so that a subset of cells of the clonal population may be processed for genomic analysis while another subset of cells of the clonal population may be preserved for subsequent use (which can include export from the microfluidic device and growth off chip). Accordingly, in some embodiments, the characterization of the genomic sequence of a clonal population of genome edited T cells comprises selecting one or more T cells from the clonal population and performing DNA and/or RNA characterization on the one or more cells. Step 604 can be performed partially or completely outside of the microfluidic device (i.e., "off chip"). For example, characterizing the genome of genome-edited T cells can include exporting one or more T cells from a clonal population and, following such export, performing cell lysis, nucleic acid extraction and processing, and nucleic acid sequencing off chip. Alternatively, characterizing the genome of genome-edited T cells can include moving one or more T cells of a clonal population from within a sequestration pen to another chamber in the microfluidic device, performing cell lysis and nucleic acid extraction and processing in the other chamber, and then exporting the processed nucleic acid for sequencing off chip.

Depending on the embodiment, any method of identifying successful on-target (or non-targeted) genome edits may be combined with any other method, in any order. For example, in some embodiments, T cells containing on-target (or non-targeted) genome edits may be identified by initially selecting single T cells based on the absence of one or more detectable markers (or reporter molecules), isolating and expanding marker-negative single T cells into clonal populations, and then extracting DNA (and/or RNA) from one or more T cells of one or more of the clonal populations to perform sequencing and confirm a successful on-target (or non-targeted) genome edit. In other embodiments, T cells containing on-target (or non-targeted) genome edits may be identified by initially selecting single T cells based on the absence of one or more detectable markers (or reporter molecules), isolating and expanding marker-negative single T cells into clonal populations, assaying the clonal T cell populations for the presence of one or more detectable markers (or associated activities), and then extracting DNA (and/or RNA) from one or more T cells of one or more of the clonal populations to perform sequencing and confirm a successful on-target (or non-targeted) genome edit. In other embodiments, T cells containing on-target (or non-targeted) genome edits may be identified by initially selecting single T cells based on the presence of one or more detectable markers (or reporter molecules), isolating and expanding marker-positive single T cells into clonal populations, assaying the clonal T cell populations for the absence of one or more detectable markers (or associated activities), and then extracting DNA (and/or RNA) from one or more T cells of one or more of the clonal populations to perform sequencing and confirm a successful on-target (or non-targeted) genome edit. Of course, in any of the foregoing methods, the step of isolating and expanding single T cells into clonal populations could be performed before the initial selection step. For example, T cells containing on-target (or non-targeted) genome edits may be identified by isolating and expanding single T cells into corresponding clonal populations, then detecting the absence of a marker (or reporter molecule) in the clonal populations, and then extracting DNA (and/or RNA) from one or more T cells of one or more of the clonal T cell populations for sequencing and analysis (to confirm a successful on-target (or non-targeted) genome edit).

In still other embodiments, T cells that have on-target (or non-targeted) genome edits can be identified by detecting a functional property of the on-target (or non-target) genome edit (e.g. a functional activity of a protein produced or deleted by the genome edit) in single T cells, isolating and expanding the single T cells into corresponding clonal populations, and then extracting DNA (and/or RNA) from one or more of cells of the clonal population to perform sequencing and confirm a successful on-target (or non-targeted) genome edit. In related embodiments, T cells that have on-target (or non-targeted) genome edits can be identified by first isolating and expanding single T cells into clonal populations, detecting a functional property of the on-target (or non-target) genome edit (e.g. a functional activity of a protein produced or deleted by the genome edit) in the clonal populations, and then extracting DNA (and/or RNA) from one or more of T cells of the clonal population to perform sequencing and confirm a successful on-target (or non-targeted) genome edit.

At step 506 of method 500, T cell populations identified as having successfully undergone genome editing can be analyzed to identify populations that harbor off-target genome edits. As with on-target genome edits, the presence of off-target genome edits (or defective non-targeted edits) may be assessed using a detectable marker (or reporter molecule) and/or by analyzing nucleic acid extracted from one or more T cells of the clonal populations. The reporter molecule may, for example, be part of or encoded by a donor template (and, optionally, a genome editing biomolecule, as discussed above) which is configured such that the part that is or encodes the reporter molecule is lost upon successful editing but potentially retained when the edit is off-target (or defective). Similar to step 504 of method 500, all or part of step 506 can be performed off chip. Moreover, all or part of step 506 may be performed in parallel with all or part of step 504. For example, nucleic acid may be extracted from one or more T cells of a clonal population and "deep sequenced" to identify both on-target genome edits and off-target genome edits. Similarly, in embodiments where a detectable marker is used to identify off-target/defective genome edits, the step of detecting the off-target/defective marker can be performed before, during, or after cloning of individual T cells to form T cell populations and before, during, or after the detection of markers associated with on-target/successful genome edits. In this latter regard, the Traffic Light Reporter system can be used, allowing for on-target genome edits and off-target genome edits to be identified simultaneously, based on the production of different reporter molecules.

As would be evident to skilled persons, step 502 of method 500 may be repeated after step 504 and/or step 506, for the purpose of further expanding cells having successful on-target (or non-target) genomic edits. Such further expansion of single cells into sub-clonal populations, followed by the repetition of step 504 (and, optionally, step 506), can be performed to determine whether the on-target (or non-targeted) genome edits are stable over time. Any of steps 502, 504 and 506 may be repeated multiple times, in any order, or simultaneously; and the presence of a detectable marker (or reporter molecule) may be continually assessed while a single T cell is expanded into a clonal population. Moreover, in any of the foregoing methods, a barcode sequence can be, upon insertion into the genome of a T cell, used to identify daughter T cells that are clonally derived from a successfully edited parent T cell. The barcode sequence may be used, for example, in conjunction with a step comprising nucleic acid amplification (e.g., PCR) and/or nucleic acid sequencing to identify on-target and/or off-target genome edits.

At step 508 of method 500, clonal T cell populations identified as comprising successful on-target (or non-targeted) genome edits are selected for export. At step 510 of method 500, one or more T cells of the selected clonal populations are exported from the microfluidic device (e.g., for further culture, expansion, and/or processing).

The microfluidic device used in methods of ascertaining the success of genomic editing can be any of the microfluidic devices disclosed herein. In certain embodiments, the microfluidic device can have a substrate having a DEP configuration, which can include, consist of, or consist essentially of an OET configuration. In some embodiments, the microfluidic device can have a substrate having a EW configuration, which can include, consist of, or consist essentially of an OEW configuration. In some embodiments, the microfluidic device can have a substrate having a first section having a DEP configuration (which can include, consist of, or consist essentially of an OET configuration), and a second section having an EW configuration (which can include, consist of, or consist essentially of an OEW configuration). In accordance with the configuration of the microfluidic device, steps that require the selection and/or movement of individual cells (or groups of cells), whether for placement in sequestration pens, export, or the like, may be performed using DEP force, OET force, EW force, OEW force, fluid flow, localized flow, bubble-driven flow, or any combination thereof. Similarly, steps that require movement of media, whether for the purpose of providing nutrients and/or reagents to cells or for transporting cells or other microobjects, can be performed using EW force, OEW force, fluid flow, localized flow, bubble-driven flow, or any combination thereof. As a particular example, genome edited T cells may be selected and moved into and out of a sequestration pen using DEP (and/or OET) force in a DEP (and/or OET)-configured portion of a microfluidic device, carried by fluid flow into an EW (and/or OEW)-configured portion of the microfluidic device, and then subjected to cell lysis and nucleic acid extraction and processing using EW (and/or OEW) force to manipulate droplets containing the cells, nucleic acids, and/or reagents.

Cells Useful in the Disclosed Methods.

The disclosed methods are generally directed to the genomic editing of T lymphocytes ("T cells") and the identification of T cell clones having a successfully edited genome. The T cells can be of mammalian origin. Mammalian T cells can be from any type of mammal, domesticated or wild, including rodents, such as rats (e.g. *Rattus* genus), mice (e.g., *Mus* genus), guinea pig (e.g., *Cavia* genus), and the like, rabbits (e.g., *Oryctolagus, Sylvilagus,* or *Pentalagus* genus), sheep (e.g., *Ovis* genus), goat (e.g., *Capra* genus), pig (e.g., *Sus* genus), cattle (e.g., *Bos* or *Bison* genus), horse (e.g., *Equus* genus), primates, including haplorrhine primates (e.g., monkeys) and strepsirrhines primates (e.g., lemurs, etc.), and apes, such as orangutans (e.g., genus *Pongo*), gorillas (e.g., genus *Gorilla*), chimpanzees (e.g., genus *Pan*), and humans (e.g., genus *Homo*).

In certain embodiments, the T cells express CD3 antigen. In certain embodiments, the T cells express CD3 antigen in combination with at least one gene/protein selected from the group consisting of CD4, CD8, T-bet, GATA-3, CD25, Foxp3, ROR-gammaT, CD38, and CD40.

Uses of Genome-Modified Cells.

Single gene disorders may be addressed using gene editing to ameliorate pathophysiology associated with the gene defect. The gene disorders may be selected from autosomal dominant, autosomal recessive, x-linked or y-linked disorders. Some exemplary disorders may benefit from delivery of gene edited T cells include, but are not limited to immune-mediated diseases (e.g., auto-immune diseases) and infectious diseases (e.g., virus-associated diseases, such as AIDS and the like).

Storage Devices.

Also provided are machine-readable storage devices for storing non-transitory machine-readable instructions for carrying out any of the methods disclosed herein. The machine-readable instructions can optionally provide for control of the imaging device used to obtain the images.

EXAMPLES

Example 1: Genetic Engineering of Human T Cells

Figure 6A:
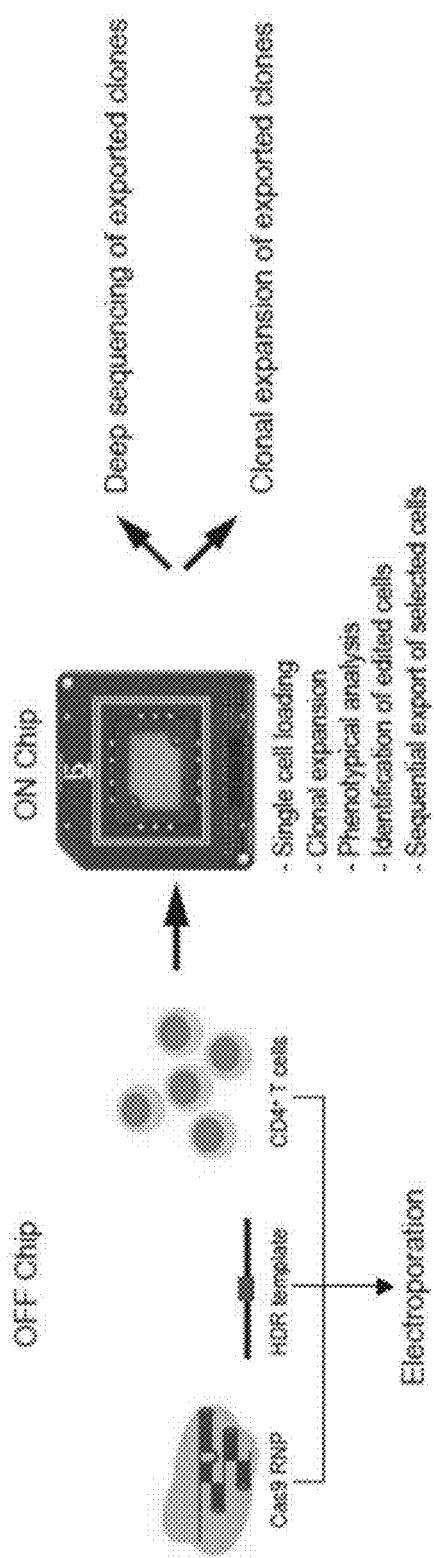
FIG. 6A illustrates a process for the identification of T cells that have been successfully genome edited according to a specific embodiment of the disclosure.
Figure 6B:
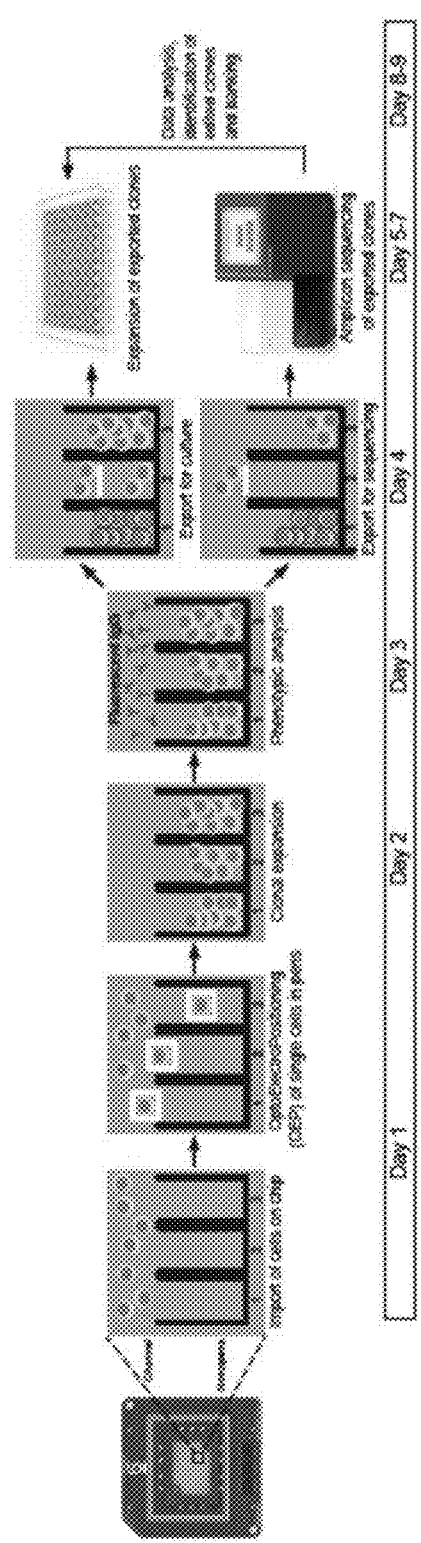
FIG. 6B illustrate steps in the process of FIG. 6A according to a specific embodiment of the disclosure.

Human CD4+ T cells were modified to remove functional copies of the CXCR4 gene, and successfully edited T cells were identified with the aid of an OptoSelect™ microfluidic device (Berkeley Lights, Inc.), basically as set forth in FIGS. 6A-B.

Human T Cell Isolation and Culture

Primary human T Cell culture and RNP editing has been previously described (Ref. 7, identified below). Briefly, PBMCs were isolated using SepMate™ tubes (Stemcell), per manufacturer's instructions, from blood from healthy human donors. CD3+ T cells were negatively isolated from PBMCs using an EasySep™ (Stemcell) negative magnetic isolation kit, per manufacturer's instructions. T cells, at a concentration of 1 million cells per 1 mL in RPMI media supplement with 10% FBS, were stimulated with plate-bound CD3 (10 ug/mL, Tonbo Biosciences, clone UCHT1) and soluable CD28 antibodies (5 ug/mL, Tonbo Biosciences, clone CD28.2). After electroporation, T cells were stimulated with CD3/CD28 Dynabeads™ (Cell Therapy Systems, 1:1 bead to cell ratio) and 20 U/mL of IL-2 (UCSF Pharmacy), again at a concentration of 1 million cells per mL of media, until import onto the OptoSelect™ chip.

Cas9 RNPs electroporation

A two-component gRNA system was used. crRNAs targeting either CXCR4 (target sequence 5' to 3': GAAGCGTGATGACAAAGAGG; SEQ ID NO: 7) or no human genomic sequence ("Scrambled" gRNA, 5' to 3': GGTTCTTGACTACCGTAATT; SEQ ID NO: 8) were synthesized (Dharmacon) and resuspended in 10 mM Tris HCl pH 7.4 with 150 mM KCl to a final concentration of 160 uM. tracrRNA was similarly synthesized and resuspended. The crRNA and tracrRNA were mixed 1:1 by volume and incubated for 30 minutes at 37° C. to produce 80 uM gRNA. 40 uM SpCas9 (QB3 Macrolab) was added at 1:1 by volume to the gRNA (a 1:2 molar ratio of Cas9 to gRNA) and incubated for 15 minutes at 37° C. to yield a 20 uM RNP. RNPs were prepared immediately before electroporation into T cells. A short ssDNA HDR template (ssODN) to insert a defined 12 bp sequence into CXCR4 was chemically synthesized (IDT) and resuspended in nuclease-free H2O to a concentration of 100 uM. The same CXCR4 targeting HDR template (DNA sequence 5' to 3': GGG CAA TGG ATT GGT CAT CCT GGT CAT GGG TTA CCA GAA GAA ACT GAG AAG CAT GAC GGA CAA GTA CAG GCT GCA CCT GTC AGT GGC CGA AAG CTT GGA TCC CAT CAC GCT TCC CTT CTG GGC AGT TGA TGC CGT GGC AAA CTG GTA CTT TGG GAA CTT CCT ATG CAA GGC AGT CCA TGT CAT CTA CAC AGT; SEQ ID NO: 9) was used for both CXCR4 and Scrambled gRNAs. Two days following stimulation, T cells were harvested and resuspended in P3 electroporation buffer (Lonza) at a concentration of 1 million cells per 20 uLs of buffer. 5 uLs of RNP (100 pmols) and 1 uL of HDR template (100 pmols) were each added to a 20 uL aliquot of cells (1 million T cells), mixed together, and then electroporated in a single well of a Lonza 4D nucleofection system cuvette using program EH-115. Immediately following electroporation, 80 uLs of pre-warmed culture media were added directly to the cuvette and the cells were allowed to rest (in the cuvette) for 15 minutes in a 5% CO2 37° C. incubator before being stimulated and transferred out for further culture (as described above).

Preparation of Cell Suspension for Penning in OptoSelect™ Chip

T cells were cultured for 1 day or 4 days after electroporation in culture media containing RPMI-1640 (Gibco) supplemented with 2 mmol/L Glutamax (Gibco), 10% (vol/vol) FBS (Seradigm), 2% Human AB serum (ZenBio) and 50 IU/ml IL-2 (R&D Systems, and also in the presence of anti-CD3/CD28 Dynabeads™ (Gibco). Prior to loading onto the OptoSelect™ chip, the T cells were resuspended in culture media supplemented with 10 ng/ml of each of IL-7 and IL-15 (PeProTech) to a final density of 5e6 cells/ml.

Conditions for Automated Cell Penning

Experiments were conducted on commercialized OptoSelect™ chips (Berkeley Lights, Inc.). After priming, chips were washed twice with de-ionized water and flushed 6 times with culture media. Cells were imported onto the chips and loaded as single cells into sequestration pens using OEP force produced with the following parameters: nominal voltage 4.5 V; frequency 1000 kHz; cage shape square; cage speed 8 μm/s; cage line width 10 μm. Loading temperature was set to 36° C. Brightfield images of each chip were acquired automatically at the end of the loading process and a BLI proprietary algorithm was used to detect and count cells in each sequestration pen.

Culturing Conditions and Cell Expansion Quantification

Chips were maintained at a temperature of 36° C. during culture. CO2-buffered culture media was perfused through the chip at a flow rate of 0.01 μl/sec. For primary cell growth assessment and automated counting, Brightfield images of the chips were taken at distinct time points to quantify On-Chip Clonal Expansion (OCCE), defined as the percentage of sequestration pens containing a single cell that grew into a colony of 6 or more cells after 72 h of culture. Cross-contamination across each chip was determined as the percentage of initially empty pens that acquired cells during culture.

On-Chip T Cell Staining

Cell surface staining was performed with anti-CXCR4-PE antibody (12G5; BioLegend). The antibody was imported into the chip at 1:250 dilution in culture media and incubated for 45 min at 36° C. After staining, chips were perfused for 30 min with culture media to remove the excess antibody, and then images were acquired in Brightfield (25 ms) and Texas Red (1000 ms) channels.

Split Export of Edited Clones

Three to four days after loading, clones containing >10 cells that showed negative staining for CXCR4 were sequentially exported for off-chip culturing and genotyping. 48 clones and 48 blanks were exported per chip. In the first step of the split export (culturing export), roughly half of each clone (5-20 cells) was transferred from each selected sequestration pen to the channel using light bars generated by OEP, with the following parameters: nominal voltage 4.5 V; frequency 1000 kHz; bar speed 5 μm/s; bar line width 10 m. Export temperature was set to 36° C., export was performed in culture media and cells were flushed in a 20 ul package volume into a barcoded round-bottom, tissue culture treated 96-well plate containing 100 ul of culture media supplemented with 10 ng/ml of each of IL-7 and IL-15 per well. The plate was kept in an incubator at 36° C. and 5% CO2 for the entire duration of the export. For the second step of the split export (genotyping export), culture media was replaced with Export Buffer containing PBS (Gibco), 5 mg/ml BSA (Fisher Scientific), and 0.1% Pluronic F-127 (Life Tech) by flushing the chip 10 times before starting the export. Then, the remaining cells from each of the previously exported sequestration pens were transferred to the channel by OEP with the following parameters: nominal voltage 5 V; frequency 1000 kHz; bar speed 5 μm/s; bar line width 10 m. Export temperature was set to 36° C., export was performed sequentially in Export Buffer, and the cells from each sequestration pen were flushed in a 5 ul package volume into a barcoded 96-well PCR plate (Eppendorf) containing 20 ul of mineral oil (Sigma-Aldrich) and 5 ul of Proteinase K buffer, containing 10 mM Tris-HCl pH 8, 0.1 M NaCl, 1 mM EDTA, and 200 μg/ml proteinase K (Ambion AM2546), per well. The PCR plate was maintained at 4° C. for the entire duration of the export.

Sample Processing for Next-Generation Sequencing

Genomic DNA was extracted from exported clones by incubating in Proteinase K buffer (0.1 M NaCl, 10 mM Tris HCl pH 8.0, 1 mM EDTA) for 30 min at 55° C., then for 20 min at 80° C. to inactivate Proteinase K. The genomic region around the CRISPR/Cas9 target site for CXCR4 gene was amplified by PCR with primers positioned outside of the HDR repair template sequence (positioned to avoid amplification of exogenous template) for 10 cycles using KAPA HiFi Hotstart ReadyMix (Kapa Biosystems, KR0370) according to the manufacturer's protocol. Primers contained inline sample-specific barcodes. Barcoded samples from each plate were pooled to concentrate and remove mineral oil using Zymo DNA Clean and Concentrator Column (Zymo research, D4004). Excess PCR primers were removed by incubating with Exonuclease I (NEB, M0293S) in 1× Exonuclease Reaction Buffer (NEB, B0293S) for 1 h at 37° C., followed by enzyme inactivation for 20 min at 80° C. Amplicon pools were re-amplified by PCR for 15 cycles using a universal primer to add the sequencing adaptor and secondary barcodes to allow parallel sequencing of multiple amplicon pools. PCR products of the expected size were isolated with Select-A-Size DNA Clean and Concentrator (Zymo research, D4080) for use as sequencing libraries. Pooled barcoded libraries were sequenced with 300 bp paired-end reads on a MiSeq (Illumina) instrument using the 300 cycles v3 reagent kit (Illumina).

Sequencing Data Analysis and HDR/Indel Identification

All computational and statistical analysis were performed using Python 2.7 and Unix-based software tools. Quality of paired-end sequencing reads (R1 and R2 fastq files) was assessed using FastQC (http://www.bioinformatics.babraham.ac.uk/projects/fastqc). Reads with sample-specific inline barcodes were demultiplexed using our home-brew python script for FASTQ files splitting. Reads were then mapped on both the wild type sequence and the expected HDR edited sequence of CXCR4 using bwa version 0.7.15 (20) with default parameters. Alignments files were sorted and indexed using samtools version 1.3.1 (21, 22). Variants were called using freebayes version 1.0.2 (https://arxiv.org/abs/1207.3907), a Bayesian haplotype-based polymorphism discovery tool. Genotypes were determined for each colony based on the number of reads matching either the wild type sequence, the HDR sequence or containing variants to these two sequences with a quality above 30.

Transfection, on-chip clonal expansion, and phenotype assessment

As previously described, human primary T cells were transfected with Cas9 ribonucleoproteins (RNPs) targeting CXCR4, a gene encoding a surface receptor that acts as a coreceptor for HIV (Ref 9, identified below). The RNP complex was mixed with a short ssDNA oligonucleotide HDR template designed to replace 12 nucleotides within CXCR4 (see FIG. 6L) and impair cell surface expression. We previously reported up to ~20% HDR efficiency at this locus (Ref. 9) based on deep sequencing analysis of a bulk population of edited cells. However, bulk sequencing of alleles from a cell population cannot distinguish the portion of mono- and bi-allelic knock-ins at the single-cell level.

Figure 6C:
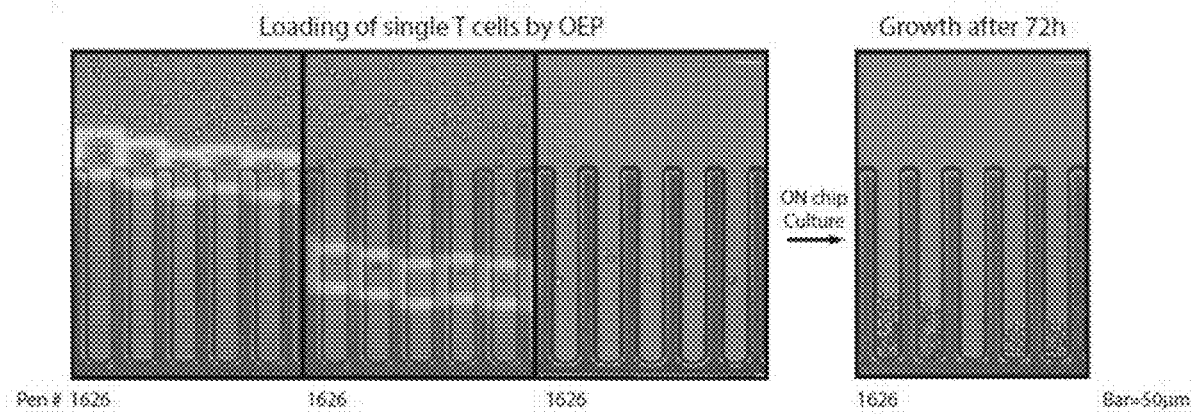
FIG. 6C depicts the selection and isolation of single T cells and their subsequent expansion into clonal populations according to a specific embodiment of the disclosure.
Figure 6D:
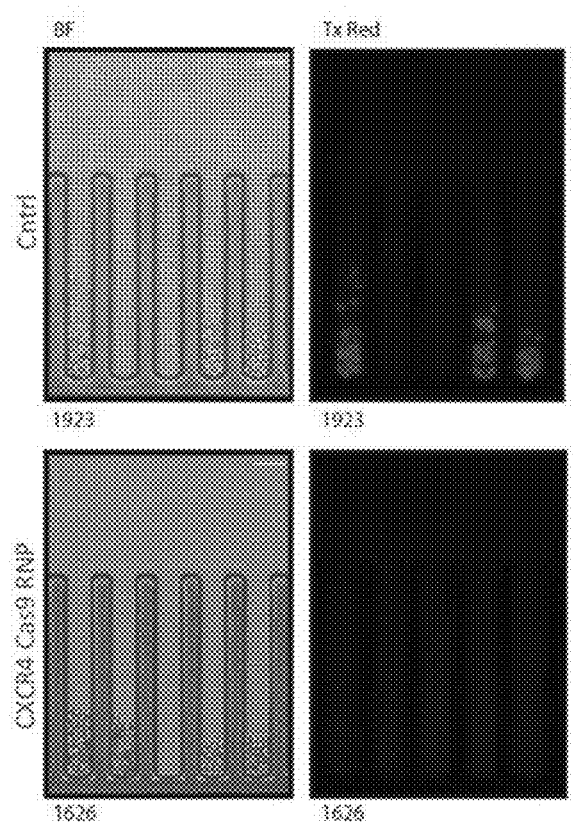
FIG. 6D depicts the results of fluorescence staining of clonal populations of T cells for the cell surface receptor CXCR4 according to a specific embodiment of the disclosure.
Figure 6E:
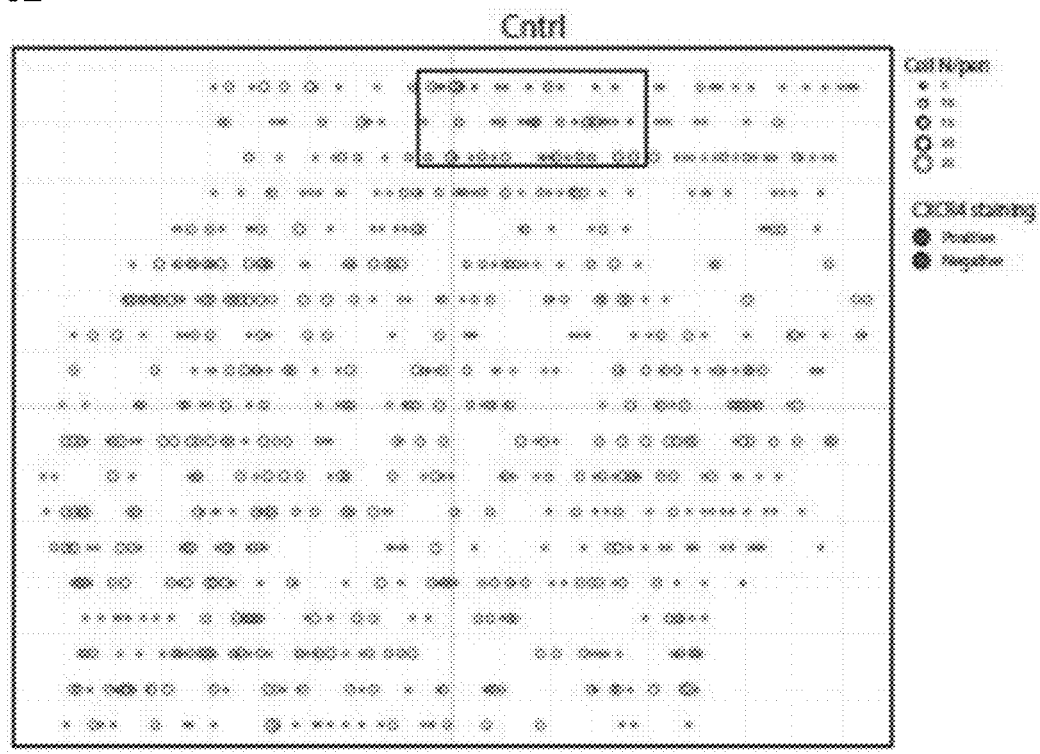
FIG. 6E depicts a graphic representation of on-chip clonal expansion and CXCR4 staining as a function of on-chip position according to a specific embodiment of the disclosure; the box (Cntrl) indicates the field of view (FOV) reserved for scrambled control RNP-treated cells.
Figure 6F:
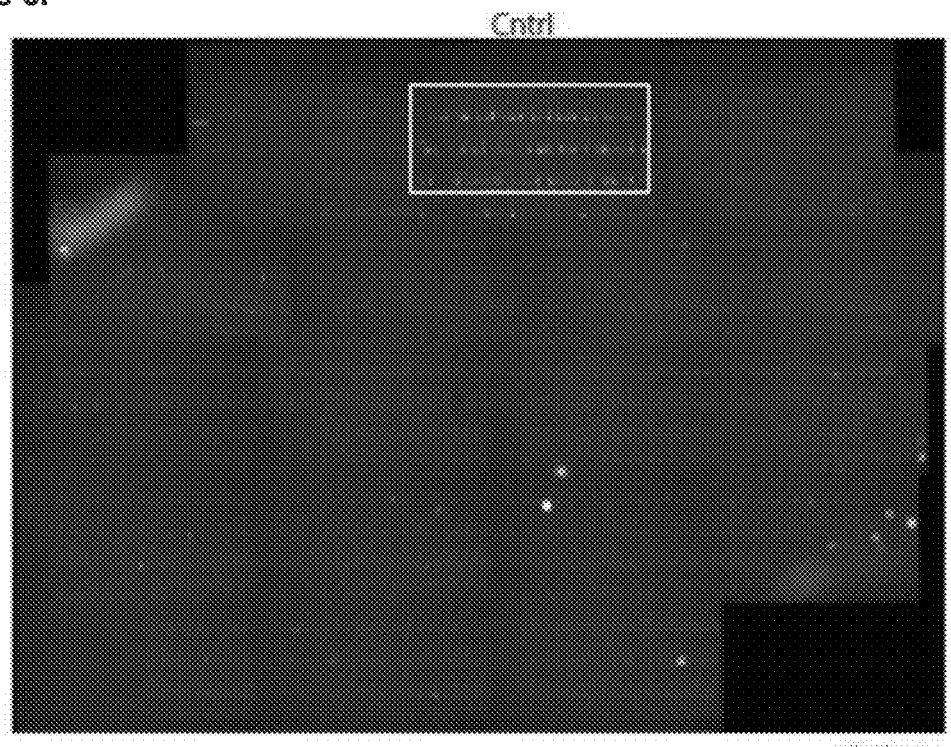
FIG. 6F depicts a composite image of the chip represented in FIG. 6E in the Texas Red channel (Tx Red), showing CXCR4 staining, according to a specific embodiment of the disclosure; the box (Cntrl) indicates the field of view (FOV) reserved for scrambled control RNP-treated cells.
Figure 6G:
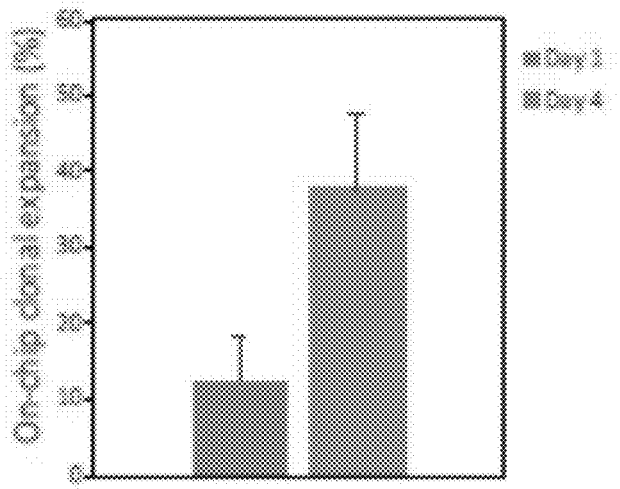
FIG. 6G depicts a graph of the results for on-chip clonal expansion of single T cells loaded 1 or 4 days after electroporation (mean+/−SD of three independent experiments) according to a specific embodiment of the disclosure.

To obtain both phenotypic and genotypic data from individual edited clones, T cells were imported onto the chip one (Day 1) or four days (Day 4) after electroporation with CXCR4 Cas9 RNPs. We assessed editing efficiency at these two time points to identify further timeline compression options. After loading, flow was stopped to keep cells immobile within the main channel. Single cells were automatically selected and trapped into light cages that enable single cell positioning within the sequestration pens, in 17 out of the 18 fields of view (FOVs) that are visualized on the OptoSelect™ chip (FIG. 6C). Non-penned cells remaining within the channel were flushed out of the chip. Importantly, we performed a second import with T cells electroporated with RNPs containing a scrambled control gRNA that does not target any locus in the human genome, positioning them in the remaining FOV (see FIG. 6E). After three days of culture, during which fresh media was perfused into the main channel, we assessed on-chip clonal expansion. We first identified the pens that were initially loaded with single cells (to ensure clonality), and counted the number of pens that contained >6 cells after 3 days of culture. We established, across multiple chips, approximately 15% or 40% of single cells, loaded at day 1 or 4, respectively, formed a colony (FIG. 6G). The size of the individual colonies was heterogeneous (see FIG. 6E). The average doubling time was about 18 hrs over 3 days of growth, with no significant delay in cell division timing (data not shown). These data strongly suggest that diffusion of nutrients from the channel to the sequestration pens maintains cell growth at expected levels. Importantly, we used sequestration pens that were initially empty to track putative on-chip cross-contamination (cell transferred from one pen to another). Fewer than 2% of initially empty pens acquired cells within the three days of culture, indicating greater than 98% on-chip clonality (data not shown). This rare cross-contamination that was observed might be explained by the high motility of activated T cells.

Figure 6H:
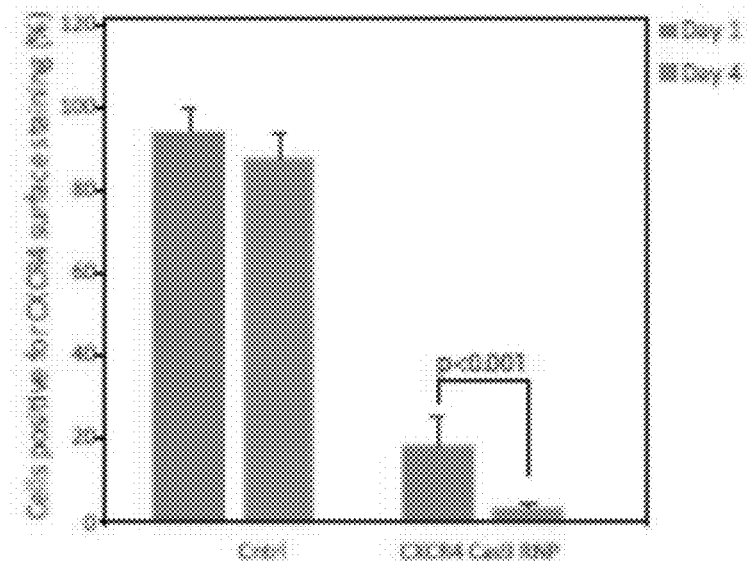
FIG. 6H depicts a graph of the results for CXCR4 staining for control cells and putative edited cells loaded 1 or 4 days after electroporation (mean+/−SD of three independent experiments) according to a specific embodiment of the disclosure.

Next, we established an on-chip phenotypic assay to identify clones that had undergone successful CXCR4 editing. Fluorescently-labeled anti-CXCR4 antibody was imported into the chip, and media flow was interrupted to allow diffusion of the antibody into the pens. After 45 minutes of incubation, the chip was continuously flushed for 30 minutes with fresh media, to remove excess free antibody. Fluorescent images of the entire chip were taken (FIG. 6D, right panels, and FIG. 6F) and the number of colonies positive for CXCR4 surface expression was quantified (FIG. 6H). Among the colonies formed by control cells across all chips, roughly 95% (day 1) and 85% (day 4) of clones were positive for CXCR4 (FIG. 6D, upper right panel, and FIG. 6H). Strikingly, for CXCR4-edited cells loaded 1 day after electroporation, only 20% of the colonies showed presence of CXCR4 on the cell surface. In cells from healthy donors loaded 4 days post-electroporation, the number of colonies positive for CXCR4 staining dropped to around 5%. Importantly, each single pen was assessed for colony formation and fluorescence signal and a report was automatically generated to identify the sequestration pens containing the clones of interest.

Split-Export, On-Target Validation and Selection

Figure 6I:
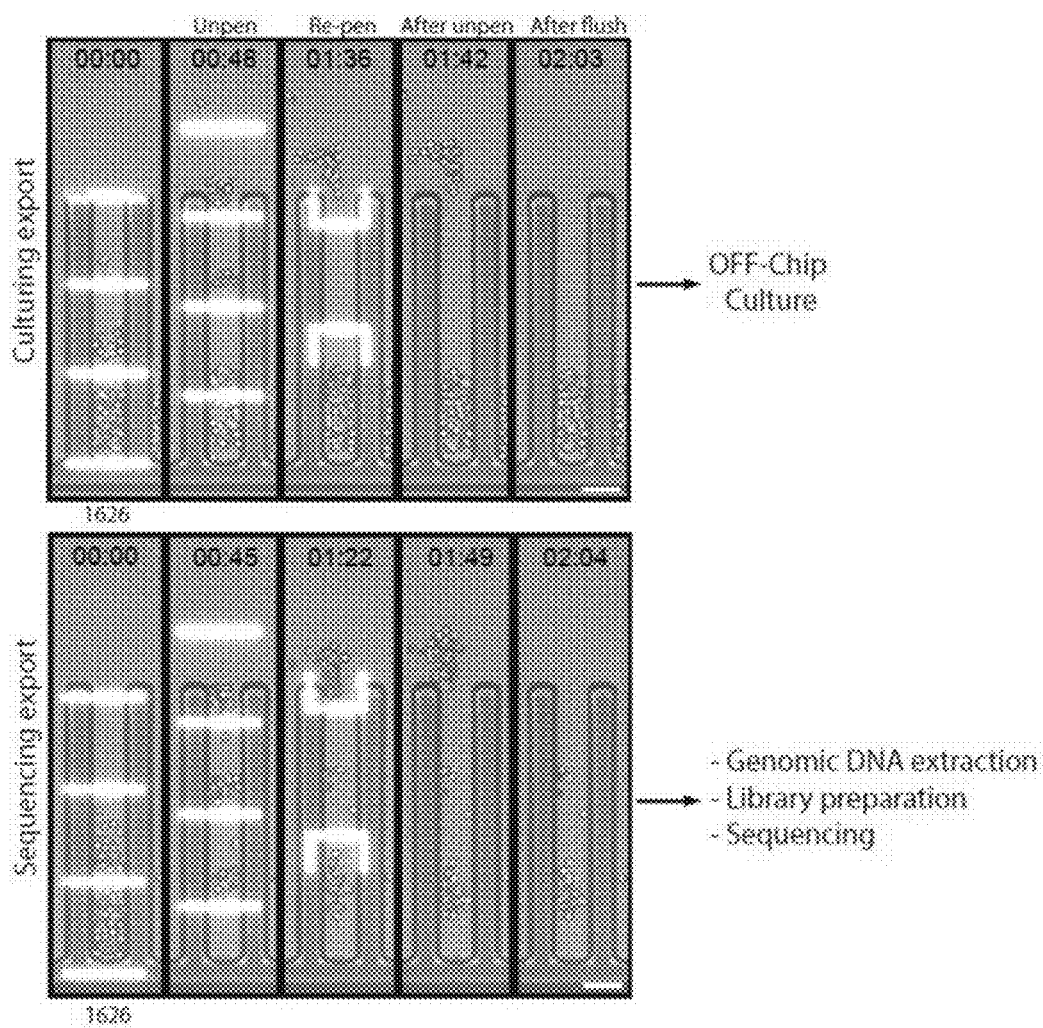
FIG. 6I depicts the export of clonal T populations of T cells for off-chip culture (upper panel) and deep sequencing (lower panel) according to a specific embodiment of the disclosure.
Figure 6J:
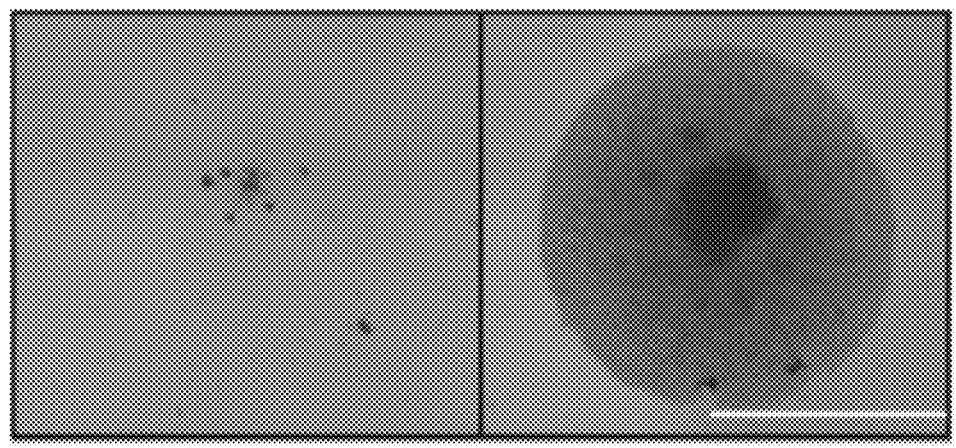
FIG. 6J depicts an image of a representative clonal population of T cells after export (left panel) and following seven days of culture post-export (right panel) according to a specific embodiment of the disclosure.

Among all the putative edited clones that were automatically identified we selected a short list of candidates to export for on-target validation through next generation sequencing (NGS; 48 clones exported per chip, 9 chips in total). Our goal was to validate as early as possible the desirable clones in order to avoid wasting hands-on culturing efforts on clones that were not properly edited. To achieve this, we developed a pipeline that enabled a "split export" for clones of interest. Briefly, for each selected colony, roughly half of the cells were moved from the sequestration pen into the channel via light bars (FIG. 6I, upper panel). Un-penned cells (>5 cells/colony) were flushed out and collected in a defined well of a 96-well plate kept in a CO2- and temperature-controlled incubator for further off-chip culture. We termed this step "culture export." Cells were exported from 48 nano-pens of each chip in this manner. We inserted 48 control blank exports (from empty sequestration pens) between each clonal export to assess cross-contamination between wells introduced during and after export. Following culture export, media was replaced with Export Buffer and the remaining cells from each nano-pen's colony were serially transferred to the main channel (using OEP force, as described above) and flushed out within a small volume of buffer into a corresponding well of a 96-well PCR plate maintained at 4° C. We termed this step "sequencing export." Efficiency of the export process, defined as the fraction of sequestration pens from which more than 1 cell was transferred to the channel, was greater than 80% (data not shown).

Figure 6K:
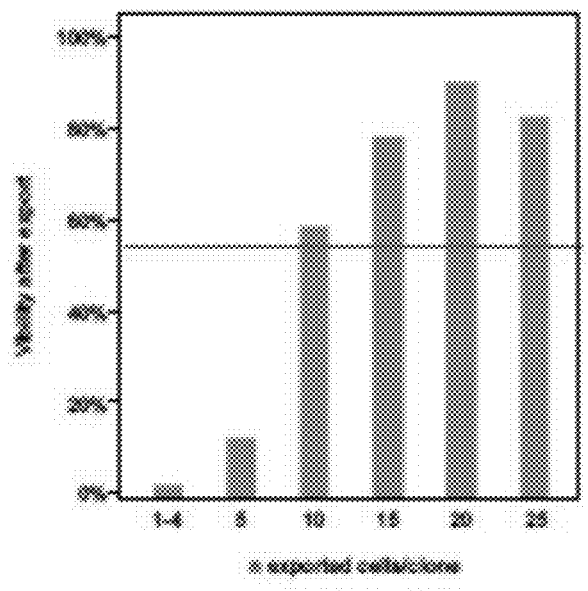
FIG. 6K depicts a graph of cell viability (% of clonal T cell populations forming a colony) following export, as a function of number of cells exported (363 clones analyzed) according to a specific embodiments of the disclosure.
Figures 6L, 6M:
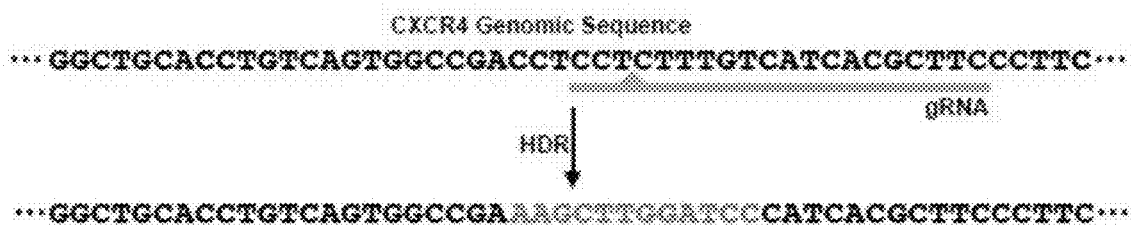
FIG. 6L depicts the target site in the CXCR4 genomic sequence (SEQ ID NO: 10) and the expected sequence following homology-directed repair (HDR) (SEQ ID NO: 11) according to a specific embodiment of the invention.
FIG. 6M depicts different exemplary genotypes (SEQ ID NOs: 10-13) identified in cloned T cell populations according to a specific embodiment of the invention.

Immediately after the sequencing export, collected cells (>5 cells per colony) were lysed and prepared for deep sequencing of the CXCR4 locus. The sequencing reads from each individual clone were then aligned to the CXCR4 WT sequence, the predicted HDR sequence, or neither (called as a NHEJ due to introduced indel or point mutations). Aggregating all the alleles found in cells from clones isolated on-chip on either day one or day four post electroporation allowed for a genotype to be assigned to each clone (FIG. 6M). In one healthy human blood donor, clones could be identified that possessed a variety of genotypes, from no edits at all (WT/WT), to mixed alleles of NHEJ-introduced indels, to mono-allelic HDR (with either WT sequence or indels on the other allele), to bi-allelic HDR (HDR/HDR). Of note, not all CXCR4 edited clones identified with loss of CXCR4 surface expression had 100% editing at the targeted CXCR4 locus, potentially due to Cas9 steric hindering CXCR4 transcription but not inducing a noticeable cut, large deletions unable to be identified by amplicon sequencing, or other unknown factors. More than two individual alleles were found in some clones, potentially due to editing events occurring after the first cell division (i.e. four alleles now present that could be edited), or cross-contamination between wells during culture, export, or NGS library preparation.

Sequencing a portion of a clonal population while maintaining ongoing culture cells from the same colony allowed for clones to be identified based on their genotype, such as bi-allelic HDR. Selected examples of genotypes of clones isolated day four post-electroporation demonstrate the ability to identify such bi-allelic HDR integrations. To assess the fidelity of the off-chip sequencing and confirm the short ssDNA HDR template was not causing sequencing artifacts, we sequenced several individual unedited control clones (unedited controls electroporated with a scrambled gRNA-based Cas9 RNP as well as the same HDR template as used for CXCR4-edited cells) that had been loaded in a pre-determined area of the chip and exported. As expected, greater than 97% of control clones showed no genomic alteration in the targeted CXCR4 locus (WT/WT genotype). Overall, sequencing revealed that bi-allelically edited HDR clones could be identified while maintaining a live culture of the same clones.

Independently, we then assessed the post-export viability within the "Culture Export" plate. Exported clones were maintained for an additional week in culture, then plates were imaged and colony formation was quantified. Depending on the export conditions, up to 80% of the exported clones were able to survive and expand, with an average of roughly 60% of viability across all chips. Notably, we observed some variability in colony survival rates after export. In one case the off-chip post export viability was below 10% (data not shown). In that particular case, the number of cells exported from each pen was on average less than 5. We then refined our analysis, and we observed a strong correlation between the off-chip colony survival rate and the number of cells exported from each sequestration pen (see FIG. 6K). We concluded that, with current protocols, greater than 5 cells (e.g., at least about 6, 7, 8, 9, or 10 cells) should be exported for further off-chip clonal expansion in order to ensure greater than 50% post-export viability.

With approximately 5% bi-allelic HDR editing at the CXCR4 locus and greater than 50% post-export viability, our results indicate that as few as 100 clones could be screened for on-target sequencing validation to ensure that at least 1-2 precisely edited primary human T cell clones are collected after culture export and will survive clonal expansion. This method is immediately relevant to identify and bank accurately edited clones of human primary cells.

Discussion

Cell engineering through gene editing is fundamentally a two-step bioprocess: upstream, delivery of genome editing machinery to the cell type of interest to generate efficient and specific edits; and downstream, identification and selection of the cells that have been properly edited.

CRISPR-Cas9-mediated gene editing is a powerful tool to engineer cells lines and primary cells (Refs. 1-3, identified below). The method enables precise correction or introduction of mutations within an endogenous genomic locus through co-delivery of a DNA template for homology-directed repair (HDR). There are widespread efforts to use this approach in clinically relevant systems to model genetic disorders (Ref. 4, identified below) and for gene therapy to correct disease-driving mutations (Ref. 5, identified below).

Many research and therapeutic applications are currently limited by the low efficiency of precise HDR-based editing. Even with improved delivery of Cas9, some targeted cells remain unedited. In addition, Cas9-mediated DNA breaks are repaired frequently by Non-Homologous End Joining (NHEJ) mechanisms that can introduce varying insertion and deletion mutations (indels) at the cut site resulting in undesirable editing outcomes (Refs. 6, 7, identified below). Precise editing is complicated further because two copies of somatic alleles are present in the diploid genome. Therefore, in a given cell, HDR-mediated editing might occur only on one allele while the other allele is either unedited or imprecisely edited by NHEJ-mediated repair. Progress has been made to enhance the efficiency of HDR-based editing (Ref. 8, identified below), however a technology to identify cells with desired monoallelic or biallelic edits is urgently needed to realize the full potential of CRISPR.

Selection of edited cell clones currently relies on limiting dilution or Fluorescence-Activated Cell Sorting (FACS)-based single-cell sorting to isolate single cells. When genome editing induces a phenotypic alteration that is detectable by fluorescence (i.e. cell surface expression of a target that can be non-lethally assessed with fluorescently-labeled antibody), FACS provides a method of enriching edited cells (Ref. 9, identified below), significantly narrowing the number of clones to propagate and analyze. However, when the desired edit is phenotypically silent, a larger number of clones need to be isolated for subsequent sequencing to ensure that at least one of them has been properly edited. Moreover, even though high-purity cell sorting can be achieved, viability after sorting is often low to moderate, especially for cell types that are particularly sensitive to hydrodynamic stress or low-density culture conditions (e.g. primary cells or pluripotent stem cell lines). As a consequence, investigators often need to isolate a large number of clones and then proceed with tedious and time-consuming efforts to expand all of them individually. Each clonal line must then be assessed by sequencing to find those that bear the desired edits. Generating validated clonal lines can require several weeks. Therefore, the development of a method that allows screening of edited cells and minimizes cell manipulation and hands-on culturing would constitute a significant addition to the current genome engineering toolbox.

Here we demonstrated that the Light-Activated Cell Identification and Sorting (LACIS) method is well suited to isolate clones that have been properly edited with precision. Compared to other methods, LACIS provides multiple advantages: this workflow removes the wasteful hands-on cell culture effort on undesired clones that are not properly edited. In addition, desired clones are identified quickly (<10 days), allowing for increased iterations and faster bioprocess optimizion. Exporting larger numbers of cells per clone directly improves viability and expansion of the selected clones, and therefore contributes to increase the overall process efficiency. Importantly, this workflow can be almost fully automated which will enable significantly enhanced scale relative to current protocols.

The advantages of the OptoSelect™ microfluidic device include the capacity for: 1) massive parallel cell manipulation; 2) on-chip clonal expansion through absolute control of $CO_2$, temperature and media perfusion; 3) on-chip fluorescence-based phenotypic assessment; and 4) sequential export of clones of interest for downstream processing. Every step of the workflow is defined and the process is highly automated such that it can be operated in a >90% hands-off manner. This new platform has allowed us to develop a method that facilitates both identification and selection of properly edited cells, including human primary T cells as shown in the experiments presented below.

In this study, we focused on primary human T-cell editing. We interrogated individual T-cell colonies on-chip after electroporation. Up to 50% of single T cells loaded on chip proliferated into a colony and fewer than 20% of the cells electroporated with CXCR4 editing reagents had detectable CXCR4 cell surface labeling (vs. 80-90% CXCR4+ in control T cells electroporated with scrambled gRNA). After export of selected clones from the chip, further genotypic assessment through on-target sequencing revealed that approximately 5% of the putative edited candidates had bi-allelic HDR-based edits, and more than 50% of the exported clones were able to proliferate. The proposed method enabled the identification and the final selection of those precisely edited clones. Therefore, even for a low-efficiency edit, the presented workflow is advantageous and can guarantee successful selection of cells with the desired genotype, whether or not edited cells can be phenotypically selected.

The present study is the first demonstration of a broadly applicable method that will enable selection of edited cells based on genotype and/or phenotype. The initial use of FACS enabled only a modest 4-fold enrichment of a certain cell sub-type based on one fluorescent criteria (Ref. 10, identified below), but now—nearly 50 years later—enrichment can reach thousands of fold and allows multi-parametric analysis of heterogenous cell populations. This offers some perspective for future improvements in experimental throughput that will require innovative design of the chip to enable massively parallel genotyping and phenotyping throughout the entire chip (>1000 clones) within each run.

REFERENCES (OR "REFS.")

1. Cong L, et al. (2013) Multiplex genome engineering using CRISPR/Cas systems. Science 339(6121):819-823.
2. Jinek M, et al. (2013) RNA-programmed genome editing in human cells. Elife 2:e00471.
3. Mali P, et al. (2013) RNA-guided human genome engineering via Cas9. Science 339(6121):823-826.
4. Dow LE (2015) Modeling Disease In Vivo With CRISPR/Cas9. Trends Mol Med 21(10):609-621.
5. Cox D B, Platt R J, & Zhang F (2015) Therapeutic genome editing: prospects and challenges. Nat Med 21(2):121-131.
6. Doudna J A & Charpentier E (2014) Genome editing. The new frontier of genome engineering with CRISPR-Cas9. Science 346(6213):1258096.
7. Zhang F, Wen Y, & Guo X (2014) CRISPR/Cas9 for genome editing: progress, implications and challenges. Hum Mol Genet 23(R1):R40-46.
8. Paquet D, et al. (2016) Efficient introduction of specific homozygous and heterozygous mutations using CRISPR/Cas9. Nature 533(7601): 125-129.
9. Schumann K, et al. (2015) Generation of knock-in primary human T cells using Cas9 ribonucleoproteins. Proc Natl Acad Sci USA 112(33): 10437-10442.
10. Hulett H R, Bonner W A, Barrett J, & Herzenberg L A (1969) Cell sorting: automated separation of mammalian cells as a function of intracellular fluorescence. Science 166(3906):747-749.

Example 2: Targeted Genome Editing with an ARF1 Genome Editing Biomolecule that Encodes a GFP Reporter HeLa cells ($1\times10^6$ cells) were transfected with 1 microgram of Cas9-encoding plasmid, a guide RNA targeting the endogenous ARF1 sequence (ACTGGCTGTCCAATCAGCTCCGG, SEQ ID NO: 1), and a donor template DNA comprising a portion of ARF1 fused in-frame with an insertion encoding Green Fluorescence Protein (GFP)

(CTGCACTCACTACGCCACAGGAACTGGTACATTCAGGCCACCTGCGCCA

CCAGCGGCGACGGGCTCTATGAAGGACTGGACTGGCTGTCCAATCAACTA

CGAAACCAGAAGGGATCGTCAGGTCGGGATCCAGGCTCAGGTTCTGGAGT

GAGCAAGGGCGAGGAGCTGTTCACCGGGGTGGTGCCCATCCTGGTCGAGC

TGGACGGCGACGTAAACGGCCACAAGTTCAGCGTGTCCGGCGAGGGCGAG

GGCGATGCCACCTACGGCAAGCTGACCCTGAAGTTCATCTGCACCACCGG

CAAGCTGCCCGTGCCCTGGCCCACCCTCGTGACCACCCTGACCTACGGCG

TGCAGTGCTTCAGCCGCTACCCCGACCACATGAAGCAGCACGACTTCTTC

AAGTCCGCCATGCCCGAAGGCTACGTCCAGGAGCGCACCATCTTCTTCAA

-continued

```
GGACGACGGCAACTACAAGACCCGCGCCGAGGTGAAGTTCGAGGGCGACA

CCCTGGTGAACCGCATCGAGCTGAAGGGCATCGACTTCAAGGAGGACGGC

AACATCCTGGGGCACAAGCTGGAGTACAACTACAACAGCCACAACGTCTA

TATCATGGCCGACAAGCAGAAGAACGGCATCAAGGTGAACTTCAAGATCC

GCCACAACATCGAGGACGGCAGCGTGCAGCTCGCCGACCACTACCAGCAG

AACACCCCCATCGGCGACGGCCCCGTGCTGCTGCCCGACAACCACTACCT

GAGCACCCAGTCCGCCCTGAGCAAAGACCCCAACGAGAAGCGCGATCACA

TGGTCCTGCTGGAGTTCGTGACCGCCGCCGGGATCACTCTCGGCATGGAC

GAGCTGTACAAGTAGGCGGCCGCGACT, SEQ ID NO: 2; the underlined portion encodes GFP).
```

The GFP served as a knock-in reporter molecule. The transfection was performed with lipofectamin as the transfection agent.

Following transfection, the population of genome-edited cells were imported into a OptoFluidic™ chip having an SSRL10 coating (Berkeley Lights, Emeryville, Calif.). The chip included microfluidic channels and an OET-configured substrate, with a plurality of NanoPen™ chambers (i.e., sequestration pens) opening off of each microfluidic channel and the OET-configured substrate having a surface defining the base of the channels and sequestration pens. Single cells from the population of genome-edited cells were selected and moved into corresponding sequestration pens, then incubated on chip with regular perfusion of fresh culture medium through the microfluidic channels of the chip.

Figure 7A:
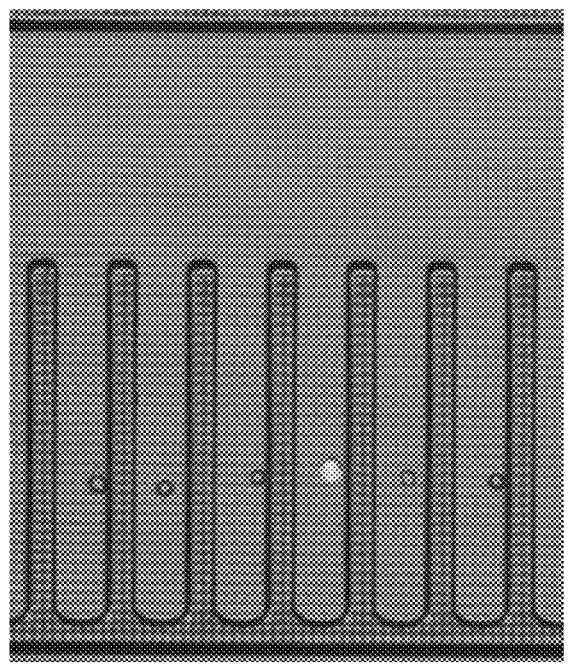
FIGS. 7A and 7B depict the selection of genome-edited cells according to a specific embodiment of the disclosure.
Figure 7B:
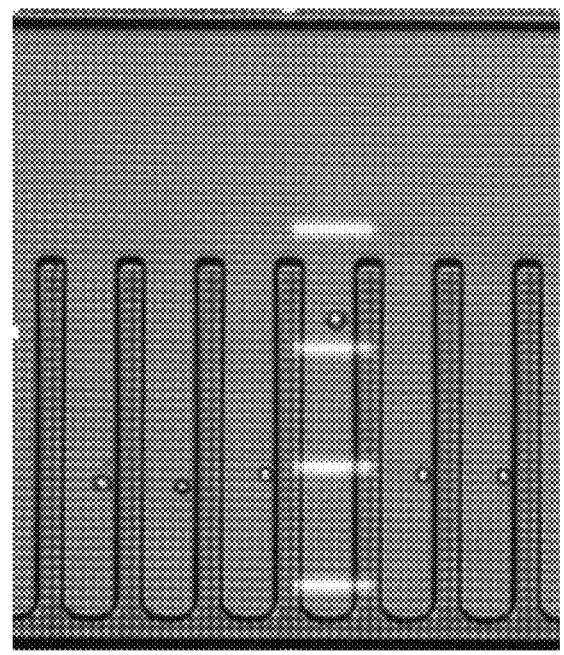

Cells containing on-target genome edits with ARF1-GFP were expected to harbor a golgi-localized fluorescent pattern, known to be in the perinuclear area of the cell. FIGS. 7A and 7B depict images of the transfected HeLa cells following importation into the chip, and selection and movement into sequestration pens. As shown in FIG. 7A, cells that were imported into the microfluidic chip were individually repositioned into a corresponding sequestration pen for expansion into clonal populations. In the image shown in FIG. 7A, the cell in the fourth pen from the left is emitting fluorescent light (appears white), indicating the presence of the GFP reporter molecule. The GFP indicates that the cell was successfully transfected with the genome editing biomolecule. FIG. 7B show patterns of light (shown as white light bars) used to activate the OET-configured substrate and thereby generate OET forces active upon the cell expressing GFP. Movement of the white light bars in the direction of the microfluidic channel results in the effective movement of the OET forces and export of the cell expressing GFP from the sequestration pen.

Figure 8A:
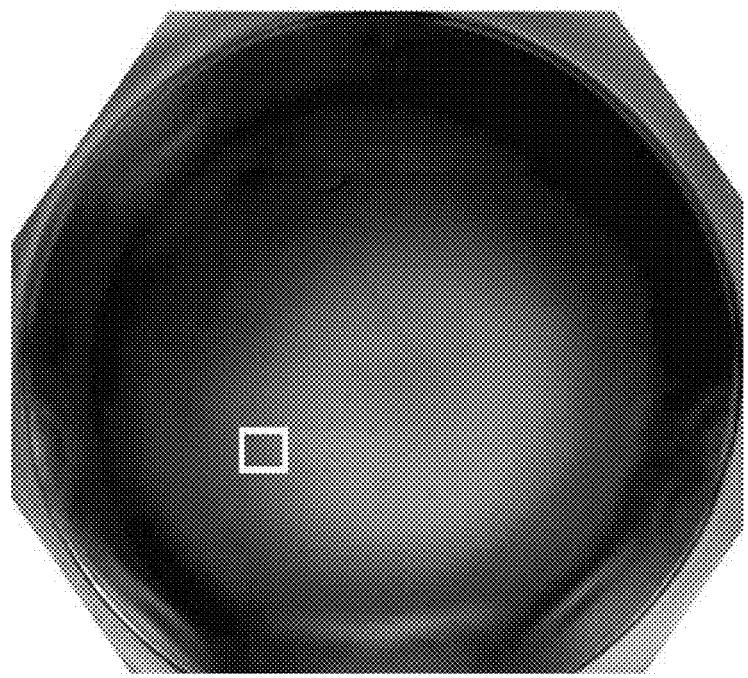
FIGS. 8A and 8B depict the expansion of genome-edited cells according to a specific embodiment of the disclosure.
Figure 8B:
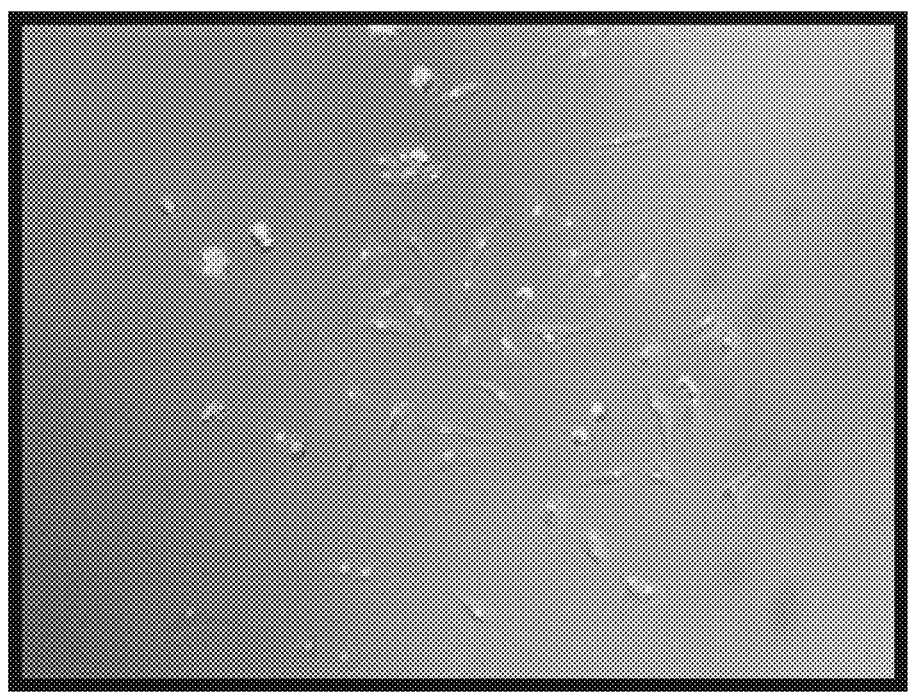

FIGS. 8A and 8B depict transfected HeLa cells deposited in the well of a 96-well plate following export from the microfluidic chip. FIG. 8A depicts the exported cells after two days of culture in the well plate. FIG. 8B depicts an enlarged view of the exported cells after six days of culture in the well plate. As depicted in FIG. 8B, the exported cells continue to produce GFP (shown in white), which is localized in the peri-nuclear area of the cells.

Figure 9:
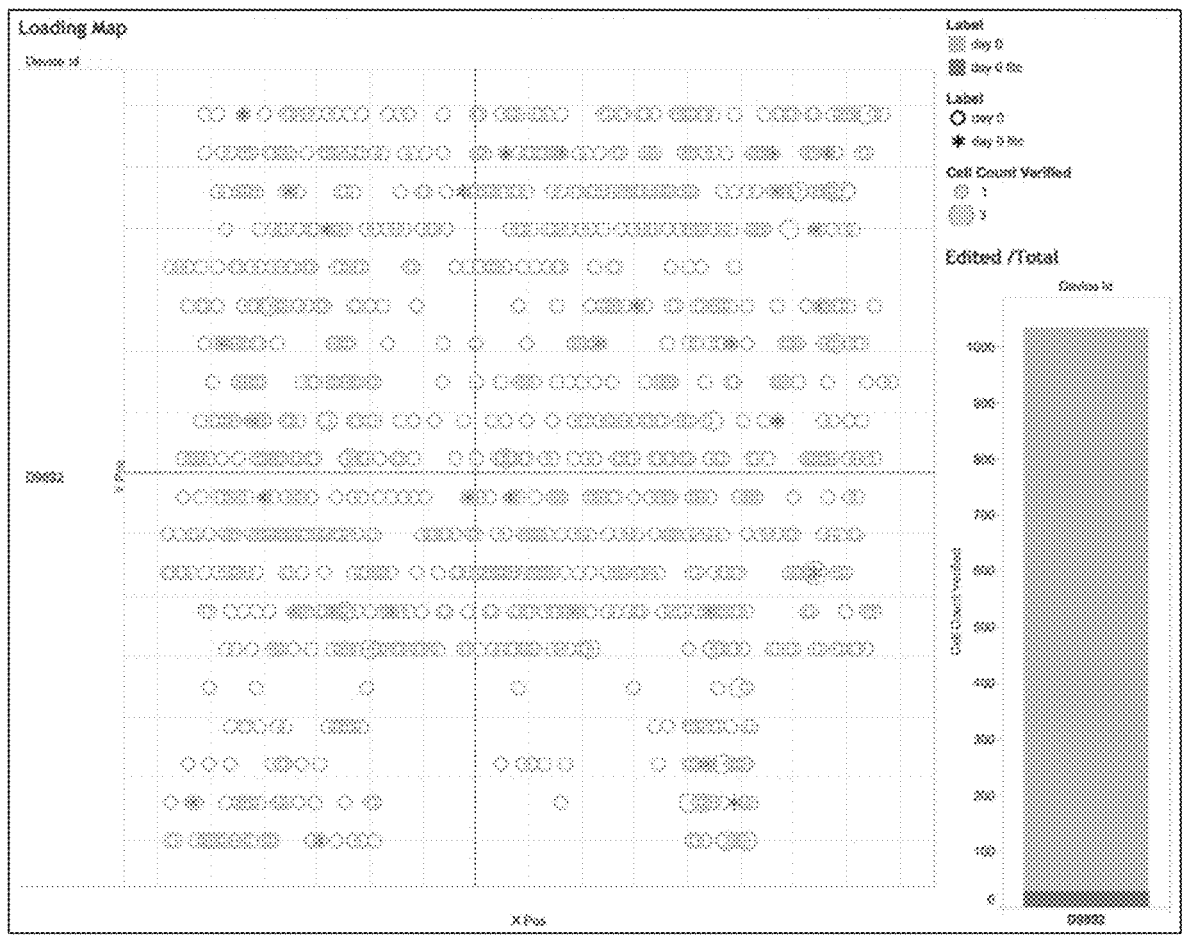
FIG. 9 depicts a plot showing the isolation of genome-edited cells in sequestration pens and the detection of a marker associated with genome editing according to a specific embodiment of the disclosure.

FIG. 9 depicts a plot of the microfluidic chip showing the relative location of sequestration pens in the chip, the number of cells in each pen, and whether a fluorescent signal arising from GFP was produced by the cells in each pen. Each row in the plot corresponds to a row of sequestration pens. Pens containing cells that produce GFP (quantified using a filter for fluorescein isocyanate, or "FITC") are indicated with asterisks and colored in gray; pens with multiple cells are indicated using large circles. As depicted in the plot, a number of cells throughout the microfluidic device produced GFP.

Figure 10:
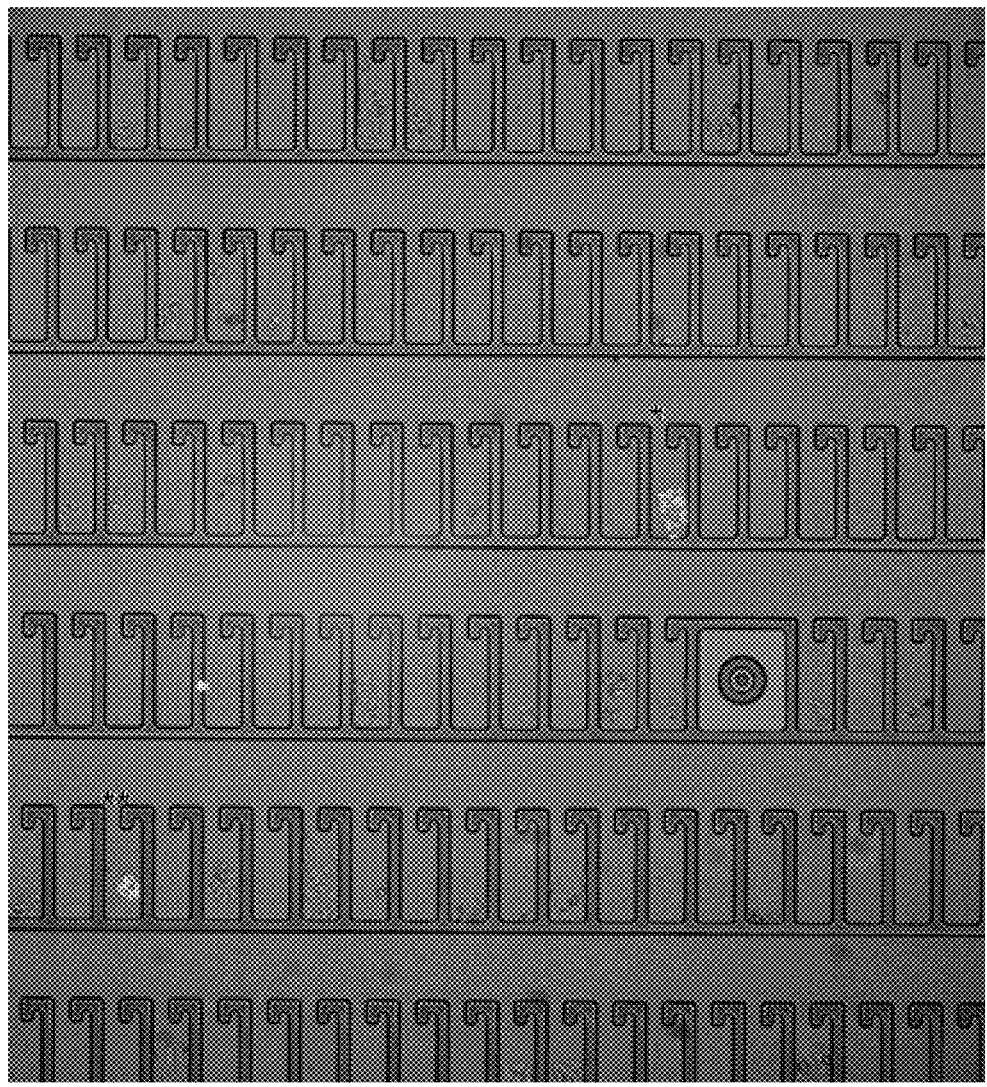
FIG. 10 depicts clonal populations of genome-edited cells according to a specific embodiment of the disclosure.
Figure 11:
FIG. 11 depicts clonal populations of genome-edited cells according to a specific embodiment of the disclosure.

FIGS. 10 and 11 depict images of the microfluidic chip at different time points. FIG. 10 shows a plurality of sequestration pens that were originally loaded with single cells which have expanded into clonal populations of cells following six days of culture on chip. Two of the sequestration pens (marked with single and double asterisks) comprise single cells producing GFP (shown in white) that have expanded into clonal populations; all of the cells in the clonal population of cells in the two sequestration pens produce green fluorescent protein, which is localized within the peri-nuclear (Golgi) area of the cells. FIG. 11 shows the same plurality of sequestration pens after nine days of culture on chip (i.e., three days later). As shown in FIG. 11, the two sequestration pens (marked with single and double asterisks) comprising cells producing GFP contain a larger number of cells than in FIG. 10 due to clonal expansion; again, all of the cells in the clonal populations express GFP.

Figure 12A:
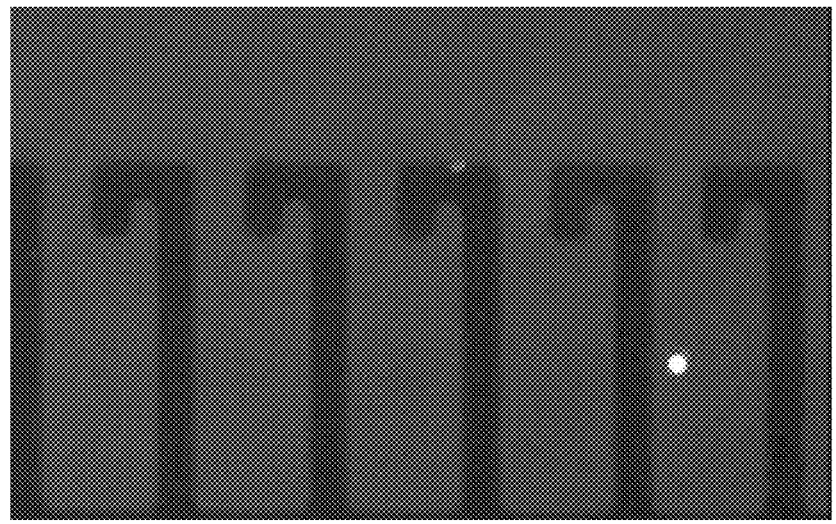
FIGS. 12A-12D depict the expansion of a single genome-edited cell into a clonal population of cells according to a specific embodiment of the disclosure.
Figure 12B:
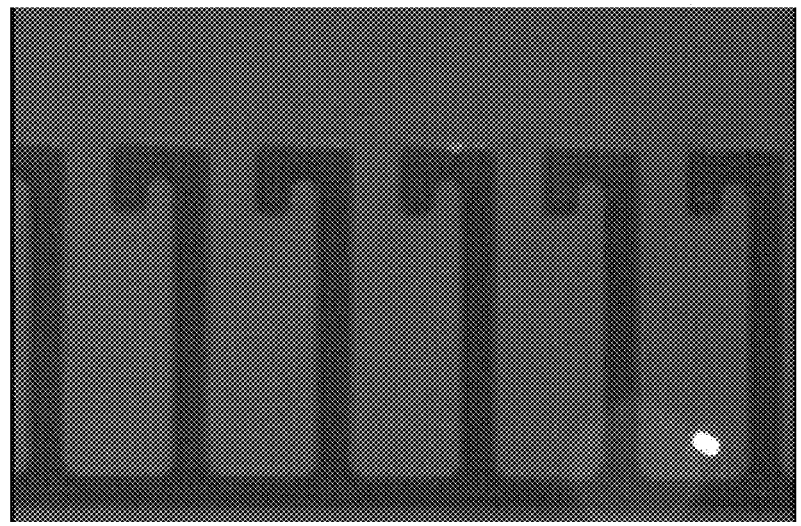
Figure 12C:
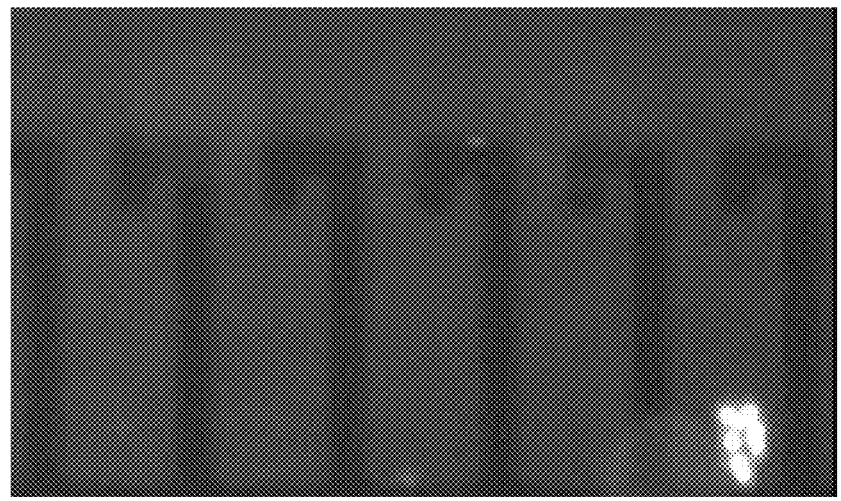
Figure 12D:
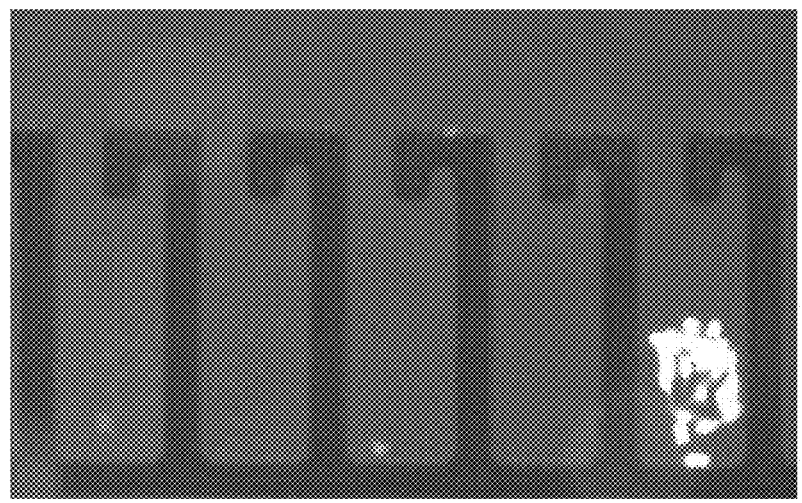

FIGS. 12A-12D provide an enlarged view of the sequestration pen marked with a single asterisk in FIGS. 10 and 11 at progressive time points. As shown in FIGS. 12A (zero hours of culture), 12B (one day of culture), 12C (three days of culture) and 12D (six days of culture), a single cell loaded into the sequestration pen on day zero stably produced GFP as it replicated into a clonal population of cells.

Figure 13:
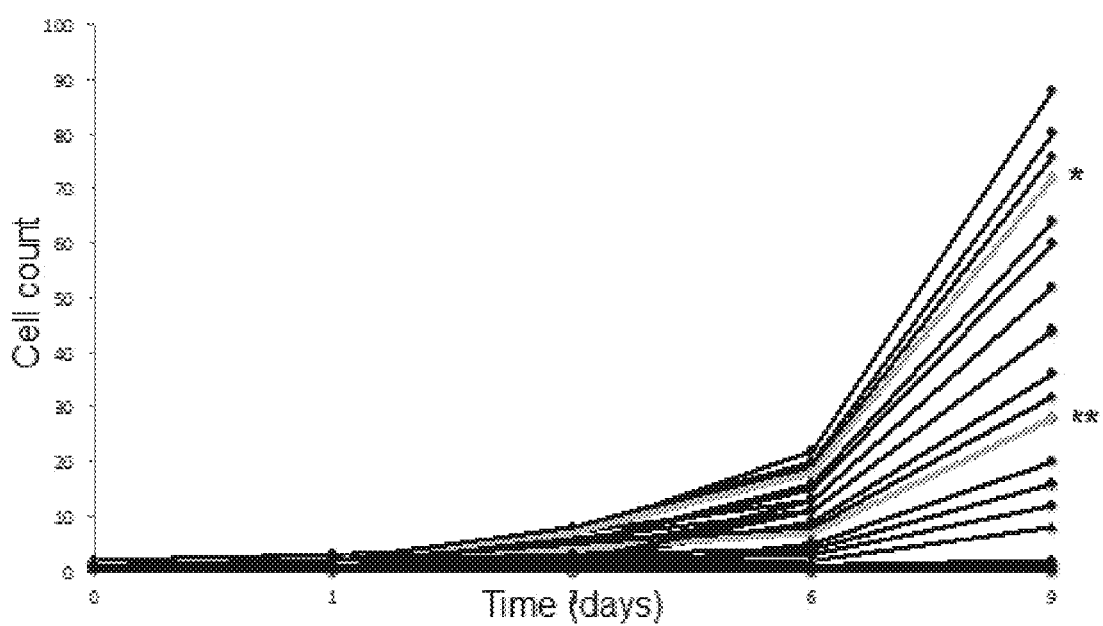
FIG. 13 depicts a graph of clonal expansion for a plurality of genome-edited cells over a nine-day period according to a specific embodiment of the disclosure.

FIG. 13 is a graph of the cell count from the sequestration pens depicted in FIGS. 10 and 11 over the nine-day culture period. Lines representing the two sequestration pens comprising cells that produce GFP are colored in gray and marked with single or double asterisks, as in FIGS. 10 and 11.

Figure 14:
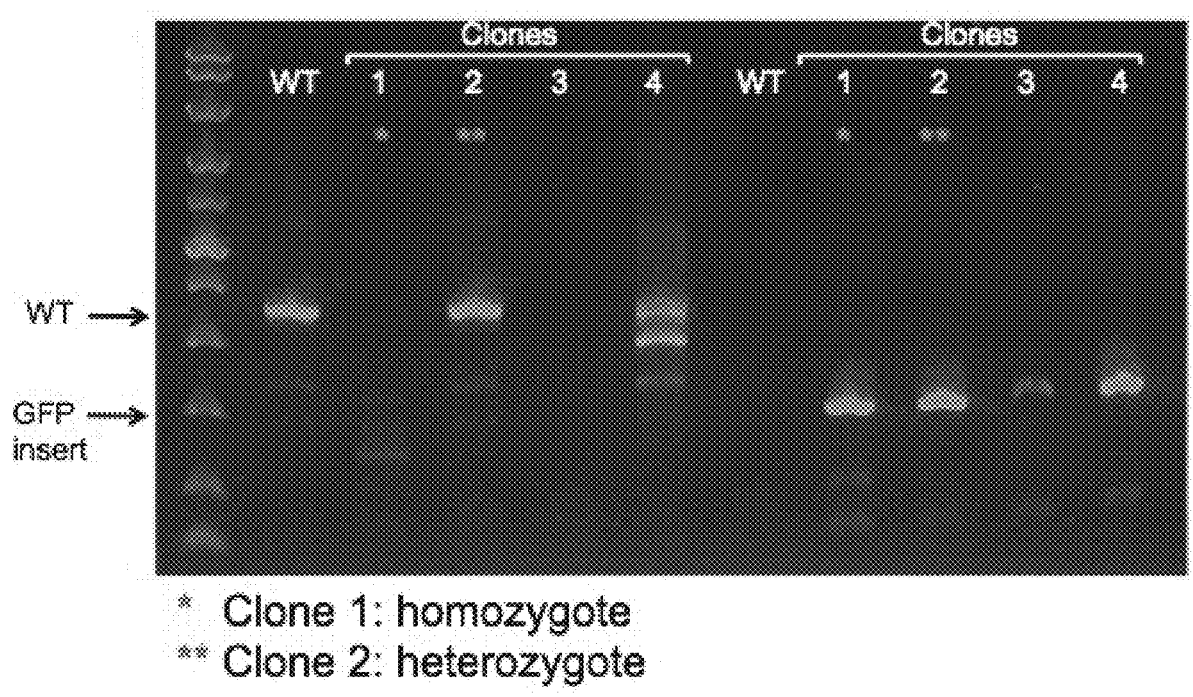
FIG. 14 depicts the use of nucleic acid amplification and analysis to identify on-target genome edits according to a specific embodiment of the disclosure.

Following export, cells from selected clones were lysed, genomic DNA was extracted, and the region of ARF1 flanking the putatively inserted GFP coding region was amplified by means of PCR. The PCR-based amplification included a first PCR reaction (forward primer: ACCTCCC-CAACGCCATGAATGCGG, SEQ ID NO: 3; reverse primer: TGCTAGGCGGGGTCTCCC, SEQ ID NO: 4), designed to amplify a fragment of an ARF1 allele that lacks a GFP insert. See FIG. 14, left panel. The second PCR reaction (forward primer: ACCTCCCCAACGCCAT-GAATGCGG, SEQ ID NO: 5; reverse primer GTGG-CATCGCCCTCGCCCTCG, SEQ ID NO: 6) was designed to amplify the first 100 bp of an ARF1 allele having a GFP-encoding nucleic acid inserted therein. See FIG. 14, right panel. FIG. 14 is an image of an agarose gel following electrophoresis of amplified DNA from the select clones and staining with ethidium bromide. The lane labelled "WT" contains amplicons generated from DNA extracted from wild-type HeLa cells. Lanes labelled "Clone" 1, 2, 3, and 4 include amplicons generated from DNA extracted from the clones of selected cells from the ARF1/GFP Experiment. The lower band (indicated with an arrowhead and the label "GFP insert") corresponds to an amplicon comprising nucleic acid encoding GFP. The upper band (indicated with an arrowhead and the label "WT") corresponds to an amplicon of the endogenous ARF1 sequence; it is only present if the cells have at least one allele that lacks an on-target genome edit. As shown in FIG. 14, the lane for clone 2 has (i) a band indicating the presence of DNA encoding GFP at the ARF1 target site (right panel), and (ii) a band indicating the presence of DNA encoding WT ARF1 (left panel). These bands indicate that clone 2 is heterozygous for the on-target genome edit—that is, only one of the chromosomes in clone 2 was subject to an on-target genome edit. In contrast, clone 1 has a single band indicating the presence of DNA encoding GFP at the ARF1 target site; clone 1 does not have a band indicating the presence of DNA encoding WT ARF1, indicating that clone 1 is homozygous for the on-target genome edit. As expected, the lane for the wild-type cells (WT) only has a band indicating the presence of DNA encoding WT ARF1.

RECITATION OF PARTIAL LIST OF EMBODIMENTS

Embodiment 1

A method of generating a clonal population of genetically modified T cells in a microfluidic device comprising a sequestration pen, the method comprising: maintaining a first T cell in the sequestration pen of the microfluidic device, wherein the first T cell has undergone a genome editing process; expanding the first T cell into a clonal population of T cells; and detecting, in one or more (e.g., all) T cells of the clonal population, the absence of a cell surface marker that was present in the first T cell or precursor thereof.

Embodiment 2

The method of Embodiment 1 further comprising: detecting, in one or more (but not all) T cells of the clonal population, the presence of a first nucleic acid sequence, wherein the first nucleic acid sequence indicates the presence of an on-target genome edit in the clonal population of T cells.

Embodiment 3

A method of generating a clonal population of genetically modified T cells in a microfluidic device comprising a sequestration pen, the method comprising: maintaining a first T cell in the sequestration pen of the microfluidic device, wherein the first T cell has undergone a genome editing process; expanding the first T cell into a clonal population of T cells; and detecting, in one or more T cells of the clonal population, the presence of a first nucleic acid sequence, wherein the first nucleic acid sequence indicates the presence of an on-target genome edit in the clonal population of T cells.

Embodiment 4

The method of any one of Embodiments 1 to 3, wherein the first T cell is a mammalian cell.

Embodiment 5

The method of Embodiment 4, wherein the first T cell is a human cell, a rodent cell, a bovine cell, an ovine cell, a porcine cell, a canine cell, or a feline cell.

Embodiment 6

The method of any one of Embodiments 1 to 5, wherein the first T cell expresses CD3.

Embodiment 7

The method of Embodiment 6, wherein the first T cell further expresses at least one protein selected from the group of CD4, CD8, T-bet, GATA-3, CD25, Foxp3, ROR-gammaT, CD38, and CD40.

Embodiment 8

The method of any one of Embodiments 1 to 7 further comprising: contacting the first T cell with a genome editing biomolecule; and introducing the first T cell into the microfluidic device.

Embodiment 9

The method of Embodiment 8, wherein the genome editing biomolecule comprises a donor template nucleic acid molecule.

Embodiment 10

The method of Embodiment 8, further comprising: contacting the first T cell with a donor template nucleic acid molecule.

Embodiment 11

The method of Embodiment 9 or 10, wherein the donor template nucleic acid molecule comprises all or part of the first nucleic acid sequence.

Embodiment 12

The method of Embodiment 10, wherein the first T cell is contacted with the genome editing biomolecule and the donor template nucleic acid molecule at substantially the same time.

Embodiment 13

The method of any one of Embodiments 8 to 12, wherein the step of transfecting the first T cell is performed prior to the step of introducing the first T cell into the microfluidic device.

Embodiment 14

The method of any one of Embodiments 8 to 12, wherein the step of introducing the first T cell into the microfluidic device is performed prior to the step of transfecting the first T cell.

Embodiment 15

The method of any one of Embodiments 8 to 14, further comprising: selecting the first T cell for transfection based on one or more characteristics selected from morphology, size, production of a protein of interest, the presence of one or more cell surface markers, and/or reaction with a specific antibody.

Embodiment 16

The method of Embodiment 15, further comprising: positioning the first T cell in the sequestration pen, wherein said positioning is performed after selecting the first T cell.

Embodiment 17

The method of any one of Embodiments 1 to 16, wherein the microfluidic device comprises a substrate having a DEP-configuration, and wherein the method further comprises positioning the first T cell in the sequestration pen using dielectrophoretic (DEP) force.

Embodiment 18

The method of any one of Embodiments 1 to 17, wherein detecting the first nucleic acid sequence comprises: selecting one or more (but not all) T cells from the clonal population of T cells; and extracting nucleic acid from the one or more selected T cells.

Embodiment 19

The method of Embodiment 18, further comprising: moving the one or more selected T cells out of the sequestration pen; and exporting the one or more selected T cells from the microfluidic device, wherein the nucleic acid is extracted from the one or more selected T cells outside of the microfluidic device.

Embodiment 20

The method of Embodiment 18, further comprising: moving the one or more selected T cells from the sequestration pen to a separate region within the microfluidic device, wherein the nucleic acid is extracted from the one or more selected T cells in the separate region.

Embodiment 21

The method of any one of Embodiments 18 to 20, further comprising: amplifying the extracted nucleic acid.

Embodiment 22

The method of Embodiment 21, wherein amplifying the extracted nucleic acid comprises performing polymerase chain reaction (PCR) amplification.

Embodiment 23

The method of Embodiment 21 or 22, wherein amplifying the extracted nucleic acid comprising performing whole genome amplification (WGA).

Embodiment 24

The method of any one of Embodiments 21 to 23, wherein amplifying the extracted nucleic acid comprises amplifying the first nucleic acid sequence.

Embodiment 25

The method of any one of Embodiments 18 to 24, wherein the extracted nucleic acid comprises genomic DNA.

Embodiment 26

The method of any one of Embodiments 18 to 25, wherein the extracted nucleic acid comprises ribonucleic acid (RNA).

Embodiment 27

The method of Embodiment 26, further comprising: reverse transcribing the extracted RNA with a reverse transcriptase.

Embodiment 28

The method of any one of Embodiments 2 to 27, wherein the on-target genome edit comprises a deletion of endogenous deoxyribonucleic acid (DNA) at a target site in the genome.

Embodiment 29

The method of any one of Embodiments 2 to 28, wherein the on-target genome edit comprises an insertion of exogenous deoxyribonucleic acid (DNA) at a target site in the genome.

Embodiment 30

The method of Embodiment 29, wherein the insertion encodes a functional biomolecule, a barcode, and/or a reporter molecule.

Embodiment 31

The method of Embodiment 29 or 30, wherein detecting the presence of the first nucleic acid sequence comprises detecting all or part of the insertion.

Embodiment 32

The method of any one of Embodiments 2 to 31, further comprising: detecting, in one of more (but not all) T cells of the clonal population of T cells, the presence of a second nucleic acid sequence, wherein the combination of the first nucleic acid sequence and the second nucleic acid sequence indicates the presence of the on-target genome edit in the clonal population of T cells.

Embodiment 33

The method of any one of Embodiments 2 to 32, further comprising: detecting, in one of more cells of the clonal population of T cells, the presence of an additional nucleic acid sequence, wherein the additional nucleic acid sequence indicates the presence of an off-target genome edit in the clonal population of T cells.

Embodiment 34

The method of Embodiment 33, wherein the off-target genome edit comprises a deletion of endogenous DNA and/or an insertion of exogenous DNA at a site in the genome other than the target site.

Embodiment 35

The method of any one of Embodiments 1 to 34, wherein the microfluidic device comprises a first portion having a substrate that has a dielectrophoresis (DEP) configuration and a second portion that has a substrate that has an electrowetting (EW) configuration, and wherein the sequestration pen is located in the first portion of the microfluidic device.

Embodiment 36

The method of any one of Embodiments 1 to 34, wherein the microfluidic device comprises a first substrate having a dielectrophoresis (DEP) configuration and a second substrate having an electrowetting (EW) configuration, the first and second substrates connected via a bridging region, and wherein the sequestration pen is in a portion of the microfluidic device comprising the first substrate.

Embodiment 37

The method of any one of Embodiments 1 to 36, wherein expanding the first T cell into a clonal population of T cells further comprises: monitoring one or more characteristics of the T cells of the clonal population for a period of time.

Embodiment 38

The method of Embodiment 37, wherein the monitoring is performed periodically during the period of time.

Embodiment 39

The method of Embodiment 37, wherein the monitoring is performed substantially continuously during the period of time.

Embodiment 40

The method of any one of Embodiments 37 to 39, wherein the monitoring comprises identifying changes in the size and/or morphology of the T cells of the clonal population.

Embodiment 41

The method of any one of Embodiments 37 to 40, wherein the monitoring comprises determining the rate of proliferation of the first T cell into the clonal population of T cells.

Embodiment 42

The method of any one of Embodiments 37 to 41, wherein the monitoring comprises assessing the production of a protein of interest, the presence of one or more cell surface markers, and/or reaction with a specific antibody.

Embodiment 43

The method of any one of Embodiments 1 to 42, further comprising: exporting one or more (e.g., all) cells of the clonal population of genetically modified T cells from the microfluidic device into a well plate, and culturing the one or more T cells in the well plate.

Embodiment 44

The method of any one of Embodiments 1 to 43, wherein at least one inner surface of the sequestration pen, or a portion thereof, is a conditioned surface.

Embodiment 45

The method of Embodiment 44, wherein the conditioned surface comprises covalently-linked molecules, each having a linking group covalently bound to the at least one inner surface of the sequestration pen, or the portion thereof, and a moiety covalently bound to the linking group, wherein the moieties of the covalently-linked molecules provide a layer of organic and/or hydrophilic molecules suitable for maintenance and/or expansion of the genome-edited first cell.

Embodiment 46

The method of Embodiment 45, wherein each moiety is a polymer comprising polyethylene glycol, saccharides, or amino acids.

Embodiment 47

The method of Embodiment 46, wherein each moiety of a first subset of the covalently-linked molecules is a polymer that comprises amino acids, and wherein each moiety of a second subset of the covalently-linked molecules is a polymer that comprises polyethylene glycol or saccharides.

Embodiment 48

The method of any one of Embodiments 1 to 47, wherein the microfluidic device comprises a plurality of sequestration pens, and wherein the method is performed on a plurality of T cells to thereby generate a plurality of clonal populations of genetically modified T cells.

Embodiment 49

The method of Embodiment 48, wherein one or more steps of the method are performed on the plurality of T cells in parallel.

Embodiment 50

A composition comprising, consisting of, or consisting essentially of a clonal population of genetically modified T cells, wherein the clonal population was generated by any one of the methods of Embodiments 1 to 47.

Embodiment 51

The composition of Embodiment 50, further comprising a plurality of clonal populations of genetically modified T cells, wherein each clonal population was generated by any one of the methods of Embodiments 1 to 47.

Embodiment 52

The composition of Embodiment 51i, wherein the plurality of clonal populations of genetically modified T cells together comprise at least 1000 genetically modified T cells.

Embodiment 53

The composition of Embodiment 51, wherein the plurality of clonal populations of genetically modified T cells together comprise at least 10,000 genetically modified T cells.

Embodiment 54

The composition of any one of Embodiments 50 to 53, further comprising a pharmaceutically acceptable carrier.

Although specific embodiments and applications of the invention have been described in this specification, these embodiments and applications are exemplary only, and many variations are possible.

What is claimed:

1. A method of generating a clonal population of genetically modified T cells in a microfluidic device comprising a sequestration pen, the method comprising:
   maintaining a first T cell in the sequestration pen of the microfluidic device, wherein the first T cell has undergone a genome editing process;
   expanding the first T cell into a clonal population of T cells;
   detecting, in one or more T cells of the clonal population, the absence of a cell surface marker that was present in the first T cell or precursor thereof; and
   detecting, in one or more T cells of the clonal population, the presence of a first nucleic acid sequence, wherein the first nucleic acid sequence indicates the presence of an on-target genome edit in the clonal population of T cells.

2. A method of generating a clonal population of genetically modified T cells in a microfluidic device comprising a sequestration pen, the method comprising:
   maintaining a first T cell in the sequestration pen of the microfluidic device, wherein the first T cell has undergone a genome editing process;
   expanding the first T cell into a clonal population of T cells; and
   detecting, in one or more T cells of the clonal population, the presence of a first nucleic acid sequence, wherein the first nucleic acid sequence indicates the presence of an on-target genome edit in the clonal population of T cells.

3. The method of claim 1, wherein the first T cell is a mammalian cell.

4. The method of claim 3, wherein the first T cell is a human cell.

5. The method of claim 3, wherein the first T cell expresses CD3 and at least one of CD4, CD8, T-bet, GATA-3, CD25, Foxp3, ROR-gammaT, CD38, and CD40.

6. The method of claim 1 further comprising:
   contacting the first T cell with a genome editing biomolecule; and
   introducing the first T cell into the microfluidic device.

7. The method of claim 6, wherein the genome editing biomolecule comprises a donor template nucleic acid molecule or the method further comprises contacting the first T cell with a donor template nucleic acid molecule.

8. The method of claim 7, wherein the donor template nucleic acid molecule comprises all or part of the first nucleic acid sequence.

9. The method of claim 6, wherein contacting the first T cell with a genome editing biomolecule is performed prior to introducing the first T cell into the microfluidic device.

10. The method of claim 6, wherein introducing the first T cell into the microfluidic device is performed prior to contacting the first T cell with a genome editing biomolecule.

11. The method of claim 6, further comprising:
selecting the first T cell based on one or more characteristics selected from morphology, size, production of a protein of interest, the presence of one or more cell surface markers, and/or reaction with a specific antibody.

12. The method of claim 11, further comprising:
positioning the first T cell in the sequestration pen, wherein said positioning is performed after selecting the first T cell.

13. The method of claim 1, wherein the microfluidic device comprises a substrate having a DEP-configuration, and
wherein the method further comprises positioning the first T cell in the sequestration pen using dielectrophoretic (DEP) force.

14. The method of claim 1, wherein detecting the presence of the first nucleic acid sequence comprises:
selecting one or more T cells from the clonal population of T cells; and
extracting nucleic acid from the one or more selected T cells.

15. The method of claim 14, further comprising:
(i) moving the one or more selected T cells out of the sequestration pen; and
exporting the one or more selected T cells from the microfluidic device, wherein the nucleic acid is extracted from the one or more selected T cells outside of the microfluidic device;
(ii) moving the one or more selected T cells from the sequestration pen to a separate region within the microfluidic device, wherein the nucleic acid is extracted from the one or more selected T cells in the separate region; or
(iii) amplifying the extracted nucleic acid.

16. The method of claim 1, wherein the on-target genome edit comprises a deletion of endogenous deoxyribonucleic acid (DNA) or an insertion of exogenous deoxyribonucleic acid (DNA) at a target site in the genome.

17. The method of claim 16, wherein the insertion encodes a functional biomolecule, a barcode, and/or a reporter molecule.

18. The method of claim 1, further comprising:
(i) detecting, in one or more T cells of the clonal population of T cells, the presence of a second nucleic acid sequence, wherein the combination of the first nucleic acid sequence and the second nucleic acid sequence indicates the presence of the on-target genome edit in the clonal population of T cells; or
(ii) detecting, in one or more cells of the clonal population of T cells, the presence of an additional nucleic acid sequence, wherein the additional nucleic acid sequence indicates the presence of an off-target genome edit in the clonal population of T cells, and wherein the off-target genome edit comprises a deletion of endogenous DNA and/or an insertion of exogenous DNA at a site in the genome other than the target site.

19. The method of claim 1, wherein the microfluidic device comprises a first portion having a substrate that has a dielectrophoresis (DEP) configuration and a second portion that has a substrate that has an electrowetting (EW) configuration, and wherein the sequestration pen is located in the first portion of the microfluidic device.

20. The method of claim 1, wherein expanding the first T cell into a clonal population of T cells further comprises:
monitoring one or more characteristics of the T cells of the clonal population for a period of time.

21. The method of claim 20, wherein the monitoring comprises:
identifying changes in the size and/or morphology of the T cells of the clonal population;
determining the rate of proliferation of the first T cell into the clonal population of T cells; and/or
assessing the production of a protein of interest, the presence of one or more cell surface markers, and/or reaction with a specific antibody.

22. The method of claim 1, further comprising:
exporting one or more cells of the clonal population of genetically modified T cells from the microfluidic device into a well plate, and
culturing the one or more T cells in the well plate.

23. A method of generating a clonal population of genetically modified T cells in a microfluidic device comprising a sequestration pen, the method comprising:
maintaining a first T cell in the sequestration pen of the microfluidic device, wherein the first T cell has undergone a genome editing process;
expanding the first T cell into a clonal population of T cells;
detecting, in one or more T cells of the clonal population, the absence of a cell surface marker that was present in the first T cell or precursor thereof; and
detecting, in one or more T cells of the clonal population, the presence of a first nucleic acid sequence, wherein the first nucleic acid sequence indicates the presence of an on-target genome edit in the clonal population of T cells,
wherein at least one inner surface of the sequestration pen, or a portion thereof, is a conditioned surface, wherein the conditioned surface comprises covalently-linked molecules, each having a linking group covalently bound to the at least one inner surface of the sequestration pen, or the portion thereof, and a moiety covalently bound to the linking group, wherein the moieties of the covalently-linked molecules provide a layer of organic and/or hydrophilic molecules suitable for maintenance and/or expansion of the genome-edited first cell.

24. The method of claim 1, wherein the microfluidic device comprises a plurality of sequestration pens, and wherein the method is performed on a plurality of T cells to thereby generate a plurality of clonal populations of genetically modified T cells, optionally wherein one or more steps of the method are performed on the plurality of T cells in parallel.

25. A composition comprising a clonal population of genetically modified T cells, wherein the clonal population was generated by the method of claim 1.

26. The method of claim 1, wherein the one or more T cells of the clonal population on which detecting the presence of a first nucleic acid sequence is performed is a first subset of the clonal population of T cells, and wherein a second subset of the clonal population of T cells is preserved.

* * * * *

SEQUENCE LISTING

<160> NUMBER OF SEQ ID NOS: 13

<210> SEQ ID NO 1
<211> LENGTH: 23
<212> TYPE: DNA
<213> ORGANISM: Artificial Sequence
<220> FEATURE:
<223> OTHER INFORMATION: Guide RNA targeting endogenous ARF1 sequence

<400> SEQUENCE: 1
actggctgtc caatcagctc cgg                                              23

<210> SEQ ID NO 2
<211> LENGTH: 876
<212> TYPE: DNA
<213> ORGANISM: Artificial Sequence
<220> FEATURE:
<223> OTHER INFORMATION: Donor template DNA comprising a portion of ARF1
      fused in-frame with an insertion encoding Green Fluorescence
      Protein (GFP)

<400> SEQUENCE: 2
ctgcactcac tacgccacag gaactggtac attcaggcca cctgcgccac cagcggcgac        60
gggctctatg aaggactgga ctggctgtcc aatcaactac gaaaccagaa gggatcgtca       120
ggtcgggatc caggctcagg ttctggagtg agcaagggcg aggagctgtt caccggggtg       180
gtgcccatcc tggtcgagct ggacggcgac gtaaacggcc acaagttcag cgtgtccggc       240
gagggcgagg gcgatgccac ctacggcaag ctgaccctga agttcatctg caccaccggc       300
aagctgcccg tgccctggcc caccctcgtg accaccctga cctacggcgt gcagtgcttc       360
agccgctacc ccgaccacat gaagcagcac gacttcttca gtccgccat gcccgaaggc        420 tacgtccagg agcgcaccat cttcttcaag gacgacggca actacaagac ccgcgccgag       480
gtgaagttcg agggcgacac cctggtgaac cgcatcgagc tgaagggcat cgacttcaag       540
gaggacggca acatcctggg gcacaagctg gagtacaact acaacagcca caacgtctat       600
atcatggccg acaagcagaa gaacggcatc aaggtgaact tcaagatccg ccacaacatc       660
gaggacggca gcgtgcagct cgccgaccac taccagcaga caccccccat cggcgacggc       720
cccgtgctgc tgcccgacaa ccactacctg agcacccagt ccgccctgag caaagacccc      780
aacgagaagc gcgatcacat ggtcctgctg gagttcgtga ccgccgccgg gatcactctc      840
ggcatggacg agctgtacaa gtaggcggcc gcgact                                876

<210> SEQ ID NO 3
<211> LENGTH: 24
<212> TYPE: DNA
<213> ORGANISM: Artificial Sequence
<220> FEATURE:
<223> OTHER INFORMATION: Forward primer F1 designed to amplify a region
      of ARF1 that lacks a GFP insert

<400> SEQUENCE: 3
acctccccaa cgccatgaat gcgg                                             24

<210> SEQ ID NO 4
<211> LENGTH: 18
<212> TYPE: DNA
<213> ORGANISM: Artificial Sequence
<220> FEATURE:
<223> OTHER INFORMATION: Reverse primer R1 designed to amplify a region
      of ARF1 that lacks a GFP insert

```
<400> SEQUENCE: 4
tgctaggcgg ggtctccc                                                    18

<210> SEQ ID NO 5
<211> LENGTH: 24
<212> TYPE: DNA
<213> ORGANISM: Artificial Sequence
<220> FEATURE:
<223> OTHER INFORMATION: Forward primer F2 designed to amplify the first
      100 bps of an ARF1 allele having a GFP-encoding nucleic acid
      inserted therein

<400> SEQUENCE: 5
acctccccaa cgccatgaat gcgg                                             24

<210> SEQ ID NO 6
<211> LENGTH: 21
<212> TYPE: DNA
<213> ORGANISM: Artificial Sequence
<220> FEATURE:
<223> OTHER INFORMATION: Reverse primer R2 designed to amplify the first
      100 bps of an ARF1 allele having a GFP-encoding nucleic acid
      inserted therein

<400> SEQUENCE: 6
gtggcatcgc cctcgccctc g                                                21

<210> SEQ ID NO 7
<211> LENGTH: 20
<212> TYPE: DNA
<213> ORGANISM: Artificial Sequence
<220> FEATURE:
<223> OTHER INFORMATION: Guide RNA targeting endogenous CXCR4 sequence

<400> SEQUENCE: 7
gaagcgtgat gacaaagagg                                                  20

<210> SEQ ID NO 8
<211> LENGTH: 20
<212> TYPE: DNA
<213> ORGANISM: Artificial Sequence
<220> FEATURE:
<223> OTHER INFORMATION: Guide RNA having scrambled sequence

<400> SEQUENCE: 8
ggttcttgac taccgtaatt                                                  20

<210> SEQ ID NO 9
<211> LENGTH: 192
<212> TYPE: DNA
<213> ORGANISM: Artificial Sequence
<220> FEATURE:
<223> OTHER INFORMATION: Donor template DNA comprising a portion of
      CXCR4 fused in-frame with a defined 12 nucleotide insertion

<400> SEQUENCE: 9
gggcaatgga ttggtcatcc tggtcatggg ttaccagaag aaactgagaa gcatgacgga      60
caagtacagg ctgcacctgt cagtggccga aagcttggat cccatcacgc ttcccttctg    120
ggcagttgat gccgtggcaa actggtactt tgggaacttc ctatgcaagg cagtccatgt    180
catctacaca gt                                                         192
```

```
<210> SEQ ID NO 10
<211> LENGTH: 50
<212> TYPE: DNA
<213> ORGANISM: Artificial Sequence
<220> FEATURE:
<223> OTHER INFORMATION: Sequence of a portion of a CXCR4 genomic locus
      containing a gene editing target site prior to gene editing

<400> SEQUENCE: 10
ggctgcacct gtcagtggcc gacctcctct ttgtcatcac gcttcccttc                50

<210> SEQ ID NO 11
<211> LENGTH: 50
<212> TYPE: DNA
<213> ORGANISM: Artificial Sequence
<220> FEATURE:
<223> OTHER INFORMATION: Sequence of a portion of a CXCR4 genomic locus
      containing a gene editing target site after gene editing with HDR

<400> SEQUENCE: 11
ggctgcacct gtcagtggcc gaaagcttgg atcccatcac gcttcccttc                50

<210> SEQ ID NO 12
<211> LENGTH: 46
<212> TYPE: DNA
<213> ORGANISM: Artificial Sequence
<220> FEATURE:
<223> OTHER INFORMATION: Sequence of a portion of a CXCR4 genomic locus
      containing a gene editing target site after gene editing with NHEJ

<400> SEQUENCE: 12
ggctgcacct gtcagtggcc gacctccttt catcacgctt cccttc                    46

<210> SEQ ID NO 13
<211> LENGTH: 48
<212> TYPE: DNA
<213> ORGANISM: Artificial Sequence
<220> FEATURE:
<223> OTHER INFORMATION: Sequence of a portion of a CXCR4 genomic locus
      containing a gene editing target site after gene editing with NHEJ

<400> SEQUENCE: 13
ggctgcacct gtcagtggcc gacctccttt gtcatcacgc ttcccttc                  48
```